(12) United States Patent
Cramer et al.

(10) Patent No.: US 7,096,162 B2
(45) Date of Patent: Aug. 22, 2006

(54) COMPUTER-IMPLEMENTED METHOD OF MERGING LIBRARIES OF MOLECULES USING VALIDATED MOLECULAR STRUCTURAL DESCRIPTORS AND NEIGHBORHOOD DISTANCES TO MAXIMIZE DIVERSITY AND MINIMIZE REDUNDANCY

(76) Inventors: Richard D. Cramer, 48 Camino de Miagro, Sante Fe, NM (US) 87506; David E. Patterson, 2808 Regent St., Apt B, Berkeley, CA (US) 94705

( * ) Notice: Subject to any disclaimer, the term of this patent is extended or adjusted under 35 U.S.C. 154(b) by 271 days.

(21) Appl. No.: 09/776,711

(22) Filed: Feb. 5, 2001

(65) Prior Publication Data

US 2004/0215397 A1    Oct. 28, 2004

Related U.S. Application Data

(62) Division of application No. 08/592,132, filed on Jan. 26, 1996, now Pat. No. 6,185,506.

(51) Int. Cl.
*G06G 7/48*      (2006.01)
*G01N 33/48*    (2006.01)
*G06F 7/00*      (2006.01)

(52) U.S. Cl. .............................. 703/1; 702/19; 702/20; 707/102

(58) Field of Classification Search ............ 702/27, 702/19, 20; 435/DIG. 1–DIG. 50, DIG. 51; 707/102
See application file for complete search history.

(56) References Cited

U.S. PATENT DOCUMENTS

| | | | | |
|---|---|---|---|---|
| 4,642,762 A * | 2/1987 | Fisanick | .......................... | 707/3 |
| 4,811,217 A * | 3/1989 | Tokizane et al. | ................. | 707/3 |
| 5,025,388 A * | 6/1991 | Cramer et al. | ............... | 700/293 |
| 5,056,035 A * | 10/1991 | Fujita | ............................ | 703/12 |
| 5,157,736 A * | 10/1992 | Boyer et al. | ................. | 382/113 |
| 5,270,170 A * | 12/1993 | Schatz et al. | ............... | 435/7.37 |
| 5,307,287 A * | 4/1994 | Cramer et al. | ................... | 703/2 |
| 5,345,516 A * | 9/1994 | Boyer et al. | .................. | 382/113 |
| 5,386,507 A * | 1/1995 | Teig et al. | ..................... | 715/836 |
| 5,418,944 A * | 5/1995 | DiPace et al. | ................... | 707/3 |
| 5,424,963 A * | 6/1995 | Turner et al. | .................... | 703/6 |
| 5,434,796 A * | 7/1995 | Weininger | ...................... | 703/12 |
| 5,463,564 A * | 10/1995 | Agrafiotis et al. | ........... | 700/268 |
| 5,500,807 A * | 3/1996 | Lavin et al. | .................... | 702/22 |
| 5,526,281 A * | 6/1996 | Chapman et al. | .............. | 702/22 |
| 5,555,366 A * | 9/1996 | Teig et al. | .................... | 711/169 |
| 5,574,656 A * | 11/1996 | Agrafiotis et al. | ........... | 700/268 |
| 5,577,239 A * | 11/1996 | Moore et al. | .................... | 707/3 |
| 5,583,973 A * | 12/1996 | DeLisi et al. | ................ | 345/420 |
| 5,619,421 A * | 4/1997 | Venkataraman et al. | ....... | 702/27 |
| 5,703,792 A * | 12/1997 | Chapman | ....................... | 702/27 |
| 6,185,506 B1 * | 2/2001 | Cramer et al. | ................. | 702/19 |
| 6,240,374 B1 * | 5/2001 | Cramer et al. | ................. | 703/11 |
| 2003/0009298 A1 * | 1/2003 | Pitman et al. | ................. | 702/27 |

* cited by examiner

*Primary Examiner*—Mary K. Zeman
(74) *Attorney, Agent, or Firm*—Laurence Weinberger

(57) ABSTRACT

The use for biological screening purposes of a subset (library) of a large combinatorially accessible chemical universe increases the efficiency of the screening process only if the subset contains members representative of the total diversity of the universe. In order to insure inclusion in the subset of molecules representing the total diversity of the universe under consideration, valid molecular descriptors which quantitatively reflect the diversity of the molecules in the universe are required. A unique validation method is used to examine both a new three dimensional steric metric and some prior art metrics. With this method, the relative usefulness/validity of individual metrics can be ascertained from their application to randomly selected literature data sets. By the appropriate application of validated metrics, the method of this invention selects a subset of a combinatorial accessible chemical universe such that the molecules of the subset are representative of all the diversity present in the universe and yet do not contain multiple members which represent the same diversity (oversample). The use of the neighborhood definition of a validated metric may also be used to combine (without oversampling the same diversity) any number of combinatorial screening libraries.

3 Claims, 27 Drawing Sheets

8B
REMOVE NON-DIVERSE REACTANTS:
  3D STRUCTURE GENERATION
  TOPOMERIC CONFORMER
    ALIGNMENT
  CoMFA FIELD GENERATION:
    HYDROGEN BOND FIELD
      GENERATION
    ROTATABLE BOND FIELD
      ATTENUATION
  CALCULATE FIELD
    DIFFERENCES
  CLUSTER
  REACTANT SELECTION FROM
    EACH CLUSTER

SYBYL: SELECTOR &
  CONCORD 3.2.1
    SPECIALIZED SOFTWARE:
      APPENDIX "A"
      (SYBYL: CoMFA
        STERIC & MSS)

SYBYL: HIERCHICAL
  CLUSTER - MSS
SYLBL: MSS

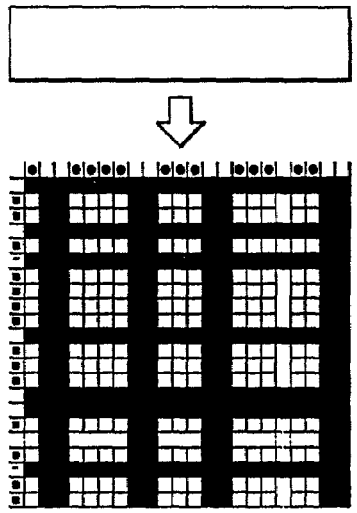

8C
COMBINE REACTANTS TO BUILD PRODUCTS

SYBYL: LEGION MSS

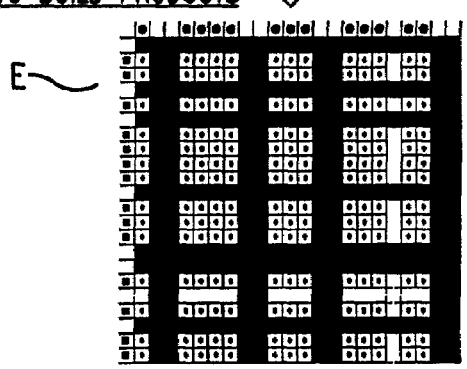

8D
REMOVE PRODUCTS:
  NON-DIVERSITY REASONS
  GENERAL CRITERIA:

SYBYL: SPL SCRIPTS
  ON MSS

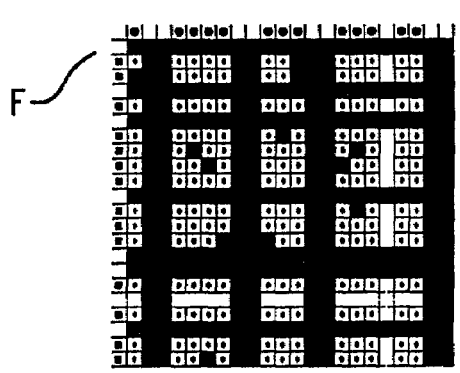

FIG.11(b)

COMPUTER-IMPLEMENTED METHOD OF MERGING LIBRARIES OF MOLECULES USING VALIDATED MOLECULAR STRUCTURAL DESCRIPTORS AND NEIGHBORHOOD DISTANCES TO MAXIMIZE DIVERSITY AND MINIMIZE REDUNDANCY

This patent application is a division of application Ser. No. 08/592,132 filed on Jan. 26, 1996 and issued on Feb. 6, 2001 as U.S. Pat. No. 6,185,506.

BACKGROUND OF THE INVENTION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

1. Field of the Invention

This invention relates to the field of combinatorial chemistry screening libraries and more specifically to: 1) a method of validating the molecular structural descriptors necessary for designing an optimal combinatorial screening library; 2) a method of designing an optimal combinatorial screening library; 3) a method of merging libraries derived from different combinatorial chemistries; and 4) methods of following up and optimizing identified leads. The libraries designed by the method are constructed to ensure that an optimal structural diversity of compounds is represented. In particular, the invention describes the design of libraries of small molecules to be used for pharmacological testing.

2. Description of Related Art

Statement of the Problem

While the present invention is discussed with detailed reference to the search for and identification of pharmacologically useful chemical compounds, the invention is applicable to any attempt to search for and identify chemical compounds which have some desired physical or chemical characteristic(s). The broader teachings of this invention are easily recognized if a different functional utility or useful property describing other chemical systems is substituted below for the term "biological activity".

Starting with the serendipitous discovery of penicillin by Fleming and the subsequent directed searches for additional antibiotics by Waksman and Dubos, the field of drug discovery during the post World War II era has been driven by the belief that nature would provide many needed drugs if only a careful and diligent search for them was conducted. Consequently, pharmaceutical companies undertook massive screening programs which tested samples of natural products (typically isolated from soil or plants) for their biological properties. In a parallel effort to increase the effectiveness of the discovered "lead" compounds, medicinal chemists learned to synthesize derivatives and analogs of the compounds. Over the years, as biochemists identified new enzymes and biological reactions, large scale screening continued as compounds were tested for biological activity in an ever rapidly expanding number of biochemical pathways. However, proportionately fewer and fewer lead compounds possessing a desired therapeutic activity have been discovered. In an attempt to extend the range of compounds available for testing, during the last few years the search for unique biological materials has been extended to all corners of the earth including sources from both the tropical rain forests and the ocean. Despite these and other efforts, it is estimated that discovery and development of each new drug still takes about 12 years and costs on the order of 350 million dollars.

Beginning approximately twenty-five years ago, as bio-scientists learned more about the chemical and stereochemical requirements for biological interactions, a variety of semi-empirical, theoretical, and quantitative approaches to drug design were developed. These approaches were accelerated by the availability of powerful computers to perform computational chemistry. It was hoped that the era of "rational drug design" would shorten the time between significant discoveries and also provide an approach to discovering compounds active in biological pathways for which no drugs had yet been discovered. In large part, this work was based on the accumulated observation of medicinal chemists that compounds which were structurally similar also possessed similar biological activities. While significant strides were made using this approach, it too, like the mass screening programs, failed to provide a solution to the problem of rapidly discovering new compounds with activities in the ever increasing number of biological pathways being elucidated by modern biotechnology.

During the past four or five years, a revised screening approach has been under development which, it was hoped, would accelerate the pace of drug discovery. In fact, the approach has been remarkably successful and represents one of the most active areas in biotechnology today. This new approach utilizes combinatorial libraries against which biological assays are screened. Combinatorial libraries are collections of molecules generated by synthetic pathways in which either: 1) two groups of reactants are combined to form products; or 2) one or more positions on core molecules are substituted by a different chemical constituent/moiety selected from a large number of possible constituents.

Two fundamental ideas underlie combinatorial screening libraries. The first idea, common to all drug research, is that somewhere amongst the diversity of all possible chemical structures there exist molecules which have the appropriate shape and binding properties to interact with any biological system. The second idea is the belief that synthesizing and testing many molecules in parallel is a more efficient way (in terms of time and cost) to find a molecule possessing a desired activity than the random testing of compounds, no matter what their source. In the broadest context, these ideas require that, since the binding requirements of a ligand to the biological systems under study (enzymes, membranes, receptors, antibodies, whole cell preparations, genetic materials, etc.) are not known, the screened compounds should possess as broad a range of characteristics (chemical and physical) as possible in order to increase the likelihood of finding one that is appropriate for any given biological target. This requirement for a screening library is reflected in the term "diversity"—essentially a way of suggesting that the library should contain as great a dissimilarity of compounds as possible.

However, as is immediately apparent, a combinatorial approach to synthesizing molecules generates an immense number of compounds many with a high degree of structural similarity. In fact, the number of compounds synthetically accessible with known organic reactions exceeds by many orders of magnitude the numbers which can actually be made and tested. One area where these ideas were first explored is in the design of peptide libraries. For a library of five member peptides synthesized using the 20 naturally occurring amino acids, 3,200,000, ($20^5$) different peptides may be constructed. The number of combinatorial possibilities increases even more dramatically when non-peptide combinatorial libraries are considered. With non-peptide libraries, the whole synthetic chemical universe of combinatorial possibilities is available. Library sizes ranging from $5\times10^7$ to $4\times10^{12}$ molecules are now being discussed. The enormous universe of chemical compounds is both a blessing and a curse to medicinal chemists seeking new drugs. On the one hand, if a molecule exists with the desired biological activity, it should be included in the chemical universe. On the other hand, it may be impossible to find. Thus, the principal focus of recent efforts has been to define smaller screening subsets of molecules derivable from accessible combinatorial syntheses without losing the inherent diversity of an accessible universe.

To date, in order to narrow the focus of the search and reduce the number of compounds to be screened, attention has been directed to designing biologically specific libraries. Thus, many combinatorial screening libraries existing in the prior art have been designed based on prior knowledge about a particular biological system such as a known pharmacophore (a geometric arrangement of structural fragments abstracted from molecular structures known to have activity). Even with this knowledge, molecules are included in these prior art libraries based on intuition—"seat of the pants" estimations of likely similarity based on an intuitive "feel" for the systems under study. This procedure is essentially pseudo-random screening, not rational library design. Several biotechnology startup companies have developed just such proprietary libraries, and success using combinatorial libraries has been achieved by sheer effort. In one example 18 libraries containing 43 million compounds were screened to identify 27 active compounds[1]. With library searches of this magnitude, it is most likely that the enormous number of inactive molecules [$(43\times10^6)$–27] must have included staggering numbers of redundantly inactive molecules—molecules not significantly distinguishable from one another—even in libraries designed with a particular biological target in mind. Clearly, when searching for a lead molecule which interacts with an uncharacterized biological target, approaches requiring knowledge of the biological targets will not work. But finding such a lead is exactly the case for which it is hoped general purpose screening libraries can be designed. If the promise of combinatorial chemistry is ever to be fully realized, some rational and quantitative method of reducing the astronomical number of compounds accessible in the combinatorial chemistry universe to a number which can be usefully tested is required. In other words, the efficiency of the search process must be increased. For this purpose, a smaller rationally designed screening library, which still retains the diversity of the combinatorially accessible compounds, is absolutely necessary.

Thus, there are two criteria which must be met by any screening library subset of some universe of combinatorially accessible compounds. First, the diversity, the dissimilarity of the universe of compounds accessible by some combinatorial reaction, must be retained in the screening subset. A subset which does not contain examples of the total range of diversity in such a universe would potentially miss critical molecules, thereby frustrating the very reason for the creation of the subset. Second, for efficient screening, the ideal subset should not contain more than one compound representative of each aspect of the diversity of the larger group. If more than one example were included, the same diversity would be tested more than once. Such redundant screening would yield no new information while simultaneously increasing the number of compounds which must be synthesized and screened. Therefore, the fundamental problem is how to reduce to a manageable number the number of compounds that need to be synthesized and tested while at the same time providing a reasonably high probability that no possible molecule of biological importance is overlooked. (In this regard, it should be recognized that the only way of absolutely insuring that all diversity is represented in a library is to include and test all compounds.) A conceptual analogy to the problem might be: what kind of filter can be constructed to sort out from the middle of a blinding snowstorm individual snowflakes which represent all the classes of crystal structures which snowflakes can form?

The fundamental question plaguing progress in this area has been whether the concept of the diversity of molecular structure can be usefully described and quantified; that is, how is it possible to compare/distinguish the physical and chemical properties determinative of biological activity of one molecule with that of another molecule? Without some way to quantitatively describe diversity, no meaningful filter can be constructed. Fortunately, for biological systems, the accumulated wisdom of bioscientists has recognized a general principle alluded to earlier which provides a handle on this problem. As framed by Johnson and Maggiora[2], the principle is simply stated as: "structurally similar molecules are expected to exhibit similar (biological) properties." Based on this principle, quantifying diversity becomes a matter of quantifying the notion of structural similarity. Thus, for design of a screening subset of a combinatorial library (hereafter referred to as a "combinatorial screening library"), it should only be necessary to identify which molecules are structurally similar and which structurally dissimilar. According to the selection criteria outlined above, one molecule of each structurally similar group in the combinatorially accessible chemical universe would be included in the library subset. Such a library would be an optimally diverse combinatorial screening library. The problem for medicinal chemists is to determine how the intuitively perceived notions of structural similarity of chemical compounds can be validly quantified. Once this question is satisfactorily answered, it should be possible to rationally design combinatorial screening libraries.

Prior Art Approaches

Many descriptors of molecular structure have been created in the prior art in an attempt to quantify structural similarity and/or dissimilarity. As the art has recognized, however, no method currently exists to distinguish those descriptors that quantify useful aspects of similarity from those which do not. The importance of being able to validate molecular descriptors has been a vexing problem restricting advances in the art, and, before this invention, no generally applicable and satisfactory answer had been found. The problem may be conceptualized in terms of a multidimensional space of structurally derivable properties which is populated by all possible combinatorially accessible chemical compounds. Compounds lying "near" one another in any one dimension may lie "far apart" from one another in another dimension. The difficulty is to find a useful design space—a quantifiable dimensional space (metric space) in which compounds with similar biological properties cluster; ie., are found measurably near to each other. What is desired is a molecular structural descriptor which, when applied to the molecules of the chemical universe, defines a dimensional space in which the "nearness" of the molecules with respect to a specified characteristic (ie.; biological activity) in the chemical universe is preserved in the dimensional space. A molecular structural descriptor (metric) which does not have this property is useless as a descriptor of molecular diversity. A valid descriptor is defined as one which has this property.

In light of the above, it should be noted that there is a difference between a descriptor being valid and being perfect. There may or may not be a "perfect" metric which precisely and quantitatively maps the diversity of compounds (much less those of biological interest). However, a good approximation is sufficient for purposes of designing a combinatorial screening library and is considered valid/useful. Acceptance of this validation/usefulness criteria is essentially equivalent to saying that, if there is a high probability that if one molecule is active (or inactive), a second molecule is also active (or inactive), then most of the time sampling one of the pair will be sufficient. Restating this same principle with a slightly different emphasis highlights another feature, namely: the design criteria for combinatorial screening libraries should yield a high probability that, for any given inactive molecule, it is more probable to find an active molecule somewhere else rather than as a near neighbor of that inactive molecule. While this is a probabilistic approach, it emphasizes that a good approximation to a perfect metric is sufficient for purposes of designing a combinatorial screening library as well as in other situations where the ability to discriminate molecular structural difference and similarities is required. A perfect descriptor (certainty) for pharmacological searching is not needed to achieve the required level of confidence as long as it is valid (maps a subspace where biological properties cluster).

The typical prior art approach for establishing selection criteria for screening library subsets relied on the following clustering paradigm: 1) characterization of compounds according to a chosen descriptor(s) (metric[s]); 2) calculation of similarities or "distances" in the descriptor (metric) between all pairs of compounds; and 3) grouping or clustering of the compounds based on the descriptor distances. The idea behind the paradigm is that, within a cluster, compounds should have similar activities and, therefore, only one or a few compounds from each cluster, which will be representative of that cluster, need be included in a library. The actual clustering is done until the prior art user feels comfortable with the groupings and their spacing. However, with no knowledge of the validity/usefulness of the descriptor employed, and no guidance with respect to the size or spacing of clusters to be expected from any given descriptor, prior art clustering has been, at best, another intuitive "seat of the pants" approach to diversity measurement.

The prior art describes the construction and application of many molecular structural descriptors while all the while tacitly acknowledging that little progress has been made towards solving the fundamental problem of establishing their validity. The field has nevertheless proceeded based on the belief/faith that, by incorporating in the descriptors certain measures which had been recognized in QSAR studies as being important contributors to defining structure-activity relationships, valid/useful descriptors would be produced. In a leading method representative of this prior art approach to defining a similarity descriptor, E. Martin et al.[3] construct a metric for quantifying structural similarity using measures that characterize lipophilicity, shape and branching, chemical functionality, and receptor recognition features. (For the reasons set forth later in relation to the present invention, Martin et al. applied their metric to the reactants which would be used in combinatorial synthesis.) This large set of measures is used to generate a statistically blended metric consisting of a total of 16 properties for each individual reactant studied (5 shape descriptors, 5 measures of chemical functionality, 5 receptor binding descriptors, and one lipophilicity property). This generates a 16 dimensional property space. The 16 properties are simultaneously displayed in a circular "Flower Plots" graphical environment, where each property is assigned a petal. All the plots together visually display how the diversity of the studied reactants is distributed through the computed property space. Martin acknowledges that the plots ". . . cannot, of course, prove that the subset is diverse in any 'absolute' sense, independent of the calculated properties." (id. at 1434)***

In another approach relating to peptoid design, Martin et al.[4] have characterized the varieties of shape that an unknown receptor cavity might assume by a few assemblages of blocks, called "polyominos". Candidates for a combinatorial design are classified by the types of polyominos into which they can be made to fit, or "docked". The 7 flexible polyomino shape descriptors are added to the previously defined 16 descriptors to yield a 23 dimensional property space. Martin has demonstrated that the docking procedure generates for a methotrexate ligand in a cavity of dihydrofolate reductase nearly the correct structure as that established by X-ray diffraction studies. The docking procedure, which must be applied to every design candidate for each polyomino, requires a considerable amount of CPU time (is computationally expensive). However, a problem with this approach is the conceptually severe (unjustified) approximation of representing all possible irregularly shaped receptor cavities by only about a dozen assemblies of smooth-sided polyomino cubes. Martin has also presented no validation of the approach, which in this case, would be a demonstration that molecules which fit into the same polyominos tend to have similar biological properties.

One approach which has been taken to try to empirically assess the relative validity of prior art metrics has been to survey the metrics to see if any of them appeared to be superior to any others as judged by clustering analysis. Y. C. Martin et al.[5] have reported that 3D fingerprints, collections of fragments defined by pairs of atoms and their accessible interatomic distances, perform no better than collections of 2D fragments in defining clusters that separate biologically active from inactive compounds. As will be seen later, some of this work pointed towards the possible validity of one metric, but the authors concentrated on the comparative clustering aspects and did not follow up on the broader import of the data.

W. Herndon[6] among others has pointed out that an experimentally determined similarity QSAR is, by definition, a good test of the validity of that similarity concept for the biological system from which it is derived and may have some usefulness in estimating diversity for that system. However, QSARs essentially map only the space of a particular receptor, do not provide information about the validity of other descriptors, and would be generally inapplicable to construction of a combinatorial screening library designed for screening unknown receptors or those for which no QSAR data was available.

Finally, D. Chapman et al.[7] have used their "Compass" 3D-QSAR descriptor which is based on the three dimensional shape of molecules, the locations of polar functionalities on the molecules, and the fixation entropies of the molecules to estimate the similarity of molecules. Essentially, using the descriptor, they try to find the molecules which have the maximum overlap (in geometric/cartesian space) with each other. The shape of each molecule of a series is allowed to translate and rotate relative to each other molecule and the internal degrees of freedom are also allowed to rotate in an iterative procedure until the shapes with greatest or least overlap similarity are identified. Selecting 20 maximally diverse carboxylic acids based on seeking the maximally diverse alignment of each of the 3000 acids considered took approximately 4 CPU computing weeks by their method. No indication was given of whether their descriptor was valid in the sense defined above, and, clearly, such a procedure would be too time consuming to apply to a truly large combinatorial library design.

One way in which many of the prior art approaches attempt to work around the problem of not knowing if a molecular structural descriptor is valid is to try, when clustering, to maximize as much as possible the distance between the clusters from which compounds will be selected for inclusion in the screening library subset. The thinking behind this approach is that, if the clusters are far enough apart, only molecules diverse from each other will be chosen. Conversely, it is thought that, if the clusters are close together, oversampling (selection of two or more molecules representative of the same elements of diversity) would likely occur. However, as we have seen, if the metric used in the cluster analysis is not initially valid (does not define a subspace in which molecules with similar biological activity cluster), then no amount of manipulation will prevent the sample from being essentially random. Worse yet, an invalid metric might not yield a selection as good as random! The acknowledgement by Martin quoted above is a recognition of the prior art's failure to yet discover a general method for validating descriptors.

Another related problem in the prior art is the failure to have any objective manner of ascertaining when the library subset under design has an adequate number of members; that is, when to stop sampling. Clearly, if nothing is known about the distribution of the diversity of molecules, one arbitrary stopping point is as good as any other. Any stopping point may or may not sample sufficiently or may oversample. In fact, the prior art has not recognized a coherent quantitative methodology for determining the end point of selection. Essentially, in the prior art, a metric is used to maximize the presumed differences between molecules (typically in a clustering analysis), and a very large number of molecules are chosen for inclusion in a screening library subset based on the belief that there is safety in numbers; that sampling more molecules will result in sampling more of the diversity of a combinatorially accessible chemical space. As pointed out earlier, however, only by including all possible molecules in a library will one guarantee that all of the diversity has been sampled. Short of such total sampling, users of prior art library subsets constructed along the lines noted above do not know whether a random sample, a representative sample, or a highly skewed sample has been screened.

Several other problems flow from the inability to rationally select a combinatorial screening library for optimal diversity and these are related both to the chemistry used to create the combinatorial library and the screening systems used. First, because many more molecules may have to be synthesized than may be needed, mass synthetic schemes have to be devised which create many combinations simultaneously. In fact, there is a good deal of disagreement in the prior art as to whether compounds should be synthesized individually or collectively or in solution or on solid supports. Within any synthetic scheme, an additional problem is keeping track of and identifying the combinations created. It should be understood that, where relatively small (molecular weight of less than about 1500) organic molecules are concerned, generally standard, well known, organic reactions are used to create the molecules. In the case of peptide like molecules, standard methods of peptide synthesis are employed. Similarly for polysaccharides and other polymers, reaction schemes exist in the prior art which are well known and can be utilized. While the synthesis of any individual combinatorial molecule may be straightforward, much time and effort has been and is still being expended to develop synthetic schemes in which hundreds, thousands, or tens of thousands of combinatorial combinations can be synthesized simultaneously.

In many synthetic schemes, mixtures of combinatorial products are synthesized for screening in which the identity of each individual component is uncertain. Alternatively, many different combinatorial products may be mixed together for simultaneous screening. Each additional molecule added to a simultaneous screen means that many fewer individual screening operations have to be performed. Thus, it is not unusual that a single assay may be simultaneously tested against up to 625 or more different molecules. Not until the mixture shows some activity in the biological screening assay will an attempt be made to identify the components. Many approaches in the prior art therefore face "deconvolution" problems; ie. trying to figure out what was in an active mixture either by following the synthetic reaction pathway, by resynthesizing the individual molecules which should have resulted from the reaction pathway, or by direct analysis of duplicate samples. Some approaches even tag the carrier of each different molecule with a unique molecular identifier which can be read when necessary. All these problems are significantly decreased by designing a library for optimal diversity.

Another major problem with the inclusion of multiple and potentially non-diverse compounds in the same screening mixture is that many assays will yield false positives (have an activity detected above a certain established threshold) due to the combined effect of all the molecules in the screening mixture. The absence of the desired activity is only determined after expending the time, effort, and expense of identifying the molecules present in the mixture and testing them individually. Such instances of combined reactivity are reduced when the screening mixture can be selected from molecules belonging to diverse groups of an optimally designed library since it is not as likely that molecules of different (diversity) structures would likely produce a combined effect.

It is clear that a great deal of cleverness has been expended in actually manufacturing the combinatorial libraries. While the basic chemistry of synthesizing any given molecule is straight forward, the next advance in the development of combinatorial chemistry screening libraries will be optimization of the design of the libraries.

Further problems in the prior art arise in the attempt to follow up leads resulting from the screening process. As noted above, many libraries are designed with some knowledge of the receptor and its binding requirements. While, within those constraints, all possible combinatorial molecules are synthesized for screening, finding a few molecules with the desired activity among such a library yields no information about what active molecules might exist in the universe accessible with the same combinatorial chemistry but outside the limited (receptor) library definition. This is an especially troubling problem since, from serendipitous experience, it is well known that sometimes totally unexpected molecules with little or no obvious similarity to known active molecules exhibit significant activity in some biological systems. Thus, even finding a candidate lead in a library whose design was based on knowledge of the receptor is no guarantee that the lead can be followed to an optimal compound. Only a rationally designed combinatorial screening library of optimal diversity can approach this goal.

For prior art library subsets designed around the use of some descriptor to cluster compounds, similar problems may exist. In such a library design, one or at most a few compounds will have been selected from each cluster. Only if the descriptor is valid, does such a selection procedure make sense. If the descriptor is not valid, each cluster will contain molecules representative of many different diversities and selecting from each cluster will still have resulted in a random set of molecules which do not sample all of the diversity present. Since the prior art does not possess a generally applicable method of validating descriptors, all screening performed with prior art libraries is suspect and may not have yielded all the useful information desired about the larger chemical universe from which the library subsets were selected.

Finally, as the expense in time and effort of creating and screening combinatorial libraries increases, the question of the uniqueness of the libraries becomes ever more critical. Questions can be asked such as: 1) does library "one" cover the same diversity of chemical structures as library "two"; 2) if libraries "one" and "two" cover both different and identical aspects of diversity, how much overlap is there; 3) what about the possible overlap with libraries "three", "four", "five", etc.? To date, the prior art has been unable to answer these questions. In fact, assumptions have been made that as long as different chemistries were involved (ie., proteins, polysaccharides, small organic molecules), it was unlikely that the same diversity space was being sampled. However, such an assumption contradicts the well known reality that biological receptors can recognize molecular similarities arising from different structures. When screening for compounds possessing activity for undefined biological receptors, there is no way of telling a priori which chemistry or chemistries is most likely to produce molecules with activity for that receptor. Thus, screening with as many chemistries as possible is desired but is only really practical if redundant sampling of the same diversity space in each chemistry can be avoided. The prior art has not provided any guidance towards the resolution of these problems.

BRIEF SUMMARY OF THE INVENTION

In order to select a screening subset of a combinatorially accessible chemical universe which is representative of all the structural variation (diversity) to be found in the universe, it is necessary to have the means to describe and compare the molecular structural diversity in the universe. The first aspect of the present invention is the discovery of a generalized method of validating descriptors of molecular structural diversity. The method does not assume any prior knowledge of either the nature of the descriptor or of the biological system being studied and is generally applicable to all types of descriptors of molecular structure. This discovery enables several related advances to the art.

The second aspect of the invention is the discovery of a method of generating a validated three dimensional molecular structural descriptor using CoMFA fields. To generate these field descriptors required solving the alignment problem associated with these measurements. The alignment problem was solved using a topomeric procedure.

A third aspect of the invention is the discovery that validated molecular structural descriptors applicable to whole molecules can be used both to: 1) quantitatively define a meaningful end-point for selection in defining a single screening library (sampling procedure); and 2) merge libraries so as not to include molecules of the same or similar diversity. It is shown that a known metric (Tanimoto 2D fingerprint similarity) can be used in conjunction with the sampling procedure for this purpose.

A fourth aspect of the invention is the discovery of a method of using validated reactant and whole molecule molecular structural descriptors to rationally design a combinatorial screening library of optimal diversity. In particular, the shape sensitive topomeric CoMFA descriptor and the atom group Tanimoto 2D similarity descriptor may be used in the library design. As a benefit of designing a combinatorial screening library of optimal diversity based on validated molecular descriptors, many prior art problems associated with the synthesis, identification, and screening of mixtures of combinatorial molecules can be reduced or eliminated.

A fifth aspect of the invention is the use of validated molecular structural descriptors to guide the search for optimally active compounds after a lead compound has been identified by screening. In the case of a screening library designed for optimal diversity using validated descriptors, a great deal of the information necessary for lead optimization flows directly from the library design. In the case where a lead has been identified by screening a prior art library or through some other means, validated descriptors provide a method for identifying the molecular structural space nearest the lead which is most likely to contain compounds with the same or similar activity.

It is an object of this invention to define a general process which may be used with randomly selected literature data sets to validate molecular structural descriptors.

It is a further object of this invention to define a process to derive CoMFA steric fields (and, if desired, additional relevant fields) using topomeric alignment so that the resulting descriptor is valid.

It is a further object of this invention to teach that topomeric alignments may be used to describe molecular conformations.

It is a further object of this invention to define a general process for using a validated molecular descriptor to establish a meaningful end-point for the sampling of compounds thereby avoiding the oversampling of compounds representing the same molecular structural characteristics.

It is yet a further object of this invention to design an optimally diverse combinatorial screening library using multiple validated molecular structural descriptors.

It is a further object of this invention to use the topomeric CoMFA molecular structural descriptor as a reactant descriptor in the design of an optimally diverse combinatorial screening library.

It is a further object of this invention to use the Tanimoto 2D similarity molecular structural descriptor as a product descriptor in the design of an optimally diverse combinatorial screening library.

It is a further object of this invention to define a method for merging assemblies of molecules (libraries), both those designed by the methods of this invention and others not designed by the methods of this invention, in such a manner that molecules representing the same or similar diversity space are not likely to be included.

It is still a further object of this invention to define methods for the use of validated molecular structural descriptors to guide the search for optimally active compounds after a lead compound has been identified by screening or some other method.

These and further objects of the invention will become apparent from the detailed description of the invention which follows.

DESCRIPTION OF DRAWINGS

FIGS. 11A through 11C are schematic of the combinatorial screening library design process.

DETAILED DESCRIPTION OF THE INVENTION

Figure 1A:
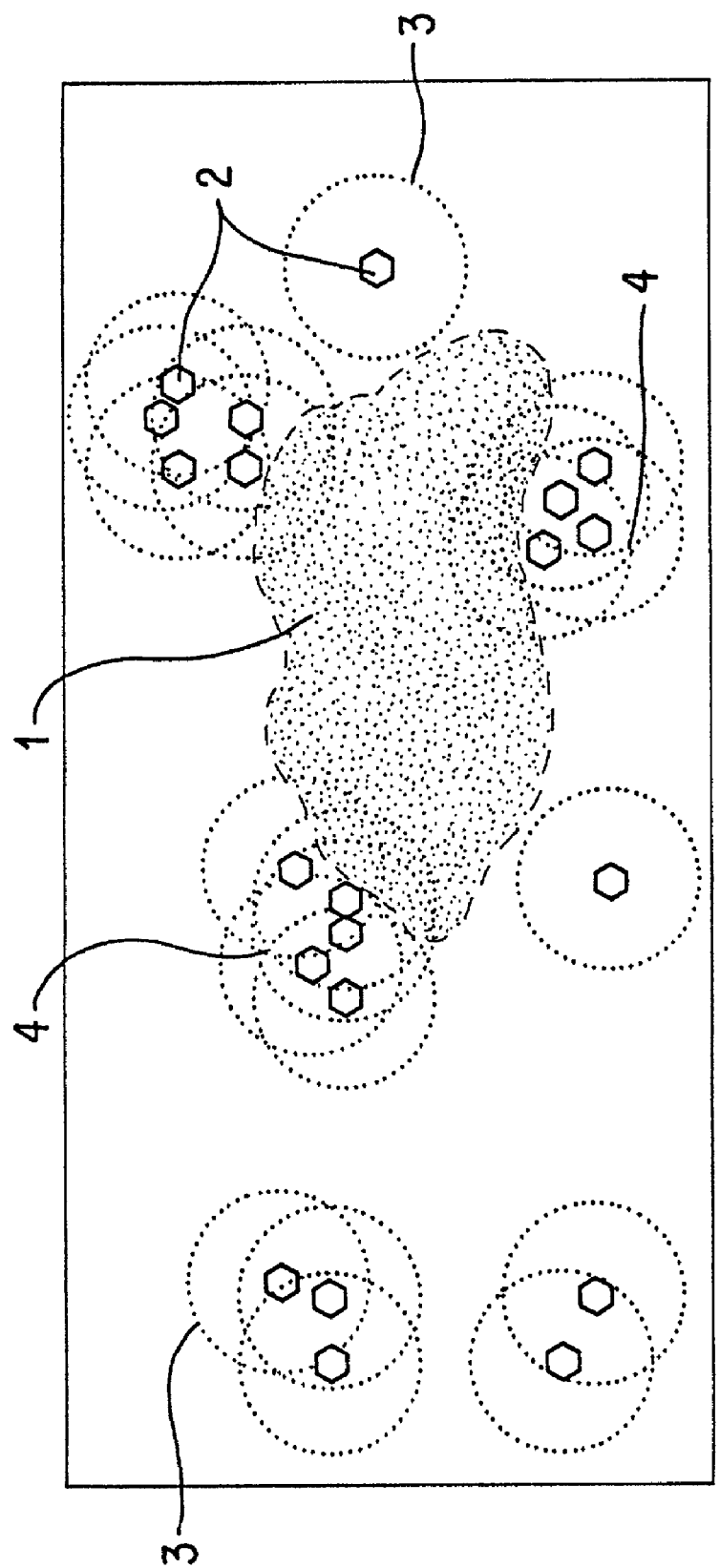
FIG. 1 schematically shows the distribution of molecular structures around and about an island of biological activity in a hypothetical two dimensional metric space for a poorly designed prior art library and for an efficiently designed optimally diverse screening library.

1. Computational Chemistry Environment
2. Definitions
3. Validating Metrics
   A. Theoretical Considerations—Neighborhood Property
   B. Construction, Application, and Analysis Of Patterson Plots
4. Topomeric CoMFA Descriptor
   A. Topomeric Alignment
   B. Calculation Of CoMFA and Hydrogen Bonding Fields
   C. Validation Of Topomeric CoMFA Descriptor
5. Tanimoto Fingerprint Descriptor
   A. Neighborhood Property
   B. Applicability Of Tanimoto To Different Biological Systems
   C. Comparison of Sigmoid and Patterson Plots
6. Comparison of Tanimoto and Topomeric CoMFA Metrics
7. Additional Validation Results
8. Combinatorial Library Design Utilizing Validated Metrics
   A. Removal Of Reactants For Non-Diversity Reasons
     i. General Removal Criteria
     ii. Biologically Based Criteria
   B. Removal of Non-Diverse Reactants
   C. Removal Of Products For Non-Diversity Reasons
   D. Removal of Non-Diverse Products
9. Lead Compound Optimization
   A. Advantages Resulting From Product Filter
   B. Advantages Resulting From Reactant Filter
   C. Identification (Building) Of Products
   D. Additional Optimization Methods Using Validated Metrics
10. Merging Libraries
11. Other Advantages of Optimally Diverse Libraries 1. Computational Chemistry Environment Generally, all calculations and analyses to conduct combinatorial chemistry screening library design and follow up are implemented in a modern computational chemistry environment using software designed to handle molecular structures and associated properties and operations. For purposes of this Application, such an environment is specifically referenced. In particular, the computational environment and capabilities of the SYBYL and UNITY software programs developed and marketed by Tripos, Inc. (St. Louis, Mo.) are specifically utilized. Unless otherwise noted, all software references and commands in the following text are references to functionalities contained in the SYBYL and UNITY software programs. Where a required functionality is not available in SYBYL or UNITY, the software code to implement that functionality is provided in an Appendix to this Application. Software with similar functionalities to SYBYL and UNITY are available from other sources, both commercial and non-commercial, well known to those in the art. A general purpose programmable digital computer with ample amounts of memory and hard disk storage is required for the implementation of this invention. In performing the methods of this invention, representations of thousands of molecules and molecular structures as well as other data may need to be stored simultaneously in the random access memory of the computer or in rapidly available permanent storage. The inventors use a Silicon Graphics, Inc. Challenge-M computer having a single 150 Mhz R4400 processor with 128 Mb memory and 4 Gb hard disk storage space.

2. Definitions:

The words or phrases in capital letters shall, for the purposes of this application, have the meanings set forth below:

2D MEASURES shall mean a molecular representation which does not include any terms which specifically incorporate information about the three dimensional features of the molecule. 2D is a misnomer used in the art and does not mean a geometric "two dimensional" descriptor such as a flat image on a piece of paper. Rather, 2D descriptors take no account of geometric features of a molecule but instead reflect only the properties which are derivable from its topology; that is, the network of atoms connected by bonds.

2D FINGERPRINTS shall mean a 2D molecular measure in which a bit in a data string is set corresponding to the occurrence of a given 2-7 atom fragment in that molecule. Typically, strings of roughly 900 to 2400 bits are used. A particular bit may be set by many different fragments.

COMBINATORIAL SCREENING LIBRARY shall mean a subset of molecules selected from a combinatorial accessible universe of molecules to be used for screening in an assay.

MOLECULAR STRUCTURAL DESCRIPTOR shall mean a quantitative representation of the physical and chemical properties determinative of the activity of a molecule. The term METRIC is synonymous with MOLECULAR STRUCTURAL DESCRIPTOR and is used interchangeably throughout this Application.

PATTERSON PLOTS shall mean two dimensional scatter plots in which the distance between molecules in some metric is plotted on the X axis and the absolute difference in some biological activity for the same molecules is plotted on the Y axis.

SIGMOID PLOTS shall mean two dimensional plots for which the proportion of molecular pairs in which the second molecule is also active is plotted on the Y axis and the pairwise Tanimoto similarity is plotted in intervals on the X axis.

TOPOMERIC ALIGNMENT shall mean conformer alignment based on a set of alignment rules.

3. Validating Metrics

A. Theoretical Considerations—Neighborhood Property

As noted above, the similarity principle suggests a way to quantify the concept of diversity by quantifying structural similarity. While the prior art devised many structural descriptors, no one has been able to explicitly show that any of the descriptors are valid. It is possible with the method of this invention to determine the validity of any metric by applying it to presently existing literature data sets, for which values of biological activity and molecular structure are known. Once the validity has been determined, the metric may be used with confidence in designing combinatorial screening libraries and in following up on discovered leads. Examples of these applications will be given below.

The present invention is the first to recognize that the similarity principle also provides a way to validate metrics. Specifically, the similarity principle requires that any valid descriptor must have a "neighborhood property". That is: the descriptor must meet the similarity principle's constraint that it measure the chemical universe in such a way that similar structures (as defined by the descriptor) have substantially similar biological properties. Or stated slightly differently: within some radius in descriptor space of any given molecule possessing some biological property, there should be a high probability that other molecules found within that radius will also have the same biological property. If a descriptor does not have the neighborhood property, it does not meet the similarity principle, and can not be valid. Regardless of the computations involved or the intentions of the users, using prior art descriptors without the neighborhood property results, at best, in random selection of compounds to include in screening libraries.

Figure 1B:
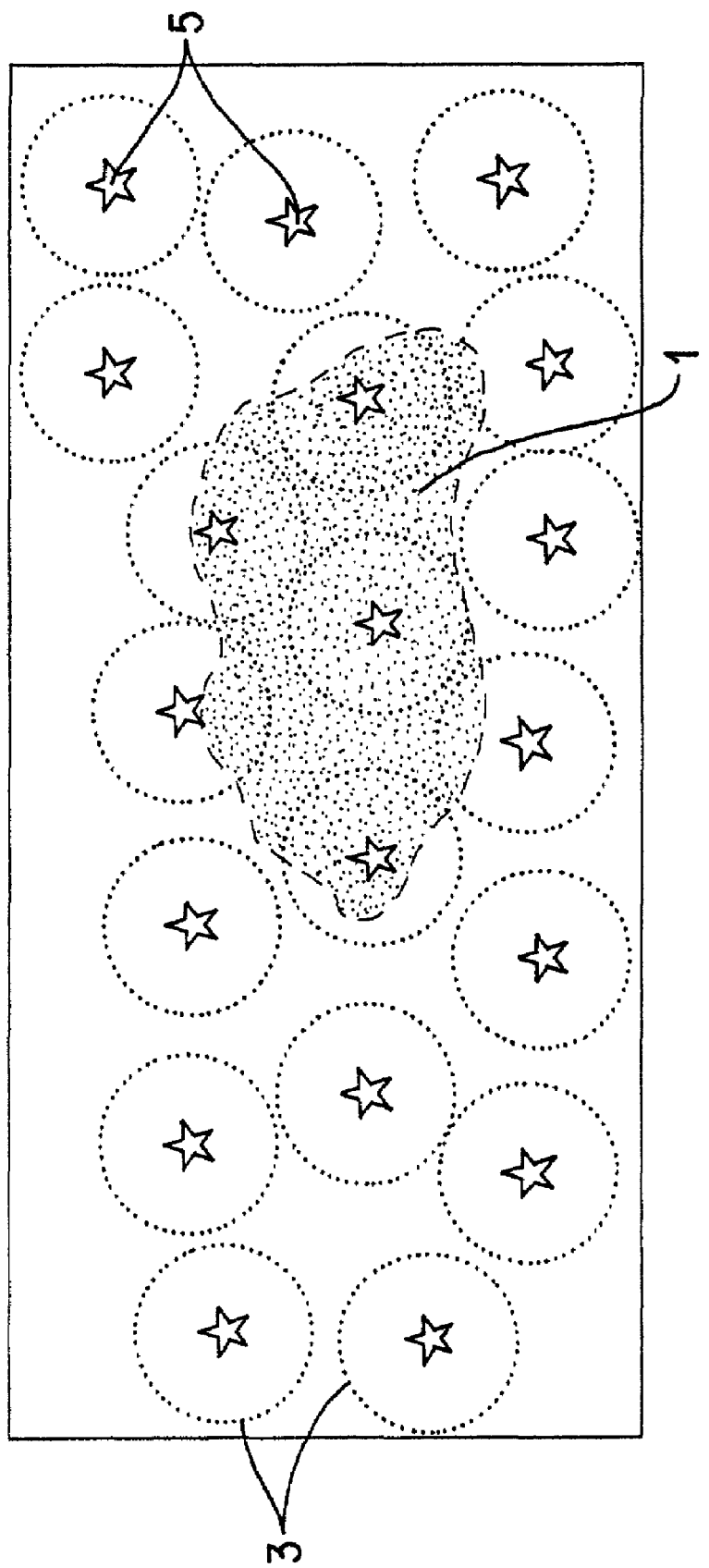

The importance of the neighborhood property to the design of combinatorial screening libraries is schematically illustrated in FIG. 1. FIG. 1A and FIG. 1B show an "island" 1 of biological activity plotted in some relevant two dimensional molecular descriptor space. In FIG. 1A the molecules 2 of a typical prior art library are plotted as hexagons. Around each hexagon a circle 3 describes the area of the metric space (the neighborhood) in which molecules of similar structural diversity to the plotted molecule would be found. Since the prior art metric used to select these molecules was not valid, the molecules are essentially distributed at random in the metric space. The circles 3 (neighborhoods) of similar structural diversity of several of the molecules overlap at 4 indicating that they sample the same diversity space. Clearly, there is no guarantee that the island area will be adequately sampled or that a great deal of redundant testing will not be involved with such a library design.

In FIG. 1B the molecules 5 of a optimally designed library are plotted as stars along with their corresponding circles 6 of similar structural diversity. Since a valid molecular descriptor with the neighborhood property was used to select the molecules, molecules were identified which not only sampled that part of the descriptor space accessible with the molecular structures available but also did not sample the same descriptor space more than once. Clearly, the likelihood of sampling the "island" 1 is greater when it is possible to identify the unique neighborhood 6 around each sample molecule and choose molecules that sample different areas. FIG. 1B represents an optimally diverse design.

A method to quantitatively analyze whether any given metric obeys the neighborhood principle has been discovered. In the prior art, absolute values of biological activity have always been considered the dependent variable with the structural metric as the independent variable. This is the case for traditional QSARs (quantitative structure activity relationships). Note however, that the similarity principle requires that for any pair of molecules, differences in activity are related to differences in structure. In particular, small differences in structure should be associated with small differences in activity. However, the converse is not necessarily true; large differences in activity are not necessarily associated with large differences in structure. The first novel feature of the present invention is that it uses differences in both measures: biological differences and structural (metric) differences. There is no rationale present in the prior art suggesting that the use of both differences in such a manner would be useful. Thus, instead of looking at the values assigned by the metric to each molecule, the absolute differences in the metric values for each pair of molecules are the independent variables and the absolute differences in biological activity for each pair of molecules are the dependent variables. The absolute value is used since it is the difference, not its sign, which is important.

Figure 2:
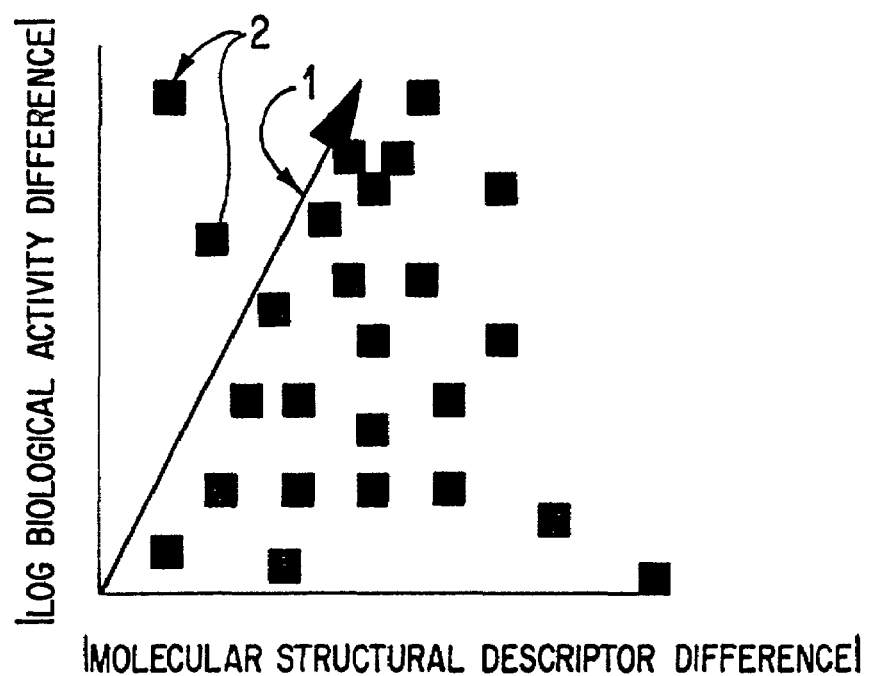
FIG. 2 shows a theoretical scatter plot (Patterson Plot) for a metric having the neighborhood property in which the X axis shows distances in some metric space calculated as the absolute value of the pairwise differences in some candidate molecular descriptor and the Y axis shows the absolute value of the pairwise differences in biological activity.

For a metric possessing the neighborhood property, a scatter plot of pairwise absolute differences in descriptors for each set of molecules versus pairwise absolute differences in biological activity for the same set of molecules (Patterson plot) will have a characteristic appearance as shown in FIG. 2. Note that it is important that pairwise absolute differences for all molecules in a data set are used, that is; the absolute metric "distance" between every molecule and every other molecule is plotted. Accordingly, there are n(n−1)/2 pairwise comparisons for every data set containing n compounds. The use of pairwise differences for every possible pair reflects all the relationships between all structural changes with all activity changes for the molecules under study.

Line 1 on the graph of FIG. 2 depicts a special case where there is a strictly linear relationship between differences in metric distance and differences in biological activity.

However, the neighborhood property does not imply a linear correlation (corresponding to points lying on a straight line) and need not imply anything about large property differences causing large biological activity differences. (Generally, the line should be linear for only very small changes in molecular structure and would exhibit a complex shape overall depending on the nature of the biological interaction. However, for purposes of discussion and analysis, it is useful to employ a straight line as a first approximation.) The slope of line 1 will vary depending on the biological activity of the measured system. Thus, the lower right trapezoid (LRT) {defined by the vertices [0,0], [actual metric value, max. bio. value], [max. metric value, max. bio. value], and [max. metric value, 0]} of the plot may be populated as shown in any number of ways.

The upper left triangle (ULT) of the plot (above the line) should not be populated at all as long as the descriptor completely characterizes the compound and there are no discontinuities in the behavior of the molecules. However, in the real world, some population of the space (as indicated by points 2) above the line would be expected since there are known discontinuities in the behavior of real molecular ligands. For instance, it is well known amongst medicinal chemists that adding one methyl group can cause some very active compounds to lose all sign of activity.

Figure 3:
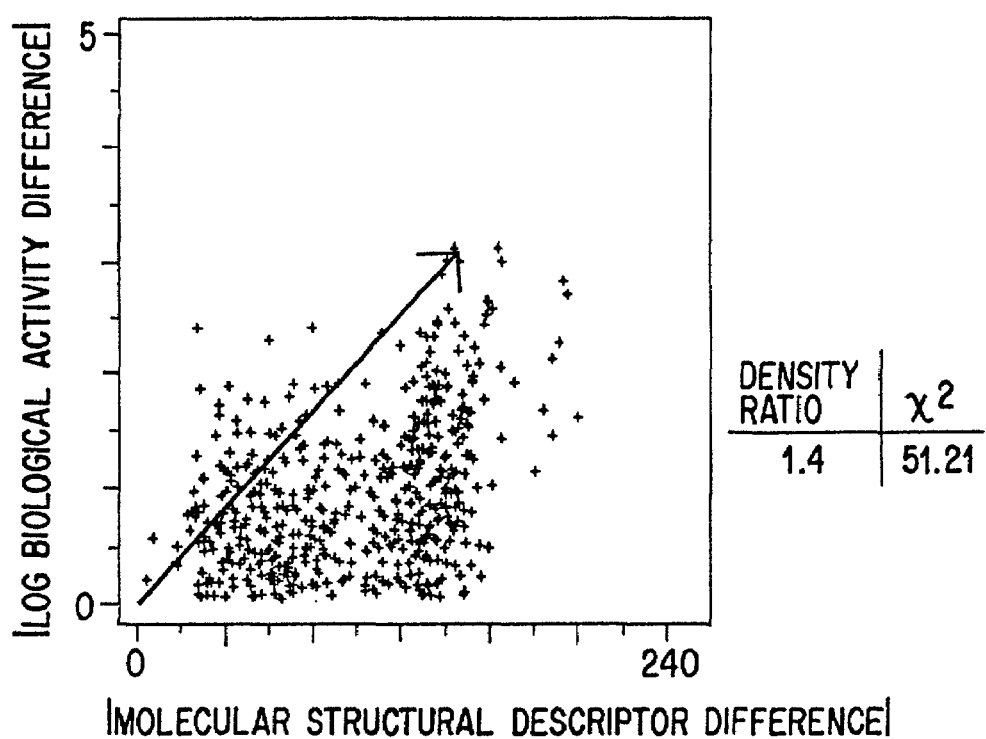
FIG. 3 shows a Patterson plot for an illustrative data set.

FIG. 3 shows a Patterson plot of a real world example. Points lying above the solid line near the Y axis reflect a metric space where a small difference in metric property (structure) produces a large difference in biological property. These points clearly violate the similarity principle/neighborhood rule. Thus, in the real world sometimes relatively small differences in structure can produce large differences in activity. If some points lie above the line, the metric is less ideal, but, clearly still useful. The major criteria and the key point to recognize is that for a metric to be valid the upper left triangle will be substantially less populated than the lower right trapezoid. Thus, it should be recognized that for any receptor, the presence of some particular side group or combination of side groups may produce a discontinuity in the receptor response.

Generally, however, any (metric) descriptor displaying the above characteristic of predominantly populating the lower right trapezoid (such as in FIG. 3) will possess the neighborhood property, and the demonstration that a metric possesses such behavior indicates the validity/usefulness of that metric. Conversely, a descriptor in which the points in the difference plot are uniformly distributed (equal density of points in ULT and LRT) does not obey the neighborhood principle and is invalid as a metric. While a brief glance at the difference plots may quickly indicate validity or non-validity, visual analysis may be misleading. As it turns out, data points in the plot frequently overlap so that visually only one point is seen where there may be two (or more). A quantitative analysis of the data distribution, therefore, yields a more accurate picture. An objective validation procedure for determining the validity/usefulness of metrics from Patterson plots of real world data including a method for assessing its statistical significance is set forth below.

Viewing the metric data in this way requires no knowledge about either the actual value of the biological activities or the actual values assigned by the descriptor under review. Because all pairwise differences are displayed, all possible gradations of molecular structural diversity and activity are represented and utilized. Consequently, there is no arbitrary lower limit set on the usable data.

B. Construction, Application, and Analysis of Patterson Plots

For purposes of objectively examining metrics for validity, it is first necessary to accurately determine the slope (placement) of the line which divides a Patterson plot into the two areas, a lower right trapezoid (LRT) and an upper left triangle (ULT). The triangle is defined by the points [0, 0], [actual metric value, max. bio. value], and [0, max. bio. value]. The trapezoid is defined by the points [0,0], [actual metric value, max. bio. value], [max. metric value, max. bio. value], and [max. metric value, 0]. For a metric to be a valid and a useful measure of molecular diversity, the density of points in the lower right trapezoid should be significantly greater than the density in the upper left triangle. To determine the correct placement of the line, the variation in the density of points is used. The line must always pass through (0,0) at the lower left corner of a Patterson plot since no change in any metric must imply no change in the biological activity. As noted earlier, considering a straight line is only a first approximation. A "perfect" metric, which totally describes the structure activity relationship of the biological system, would display a complex line reflecting the biological interaction. As a first approximation, a "useful" straight line can be found which meaningfully reflects the variation in the density of points.

The preferred search for the correct/useful line tests only those slopes which a particular data set can distinguish; specifically those drawn from [0,0] to each point [actual metric value, max bio value]. The process starts by drawing the line to a point having the smallest actual metric value [smallest metric value, max. bio. value] and continues for all of the values observed for actual metric value up to the largest [largest metric value, max. bio. value]; ie, subsequent lines are of decreasing slope. (In the limiting case of drawing the line to [largest metric value, max. bio. value] the trapezoid becomes a triangle.) When searching for the correct diagonal, it is defined to be the one which yields the highest density (number of data points/unit graph area) for a lower right triangle, which for this process is defined to have its vertices at [0, 0], [actual metric value, 0], and [actual metric value, max bio. value]. Thus, the line is identified based on the density of points under this triangle, but the evaluation ratios for the metric are calculated based on the density within the trapezoid compared to the density of the entire plot (sum of triangle and trapezoid areas). The software necessary to implement this procedure (as well as to determine the $X^2$ values to be discussed below) is contained in Appendix "A". There may be other procedures for determining the placement of the line since the line is only a first approximation. Any such procedure must meet two tests: 1) it must consistently distinguish between diversity descriptors; and 2) it must clearly distinguish/recognize meaningless diversity descriptors. The procedure described here clearly meets both tests. (The preferred search for the placement of the line is as described above. However, the lines shown in the Figures accompanying this description were found slightly differently. For the Figures, the search was started by requiring that the diagonal also pass through the point defined by the largest descriptor difference and the maximum biological activity difference [max.metric value, max. bio. value]. The line was then systematically tilted towards the vertical trying each of 100 evenly spaced steps (in terms of the Y/X ratio). As in the preferred method, the line yielding the highest density for the LRT was drawn. The line placements yielded by the two methods are not substantially different. All numerical values reported in this specification were obtained from Patterson plots in which the preferred line drawing process was used.)

Figure 4:
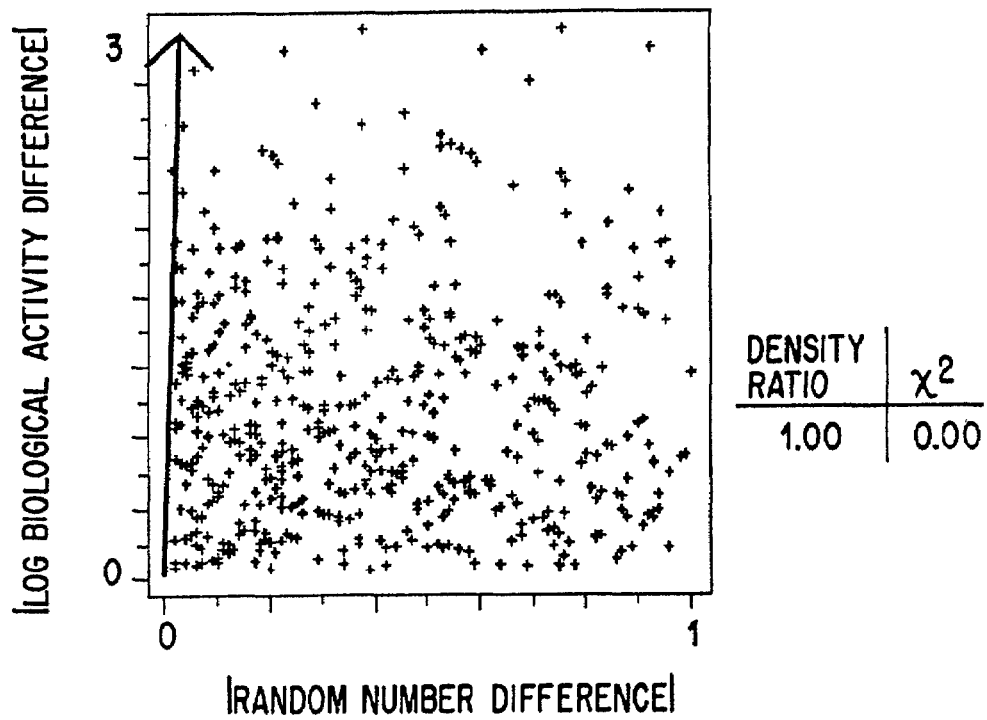
FIG. 4 shows a Patterson plot for the same data set as in FIG. 3 but where the diversity descriptor values (X axis) associated with each molecule have been replaced by random numbers.
Figure 5:
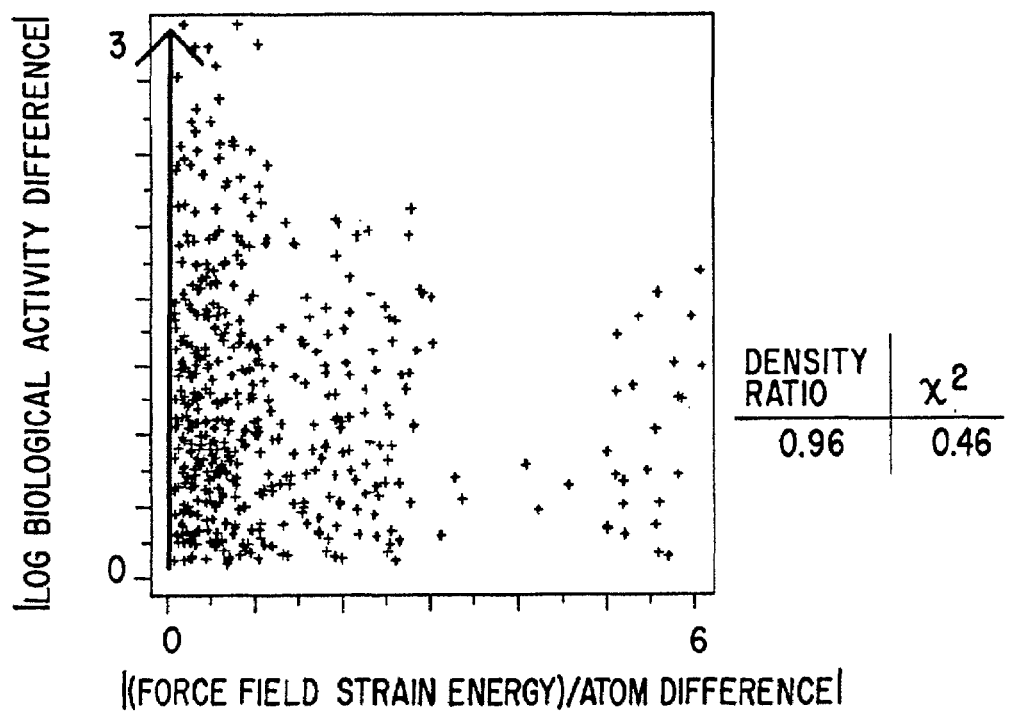
FIG. 5 shows a Patterson plot for the same data set as in FIG. 3 but where the diversity descriptor values (X axis) associated with each molecule have been replaced by a normalized force field strain energy/atom value.

The Patterson plot showing the diagonal for an exemplary data set used to validate the topomeric CoMFA descriptor (discussed in Section 4.C. below) is shown in FIG. 3. For comparison, FIGS. 4 and 5 show Patterson plots for two other variations of the same data which would not be expected to be valid molecular "measurements" useful as diversity metrics. For FIG. 4, in place of the actual metric values of FIG. 3, random numbers were generated for the diversity descriptor values of each compound and the Patterson plot generated from the all differences in these random numbers. As expected from a random number assignment, no line can be found by the procedure which enriches the density in the triangle and the best ratio is not significantly different from 1.0. The best line is always reported by the procedure, which in this case corresponds to a nearly vertical line drawn to the point [minimum metric value, max. bio. value]. For randomly distributed values, this line yields the highest density for the test triangle since the X axis value and, therefore, the area of the tested triangle, is at a minimum. It is possible with some random data sets that this line, although nearly vertical, might include a couple points under the line. The placement of the line at this position is essentially an artifact of the procedure which results from an inability to find any other line which enriches the density in the tested triangle.

Because random numbers are not "real" metrics, an example of a "real molecular measurement" that is unlikely to be a valid diversity metric was examined. For the Patterson plot of FIG. 5, a force field strain energy (for the topomeric conformations using the standard Tripos force field) was calculated for each of the compounds in the same data set as was used for FIGS. 3 and 4. Because force field strain energy tends to increase with the number of atoms and thus, correlate roughly with the occasionally useful molecular weight, to normalize the value, the force field energy was divided by the number of atoms in each molecule. As expected, just as with random numbers, no optimum line could be found. This is essentially a confirmation that the points in the graph were also distributed randomly. Again, the best ratio is not significantly different from 1.0.

To objectively quantify the validity/usefulness determination, the ratio of the density of points in the lower right trapezoid to the average density of points is determined. This value can vary from somewhere above 0 but significantly less than 1, through 1 (equal density of points in each area) to a maximum of 2 (all the points in the lower right trapezoid, and the upper triangle and lower trapezoid are equal in area [limiting case of trapezoid merging into triangle]). According to the theoretical considerations discussed above, a ratio very near or equal to 1 (approximately equal densities) would indicate an invalid metric, while a ratio (significantly) greater than 1 would indicate a valid metric. The value of this ratio is set forth next to each Patterson plot in FIGS. 3 (real data), 4 (random numbers substituted), and 5 (force field energy substituted) under the column "Density Ratio". Clearly, the topomeric CoMFA data of FIG. 3 reflect a valid metric (ratio much larger than 1), while the random numbers of FIG. 4 and force field energies of FIG. 5 reflect a meaningless invalid metric (ratio very near 1). As will be discussed below, a density ratio of 1.1 is a useful threshold of validity/usefulness for a molecular diversity descriptor.

The statistical significance of the Patterson plot data can also be determined by a chi-squared test at any chosen level of significance. In this case the data are handled as: The chi-squared values for the Patterson plots of FIGS. 3, 4, and 5 are also set forth next to $$X^2 = \frac{(\text{Actual } LRT \text{ Count} - \text{Expected } LRT \text{ Count})^2}{\text{Expected } LRT \text{ Count}}$$

$$\text{where: Expected } LRT \text{ Count} = \frac{LRT \text{ Area}}{\text{Total Area}} \times \text{Total Count}$$

the plots under the column $X^2$. For 95% confidence limits and one degree of freedom, the chi-squared value is 3.84. The chi-squared values confirm the visual inspection and density ratio observations that the CoMFA metric is valid and the other two "constructed" metrics are invalid. A full set of topomeric CoMFA, random number, and force field data are discussed below under validation of the topomeric CoMFA descriptor.

The analysis of metrics using the difference plot of this invention is a powerful tool with which to examine metrics and data sets. First, the analysis can be used with any system and requires no prior assumptions about the range of activities or structures which need to be considered. Second, the plot extracts all the information available from a given data set since pairwise differences between all molecules are used. The prior art believed that not much information, if any, could be extracted from literature data sets since, generally, there is not a great deal of structural variety in each set. On the contrary, as will be shown below, using the Patterson plot method of this invention, a metric can be validated based on just such a limited data set. As will also be demonstrated below, metrics can be applied to literature data sets to determine the validity of the metrics. This ability opens up vast amounts of pre-existing literature data for analysis. Since in any analysis there is always a risk of making an improper determination due to sampling error when too few data sets are used or too narrow a variety of biological systems (activities) are included, the ability to use much of the available literature is a significant advance in the art. Also, the fact that the validation analysis methodology of this invention is not dependent on the study of a specific biological system, strongly implies that a validated metric is very likely to be applicable to molecular structures of unknown biological activity encountered in designing combinatorial screening libraries or making other diversity based selections. Or stated slightly differently, there is a high degree of confidence that metrics validated across many chemistries and biologies can be used in situations where nothing is known about the biological system under study.

4. Topomeric CoMFA Descriptor

Many of the prior art descriptors are essentially 2D in nature. That this is the case with the prior art probably reflects three underlying reasons. First, the rough general associations between fragments and biological properties were validated statistically decades ago.[8] Second, 2D fragment keys or "fingerprints" are widely available since they are used by all commercial molecular database programs to compare structures and expedite retrieval. Third, no one in the prior art has yet met the challenge of figuring out how to formulate and validate an appropriate three dimensional molecular structural descriptor. The situation in the prior art before the present invention is very similar to the field of QSAR about ten years ago. Then, the prior art had long recognized the desirability of three dimensional descriptors but had not been able to implement any. When a 3D technique (CoMFA) became available[9], its widespread acceptance[10] and application[11] confirmed the expected importance of 3D descriptors in general.

It has been discovered that a CoMFA approach to generating a molecular structural descriptor using a specially developed alignment procedure, topomeric alignment, produces a three dimensional descriptor of molecules which is shown to be valid by the method outlined above. In addition, this new descriptor provides a powerful tool with which to design combinatorial screening libraries. It is equally useful any time selection based on diversity from within a congeneric series is required. A full description of CoMFA and the generation of molecular interaction energies is contained in U.S. Pat. Nos. 5,025,388 and 5,307,287. The disclosures of these patents are incorporated in this Application. The usual challenge in applying CoMFA to a known set of molecules is to determine the proper alignment of the molecular structures with respect to each other. Two molecules of identical structure will have substantially different molecular interaction energies if they are translated or rotated so as to move their atoms a more than about 4 Å from their original positions. Thus, alignment is hard enough when applying CoMFA to analyze a set of molecules which interact with the same biological receptor. The more difficult question is how to "align" molecules distributed in multi-dimensional chemistry space to create a meaningful descriptor with respect to arbitrary and unknown receptors against which the molecules will ultimately be tested. The topomeric alignment procedure was developed to correct the usual CoMFA alignments which often over-emphasize a search for "receptor-bound", "minimum energy", or "field-fit" conformations. It has been discovered that, when congenericity exists, a meaningful alignment results from overlaying the atoms that lie within some selected common substructure and arranging the other atoms according to a unique canonical rule with any resulting steric collisions ignored. When CoMFA fields are generated for molecules so aligned, it has been discovered that the resulting field differences are a valid molecular structural descriptor.

Two major advantages are achieved by applying the topomeric CoMFA metric to the reactants proposed for use in a combinatorial synthesis rather than the products resulting from the synthesis. First, the computational time/effort is dramatically reduced. Instead of analyzing for diversity a combinatorial matrix of product compounds (R1×R2×R3 . . . ) only the values for the sum of the reactants (R1+R2+R3 . . . ) need to be computed. For example, assuming 2000 reactants for R1 and 2000 reactants for R2, only 4000 calculations need be performed on the reactants versus $2000^2$ (4,000,000) if calculations on the combinatorial products were performed. Second, by identifying reactants which explore similar diversity space, it is only necessary to choose one of each reactant representative of each diversity. This immediately reduces the number of combinatorial products which need to be considered and synthesized.

A. Topomeric Alignment

Usually a CoMFA modeler seeks low energy conformations. However, if alignment with unknown receptors is desired (such as is the case in designing combinatorial screening libraries for general purpose screening), then the major goal in conformer generation must be that molecules having similar topologies should produce similar fields. In fact, topomeric CoMFA fields may be used as a validated diversity descriptor to identify molecules with similar or dissimilar structures anytime there is a problem of having more compounds than can be easily dealt with. Thus, its applicability extends well beyond its use in combinatorial chemistry to all situations where it is necessary to analyze an existing group of compounds or specify the creation of new ones. The topomeric alignment procedure is especially applicable to the design of a combinatorial screening library. Typically, as noted earlier, in the creation of combinatorially derived compounds there is often an invariant central core to which a variety of side chains (contributed by reactants of a particular class) are attached at the open valences. Within the combinatorial products, this central core tethers each of the side chains contributed by any set of reactants into the same relative position in space. In the language of CoMFA alignments, the side chains contributed by each reactant can thus be oriented by overlapping the bond that attaches the side chain to the central core and using a topomeric protocol to select a representative conformation of the side chain. Nowhere does the prior art suggest that a topomeric protocol could possibly yield a meaningful alignment. Indeed, the prior art inherently teaches away from the idea because the topomerically derived conformers often may be energetically inaccessible and incapable of binding to any receptor.

The idea of a topomeric conformer is that it is rule based. The exact rules may be modified for specific circumstances. In fact, once it is appreciated from the teaching of this invention that a particular topomeric protocol is useful (yields a valid molecular descriptor), other such protocols may be designed and their use is considered within the teaching of this disclosure.

The following topologically-based rules will generate a single, consistent, unambiguous, aligned topomeric conformation for any molecule lacking chiral atoms. The software necessary to implement this procedure is contained in Appendix "A". The starting point for a topomeric alignment of a molecule is a CONCORD generated three dimensional model which is then FIT as a rigid body onto a template 3D model by least-squares minimization of the distances between structurally corresponding atoms. By convention, the template model is originally oriented so that one of its atoms is at the Cartesian origin, a second lies along the X axis, and a third lies in the XY plane.

Torsions are then adjusted for all bonds which: 1) are single and acyclic; 2) connect polyvalent atoms; and 3) do not connect atoms that are polyvalent within the template model structure since adjusting such bonds would change the template-matching geometry. Unambiguous specification of a torsion angle about a bond also requires a direction along that bond and two attached atoms. In this situation, for acyclic bonds the direction "away from the FIT atoms" is always well-defined.

The following precedence rules then determine the two attached atoms. From each candidate atom, begin growing a "path", atom layer by atom layer, including all branches but ending whenever another path is encountered (occurrence of ring closure). At the end of the bond that is closer to the FIT atoms, choose the attached atom beginning the shortest path to any FIT atom. If there are several ways to choose the atom, first choose the atom with the lowest X. If there are still several ways to choose the atom, choose next the atom with the lowest Y, and finally, if necessary, the lowest Z coordinate (coordinate values differing by some small value, typically less than 0.1 Angstroms, are considered as identical). At the other end of the bond, choose the atom beginning the path that contains any ring. When more than one path contains a ring, choose the atom whose path has the most atoms. If there are several ways to choose the path, in precedence order choose the path with the highest sum of atomic weights, and finally, if still necessary, the atom with the highest X, then highest Y, then highest Z coordinate. The new setting of the torsional value depends only on whether the bonds to the chosen atoms are cyclic or not. If neither are cyclic, the setting is 180 degrees; if one is cyclic, the setting is 90 degrees; and if both are cyclic, the setting is 60 degrees. Any steric clashes that may result from these settings are ignored.

Figure 6A:
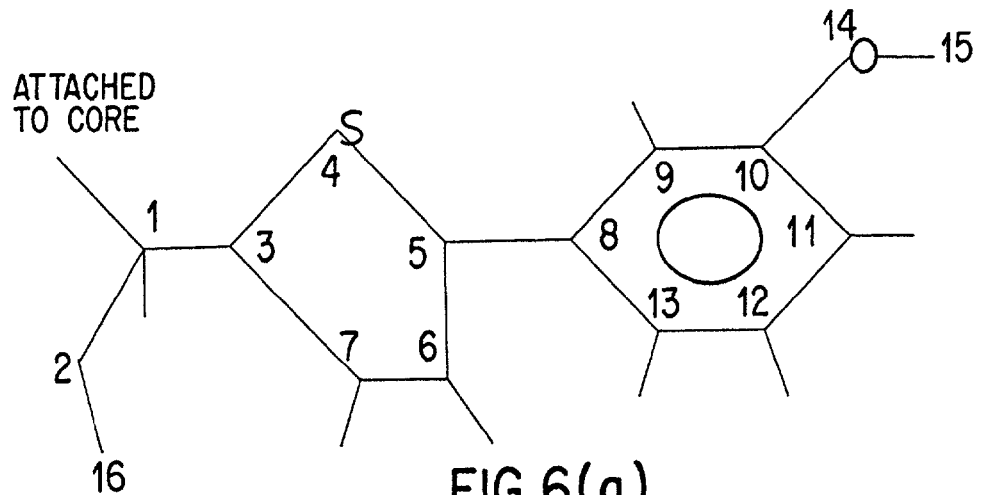
FIGS. 6A through 6C show three molecular structures numbered and marked in accordance with the topomeric alignment rule.

As an illustrative example, consider generation of the topomeric conformer for the side chain shown in FIG. 6(A), in which atom 1 is attached to some core structure by the upper left-most bond. Assuming that the alignment template for this fragment involves atom 1 only, there are three bonds whose torsions require adjustment, those connecting atoms pairs 1-3; 5-8; and 10-14. (Addin atom 3 to the alignment template would make atom 1 "polyvalent within the template model structure", so that the 1-3 bond would then not be altered.) The atom whose attached atoms will move (in the torsion adjustment) is the second atom noted in each atom pair. For example, if a torsional change were applied to the 14-10 bond instead of the 10-14 bond as shown in FIG. 6A, all of the molecule except atoms 10, 14 and 15 (and 13 by symmetry) would move. Correspondingly, if a torsional change were applied to the 10-14 bond instead of the 14-10 bond, only atom 15 would move.

Figure 6B:
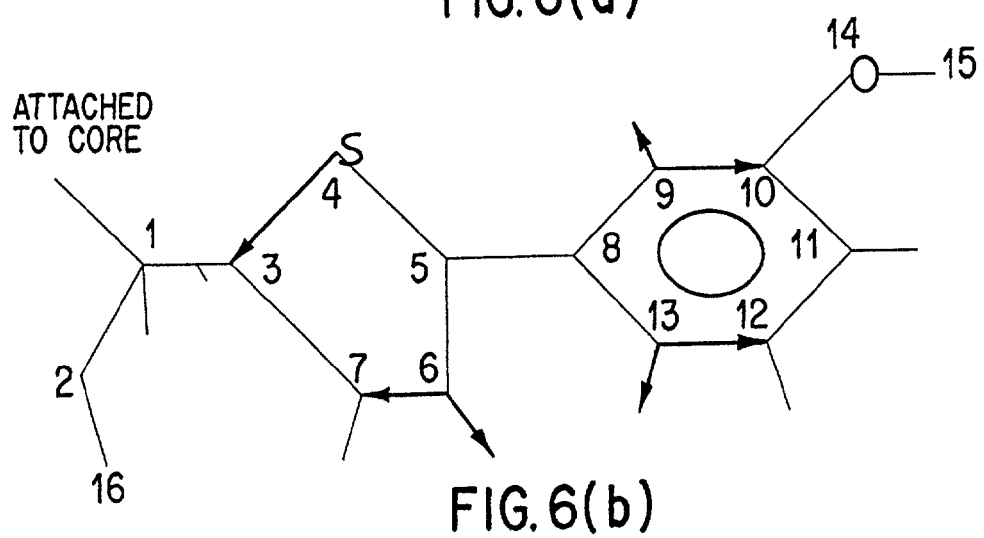
Figure 6C:
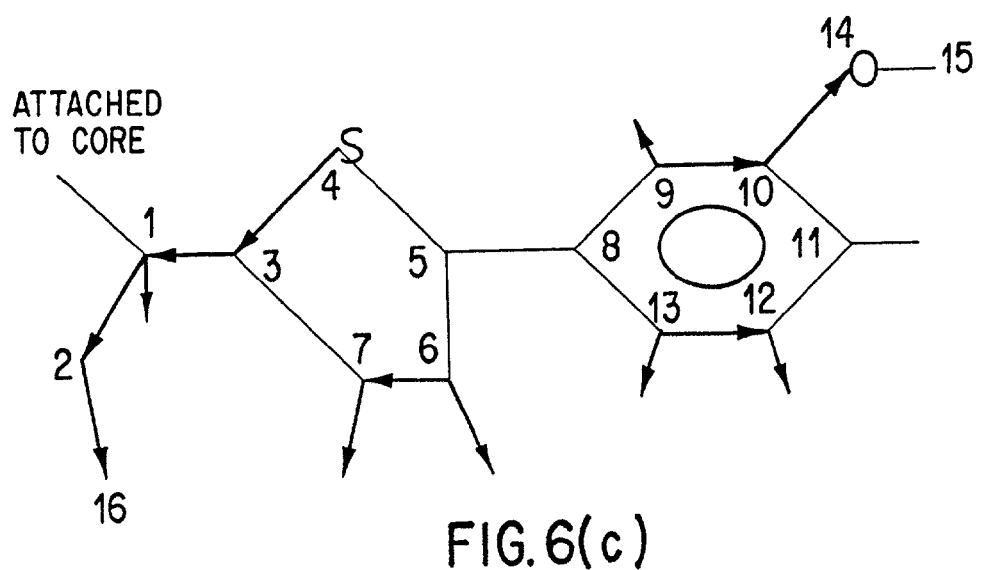

To define a torsional change, atoms attached to each of the bonded atoms must also be specified. For example, setting torsion about the bond 5-8 to 60 degrees would yield four different conformers depending on whether it is the 6-5-8-13, 6-5-8-9, 4-5-8-9, or 4-5-8-13 dihedral angle which becomes 60 degrees. To make such a choice, "paths" are grown from each of the candidate atoms, in "layers", each layer consisting of all previously unvisited atoms attached to any existing atom in any path. In choosing among the four attached-atom possibilities of the 5-8 bond, FIG. 6(B) shows the four paths after the first layer of each is grown, and FIG. 6(C) shows the final paths. In FIG. 6(C), notice within the rings that, not only is the bond between 3 and 7 not crossed, but also atom 11 is not visited because the third layer seeks to include 11 from two paths, so both fail. The attached atoms chosen for the torsion definition becomes the ones that begin the highest-ranking paths according to the rules stated above. For example, in FIG. 6(C), attached atom 4 outranks atom 6 because its path is the only one reaching the alignment template, and atom 9 outranks atom 13 because its path has more atoms, so that it is the 4-5-8-9 torsion which is set to a prescribed value. For the same reasons, the other complete torsions become 9-10-14-15, attached 1-3-4 and attached 1-2-16. The other decision rules would need to be applied if atom 9 was, instead of carbon, an aromatic nitrogen (with the consequent loss of the attached hydrogen) so that the 9 and 13 paths have the same number of atoms. In this case, the 9 path still takes priority, since it has the higher molecular weight. If instead atom 14 is deleted, so that the 9 and 13 paths are topologically identical, the 9 path again takes priority because atom 9 has the same X coordinate but a larger Y coordinate than does atom 13.

As for the dihedral angle values themselves, torsion 4-5-8-9 is set to 60 degrees, because both the 4-5 and 8-9 bonds are within a ring; torsions 9-10-14-15 and attached-1-3-4 become 90°, because only the 3-4 and 9-10 bonds respectively are cyclic; and the attached-1-2-16 dihedral becomes 180° since none of the bonds are cyclic. It should be noted that this topomeric alignment procedure will not work with molecules containing chiral centers since, for each chiral center, two possible three dimensional configurations are possible for the same molecule, and, clearly, each configuration by the above rules would yield a different topomeric conformer.

However, the critical point is that the use of a single topomerically aligned conformer in computing a CoMFA three dimensional descriptor has been found to yield a validated descriptor. While other approaches to conformer selection such as averaging many representative conformers or classifying a representative set by their possible interactions with a theoretically averaged receptor (such as in the polyomino docking) are possible, it has been found that topomerically aligned conformers yield a validated descriptor which, as will be seen below, produces clustering highly consistent with the accumulated wisdom of medicinal chemistry.

B. Calculation Of CoMFA and Hydrogen Bonding Fields

The basic CoMFA methodology provides for the calculation of both steric and electrostatic fields. It has been found up to the present point in time that using only the steric fields yields a better diversity descriptor than a combination of steric and electrostatic fields. There appear to be three factors responsible for this observation. First is the fact that steric interactions—classical bioisosterism—are certainly the best defined and probably the most important of the selective non-covalent interactions responsible for biological activity. Second, adding the electrostatic interaction energies may not add much more information since the differences in electrostatic fields are not independent of the differences in steric fields. Third, the addition of the electrostatic fields will halve the contribution of the steric field to the differences between one shape and another. This will dilute out the steric contribution and also dilute the neighborhood property. Clearly, reducing the importance of a primary descriptor is not a way to increase accuracy. However, it is certainly possible that in a given special situation the electrostatic contribution might contribute significantly to the overall "shape". Under these unique circumstances, it would be appropriate to also use the electrostatic interaction energies or other molecular characterizers, and such are considered within the scope of this disclosure. For instance, in some circumstances a topomeric CoMFA field which incorporates hydrogen bonding interactions, characterized as set forth below, may be useful.

The steric fields of the topomerically aligned molecular side chain reactants are generated almost exactly as in a standard CoMFA analysis using an $sp^3$ carbon atom as the probe. As in standard CoMFA, both the grid spacing and the size of the lattice space for which data points are calculated will depend on the size of the molecule and the resolution desired. The steric fields are set at a cutoff value (maximum value) as in standard CoMFA for lattice points whose total steric interaction with any side-chain atom(s) is greater than the cutoff value. One difference from the usual CoMFA procedure is that atoms which are separated from any template-matching atom by one or more rotatable bonds are set to make reduced contributions to the overall steric field. An attenuation factor (1–"small number"), preferably about 0.85, is applied to the steric field contributions which result from these atoms. For atoms at the end of a long molecule, the attenuation factor produces very small field contributions (ie: $[0.85]^N$) where N is the number of rotatable bonds between the specified atom and the alignment template atom. This attenuation factor is applied in recognition of the fact that the rotation of the atoms provides for a flexibility of the molecule which permits the parts of the molecule furthest away from the point of attachment to assume whatever orientation may be imposed by the unknown receptor. If such atoms were weighted equally, the contributions to the fields of the significant steric differences due to the more anchored atoms (whose disposition in the volume defined by the receptor site is most critical) would be overshadowed by the effects of these flexible atoms.

The derivation of a hydrogen-bond field is slightly different from the standard CoMFA measurement. The intent of the hydrogen-bonding descriptor is to characterize similarities and differences in the abilities of side chains to form hydrogen-bonds with unknown receptors. Like the successful use of the topomeric conformation to characterize steric interactions, the topomeric conformation is also an appropriate way to characterize the spatial position of a side chain's hydrogen-bonding groups. However, unlike a steric field, hydrogen-bonding is a spatially localized phenomenon whose strength is also difficult to quantitate. Therefore, it is appropriate to represent a hydrogen-bonding field as a bitset, much like a 2D fingerprint, or as an array of 0 or 1 values rather than as an array of real numbers like a CoMFA field.

The hydrogen-bonding loci for a particular side chain are specified using the DISCO approach of "extension points" developed by Y. Martin[12] and coworkers, wherein, for example, a carbonyl oxygen generates two hydrogen-bond accepting loci at positions found by extending a line passing from the oxygen nuclei through each of the two "lone-pair" locations to where a complementary hydrogen-bond donating atom on the receptor would optimally be. It is not possible with a bitset representation to attenuate the effects of atoms by the number of intervening rotatable bonds. Instead, uncertainty about the location of a hydrogen-bonding group can be represented by setting additional bits for grid locations spatially adjacent to the single grid location that is initially set for each hydrogen-bonding locus. In other words, each hydrogen-bonding locus sets bits corresponding to a cube of grid points rather than a single grid point. The validation results shown in Table 4 were obtained for a cube of 27 grid locations for each hydrogen bonding locus. The single bitset representing a topomeric hydrogen-bonding fingerprint has twice as many bits as there are lattice points, in order to discriminate hydrogen-bond accepting and hydrogen bond-donating loci. The difference between two topomeric hydrogen-bonding fingerprints is simply their Tanimoto coefficient which now represents a difference in actual field values. Software which implements the hydrogen-bonding field calculations is provided in Appendix "B".

C. Validation Of Topomeric CoMFA Descriptor

Figure 7A:
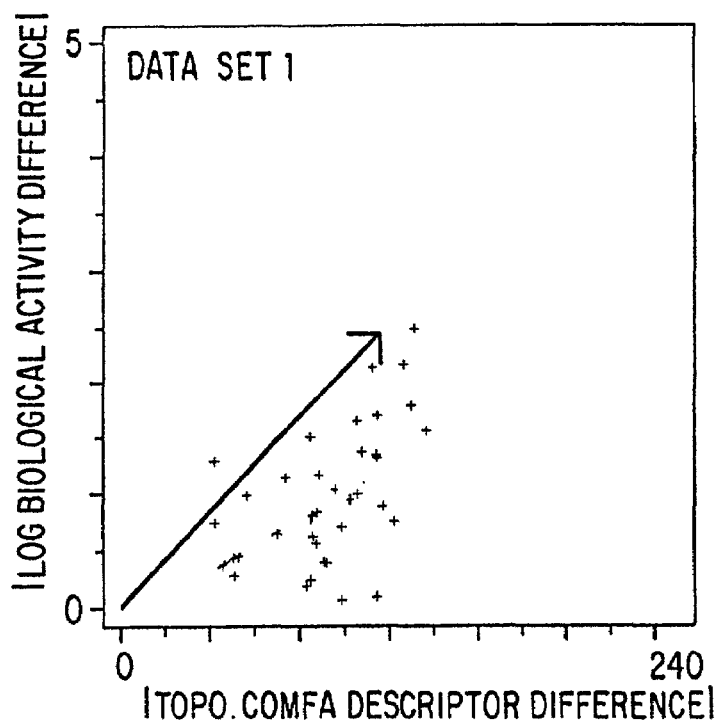
FIGS. 7(a) through 7(t) are a complete set of Patterson plots for the twenty data sets used for the validation studies of the topomeric CoMFA descriptor.
Figure 7B:
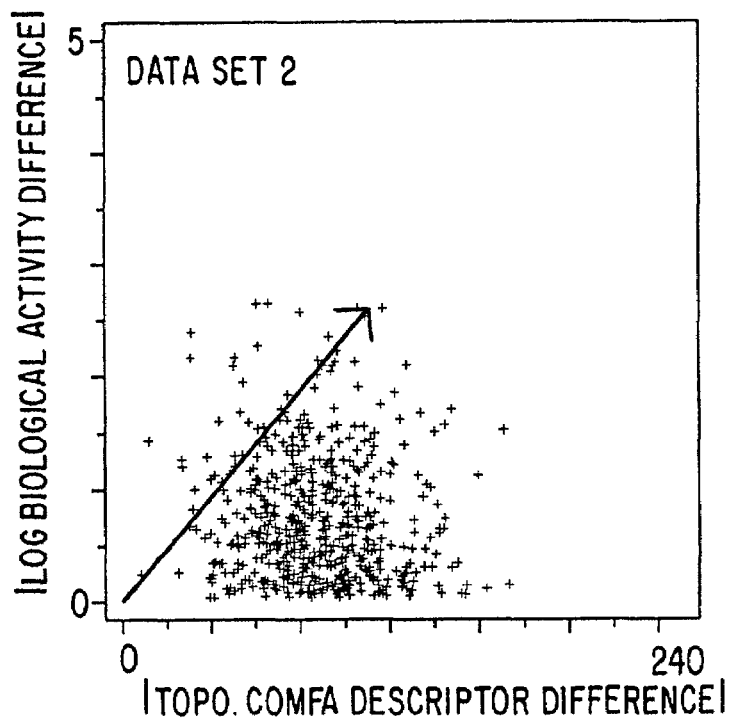
Figure 7C:
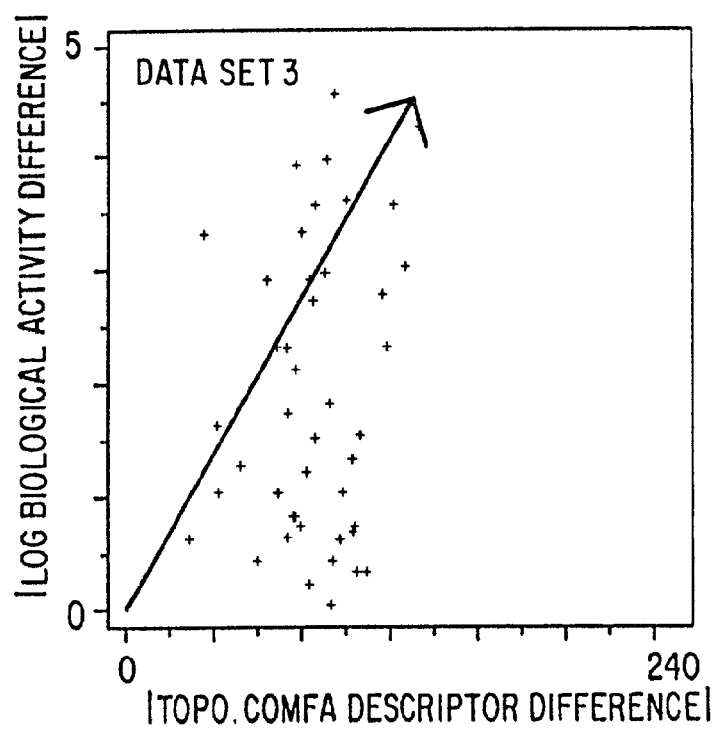
Figure 7D:
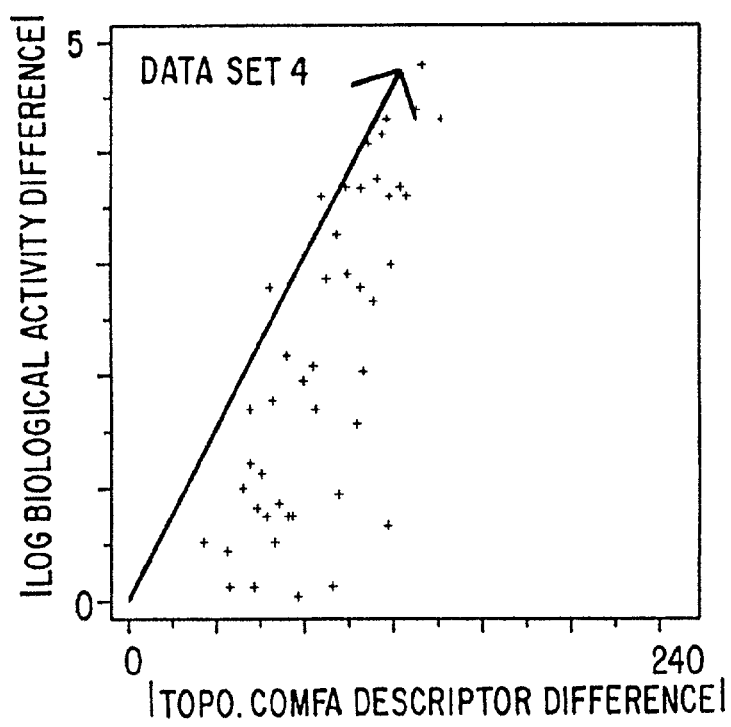
Figure 7E:
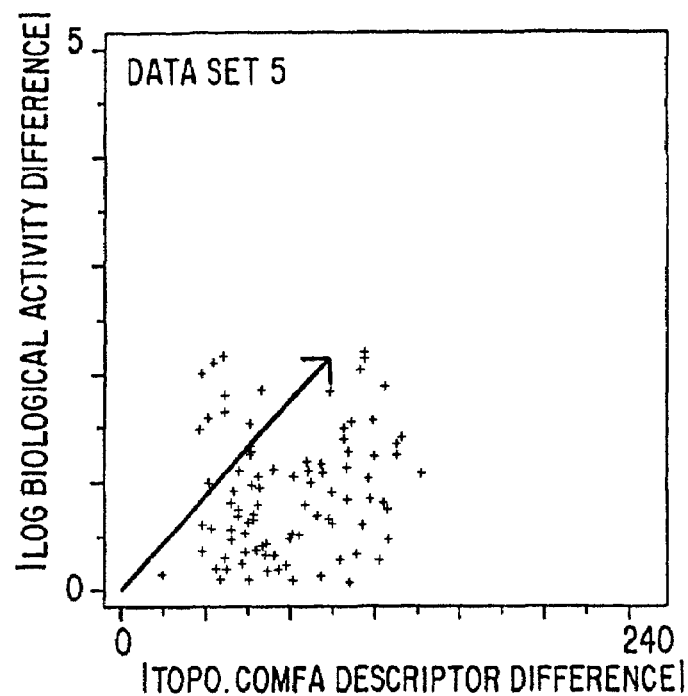
Figure 7F:
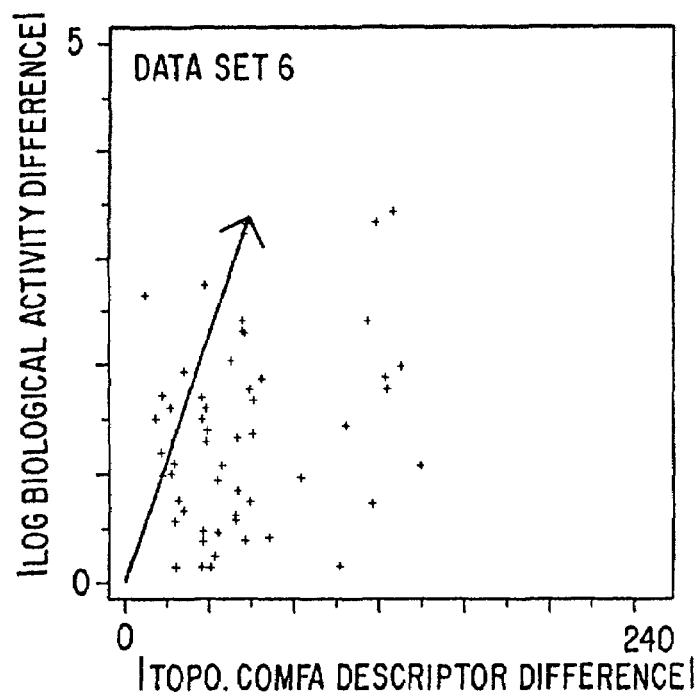
Figure 7G:
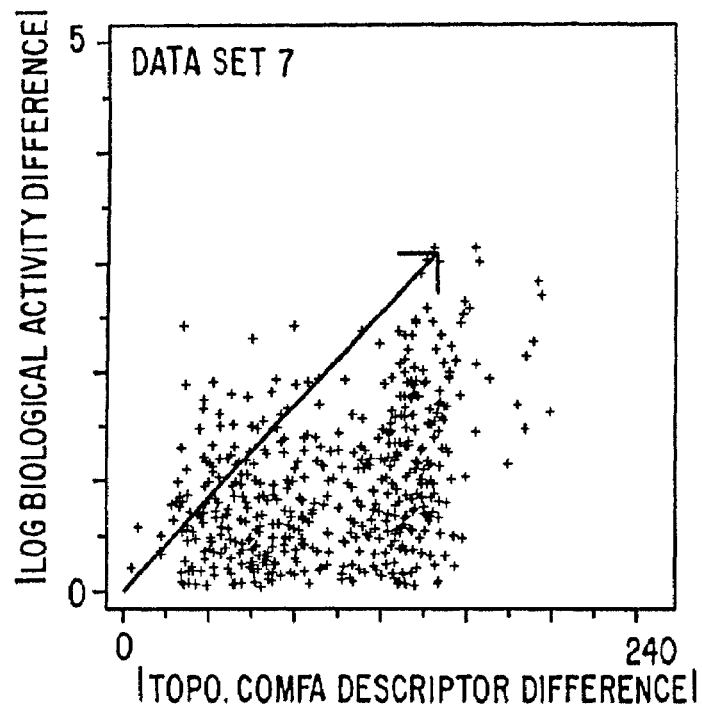
Figure 7H:
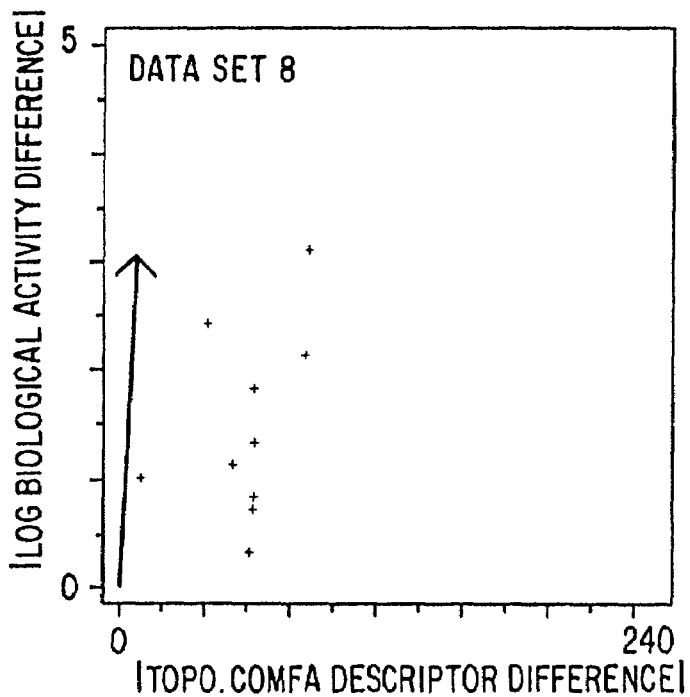
Figure 7I:
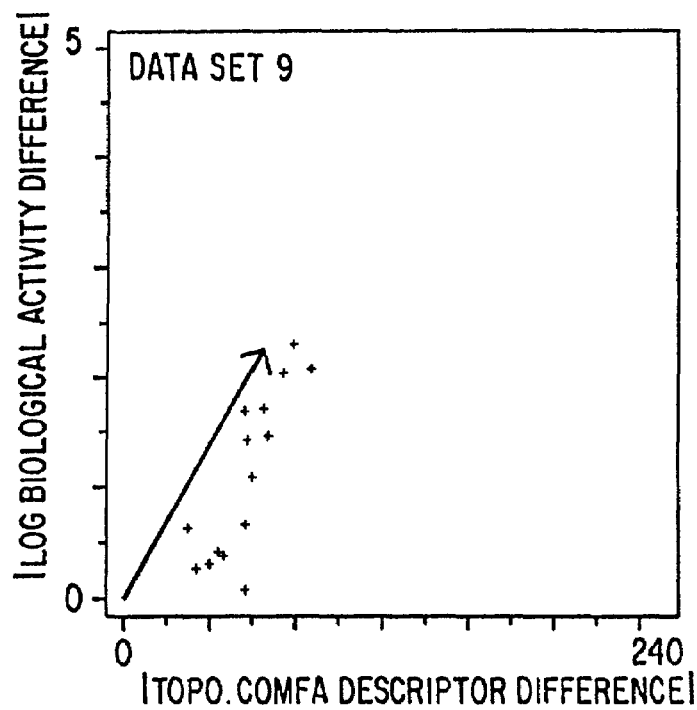
Figure 7J:
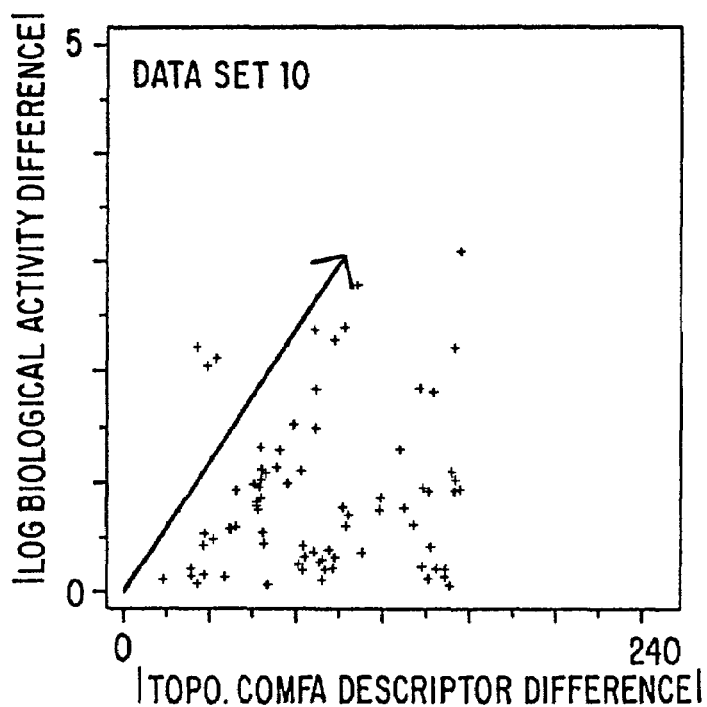
Figure 7K:
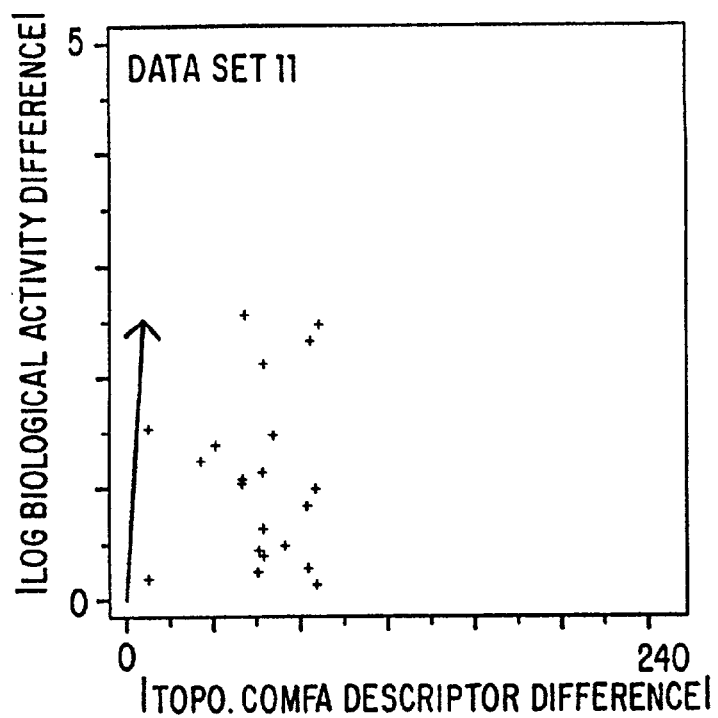
Figure 7L:
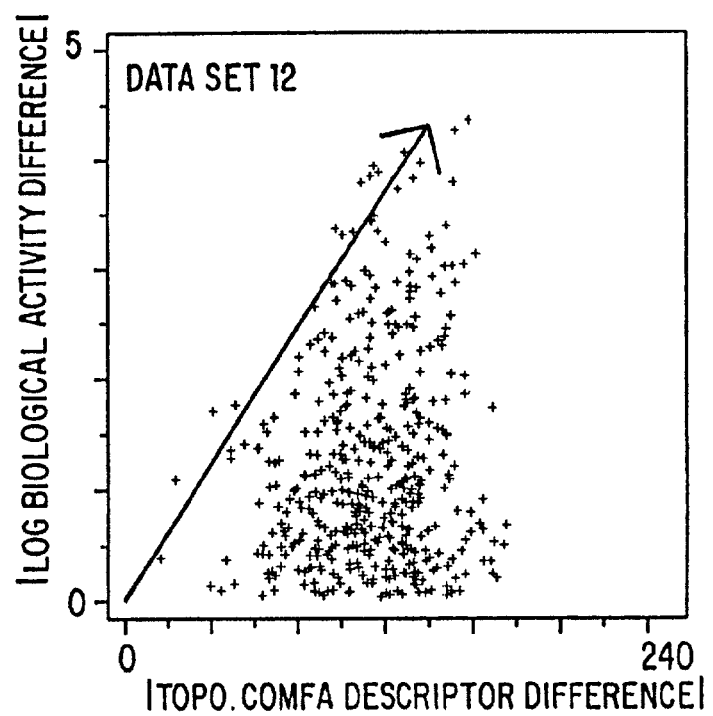
Figure 7M:
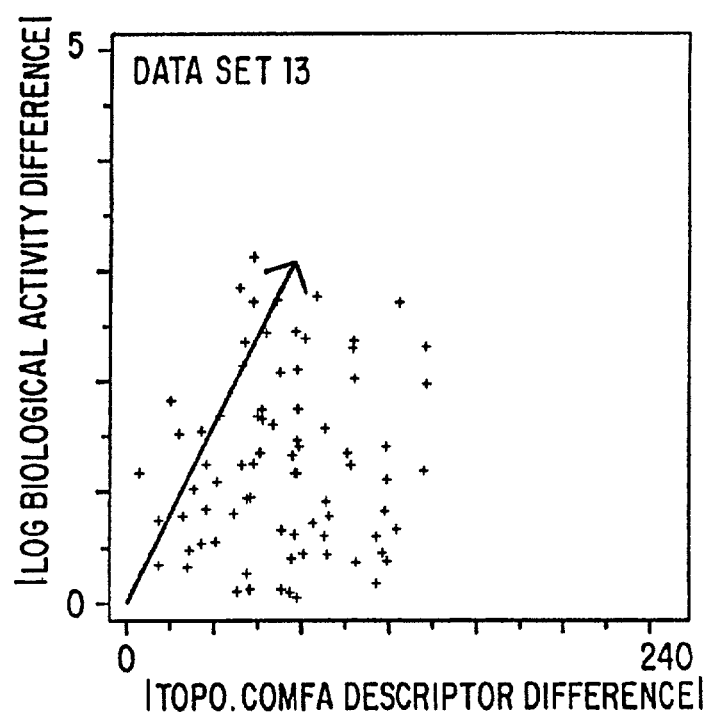
Figure 7N:
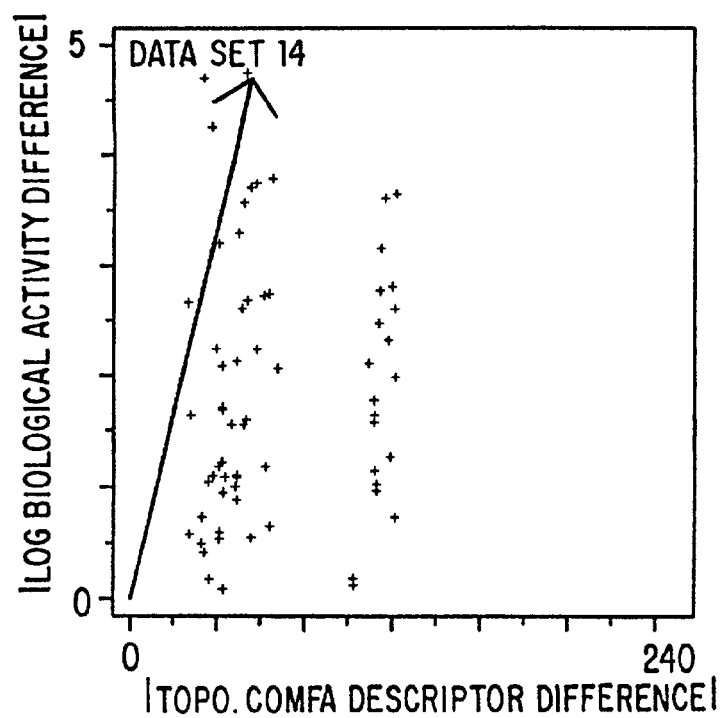
Figure 7O:
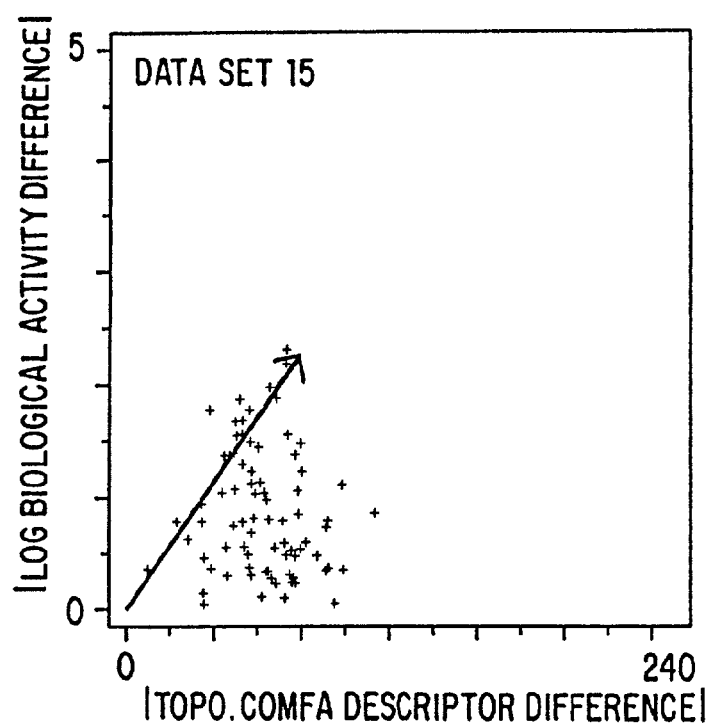
Figure 7P:
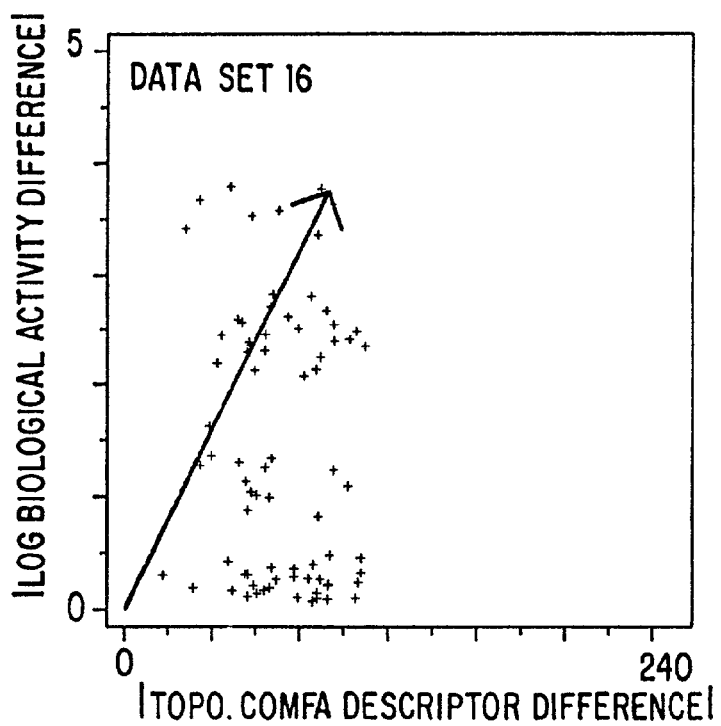
Figure 7Q:
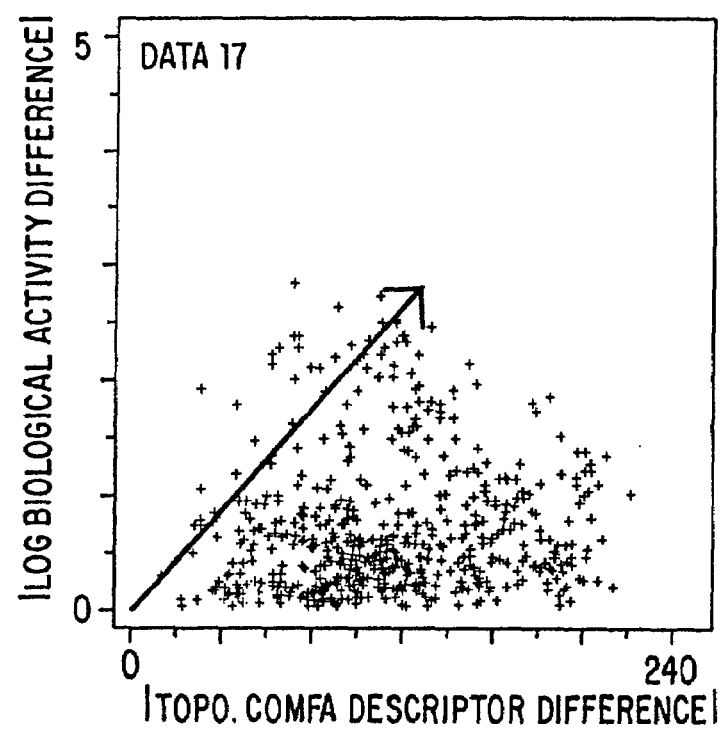
Figure 7R:
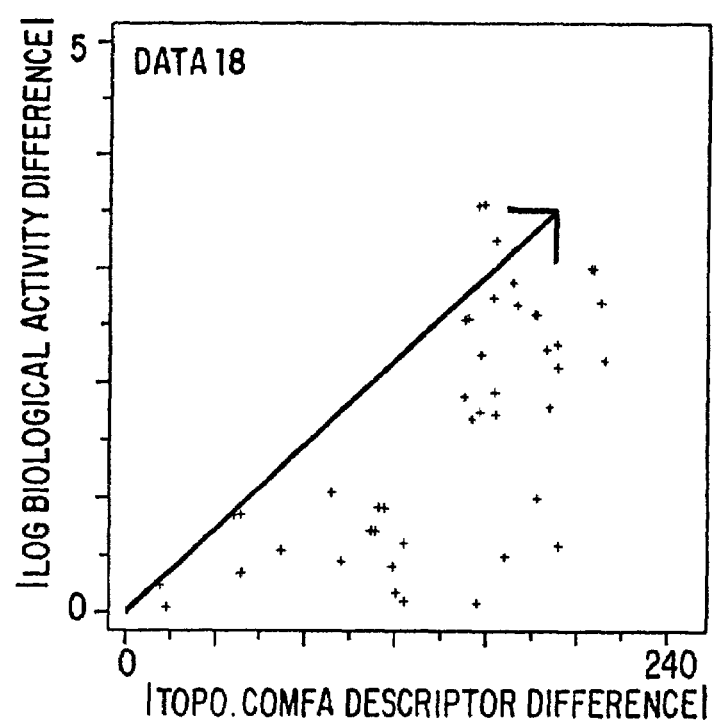
Figure 7S:
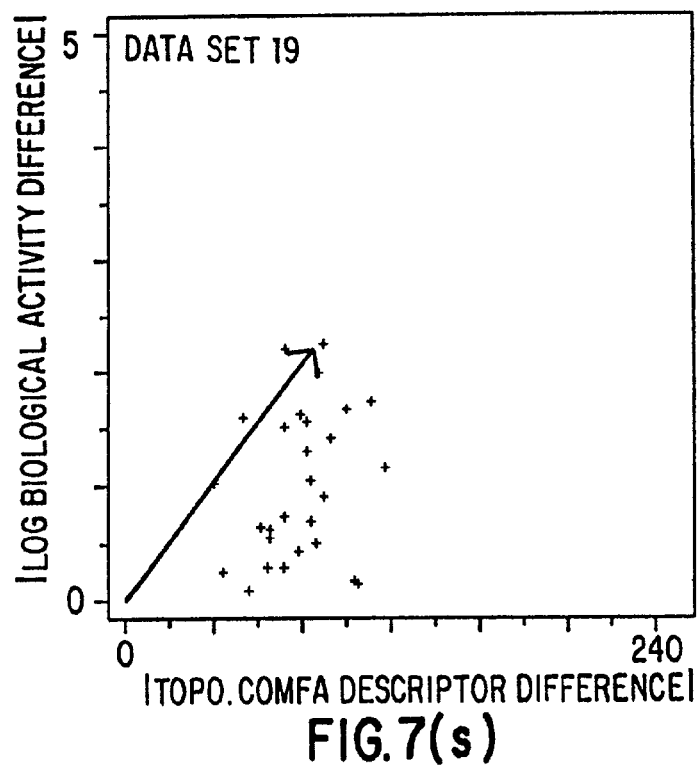
Figure 7T:
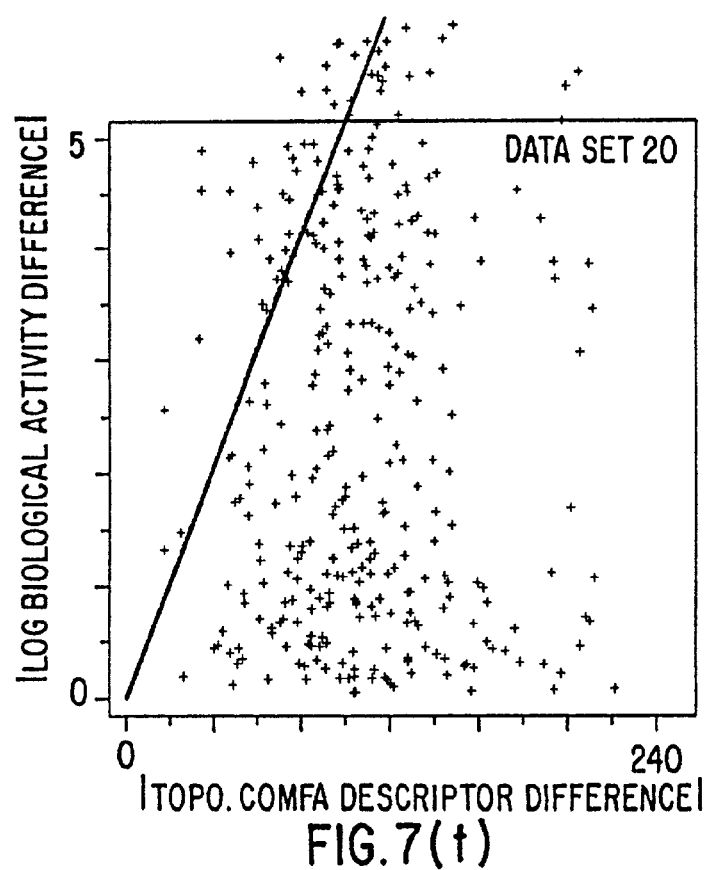

The validity of topomerically aligned CoMFA fields as a molecular structural descriptor, which can be used to describe the diversity of compounds, was confirmed on twenty data sets randomly chosen from the recent biochemical literature. The data sets spanned several different types of ligand-receptor binding interactions. The only criteria for the data sets were: 1) the reported biological activities must span at least two orders of magnitude; 2) the structural variation must be "monovalent" (only one difference per molecule); 3) the molecules contain no chiral centers; and 4) no page turning was required for data entry in order to reduce the likelihood of entry errors. Each data set was analyzed independently. The identification of the data sets is set forth in Appendix "C". The structural variations of the side chains of the core templates were entered as the Sybyl Line Notations of the corresponding thiols. (Sybyl Line Notations [SLNs] define molecular structures.) An -SH was substituted for the larger common template portion of each molecule and provided the two additional atoms needed for 3D orientation. According to the validation method of this invention the Patterson plots constructed as discussed above for the twenty data sets are shown in FIGS. 7(a)–7(t).

In 17 of the 20 cases, visual inspection of the plots suggests that the density of points in the lower right trapezoid is, indeed, greater than the density in the upper left triangle as predicted for a metric descriptor obeying the neighborhood rule. Also, for reasons noted earlier, some points do fall above the line as would be expected for the real world. However, the relative rarity of points in the upper left triangle of the plots indicates that "small steric field differences are not likely to produce large differences in bioactivity", the neighborhood rule. Thus, the distribution of points in the Patterson plots across all the randomly selected data sets is remarkably consistent with the theoretical prediction for a valid/useful diversity metric. It can be easily seen that the topomeric CoMFA metric is validated/useful.

Table 1 contains the density ratios from the quantitative analysis of the twenty data sets. The density ratios of the two test metrics (random number assignments and molecular force field energy divided by number of atoms for the diversity descriptor values) described earlier are presented for comparison. $X^2$ values reflecting the statistical significance of the ratios are also set forth next to the corresponding ratios.

TABLE 1

Patterson Plot Ratios and Associated $X^2$

| No. | Reference | CoMFA Ratio | CoMFA $X^2$ | Random Ratio | Random $X^2$ | Energy Ratio | Energy $X^2$ |
|---|---|---|---|---|---|---|---|
| 1 | Uehling | 1.71 | 10.27 | 0.98 | 0.01 | 0.98 | 0.02 |
| 2 | Strupczewski | 1.39 | 57.33 | 1.01 | 0.02 | 0.97 | 0.47 |
| 3 | Siddiqi | 1.44 | 6.26 | 0.92 | 0.01 | * | * |
| 4 | Garratt-1 | 1.72 | 13.01 | 1.02 | 0.02 | 1.00 | 0.00 |
| 5 | Garratt-2 | 1.37 | 8.02 | 1.04 | 0.11 | 0.97 | 0.07 |
| 6 | Heyl | 1.04 | 0.08 | 0.99 | 0.01 | 0.97 | 0.05 |
| 7 | Cristalli | 1.40 | 51.21 | 1.00 | 0.00 | 0.96 | 0.46 |
| 8 | Stevenson | 0.95 | 0.02 | 0.98 | 0.00 | 0.98 | 0.01 |
| 9 | Doherty | 1.63 | 3.54 | 1.02 | 0.01 | 0.96 | 0.02 |
| 10 | Penning | 1.45 | 10.33 | 0.99 | 0.01 | 1.00 | 0.00 |
| 11 | Lewis | 0.95 | 0.04 | 1.05 | 0.05 | 0.97 | 0.02 |
| 12 | Krystek | 1.64 | 119.92 | 1.00 | 0.00 | 0.97 | 0.49 |
| 13 | Yokoyama-1 | 1.18 | 1.88 | 1.00 | 0.00 | 0.93 | 0.41 |
| 14 | Yokoyama-2 | 1.23 | 2.62 | 1.02 | 0.02 | 0.99 | 0.01 |
| 15 | Svensson | 1.27 | 3.72 | 1.04 | 0.00 | 0.99 | 0.00 |
| 16 | Tsutsumi | 1.38 | 6.50 | 0.94 | 0.02 | 0.96 | 0.06 |
| 17 | Chang | 1.34 | 45.55 | 1.01 | 0.12 | 0.99 | 0.03 |
| 18 | Rosowsky | 1.71 | 12.46 | 0.95 | 0.10 | 1.00 | 0.00 |
| 19 | Thompson | 1.47 | 3.96 | 1.06 | 0.09 | 1.00 | 0.00 |
| 20 | Depreux | 1.22 | 10.85 | 0.98 | 0.07 | * | * |
|  | MEAN | 1.38 | 18.38 | 1.00 | 0.03 | 0.98 | 0.12 |
|  | STND. DEVIATION | 0.24 | 29.43 | 0.04 | 0.04 | 0.02 | 0.19 |

*Data sets 3 and 20 are not reported for the force field energy because one of the structures in each data set (in the topomeric conformation) had a very strained energy greater than 10 kcal/mole-atom, which produced a discontinuously large metric difference.

The chi-squared distributions for 1 degree of freedom are:

| | P = | | | | |
|---|---|---|---|---|---|
| | .75 | .90 | .95 | .99 | .999 |
| $X^2 =$ | 1.32 | 2.71 | 3.84 | 6.64 | 10.83 |

Figure 8A:
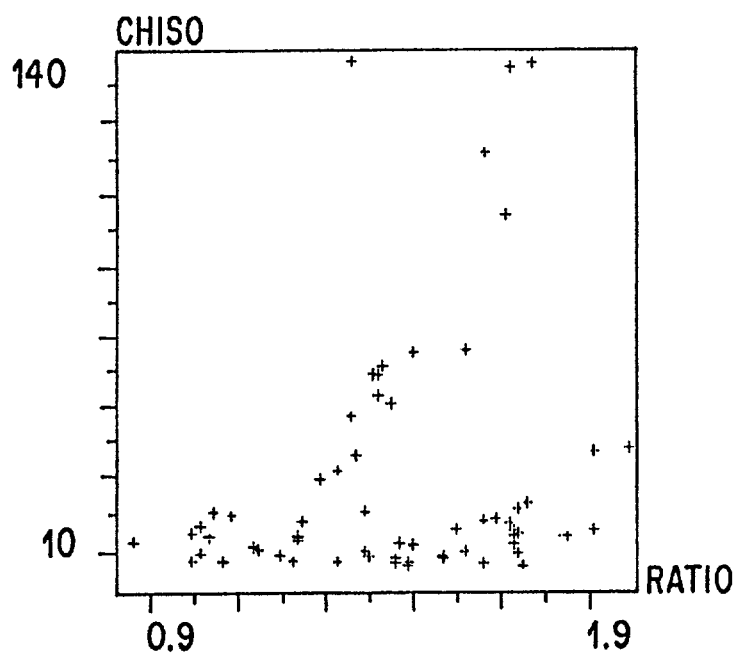
FIGS. 8A and 8B show the two scatter plots displaying the relation between $X^2$ values and their corresponding density ratio values for the tested metrics over the twenty random data sets.
Figure 8B:
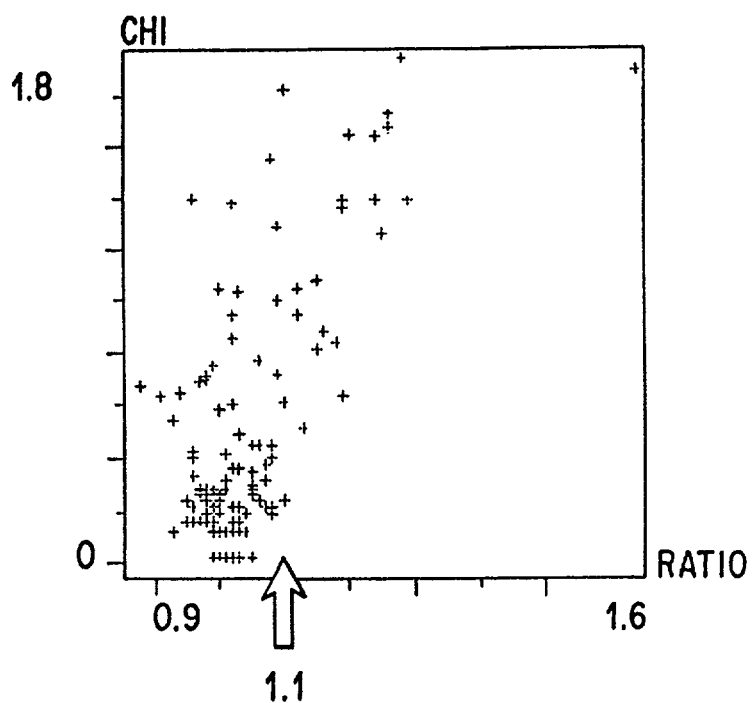

Typically, a confidence level of 95% is considered appropriate in statistical measures A metric is considered valid/useful for an individual data set if the Patterson plot ratio is greater than 1.1; that is, there is greater than a 10% difference in the density between the ULT and LRT. The use of 1.1 as a decisional criteria is confirmed by an examination of the scatter diagrams of $X^2$ values versus their corresponding ratios as shown in FIGS. 8A and 8B. (The value of X is actually plotted in FIG. 8B in order to separate the data points.) FIG. 8A shows the plot of $X^2$s having a value of greater than 3.84 (95% confidence limits) versus their corresponding ratios, while FIG. 8B shows the plot of $X^2$s (plotted as $\sqrt{X^2}$) having a value less than 3.84 versus their corresponding ratios. A ratio value of greater than 1.1 (FIG. 8A) clearly includes most of the statistically significant ratios, while a ratio value of less than 1.1 clearly includes most of the statistically insignificant ratios. While this is not a perfect dividing point and there is some overlap, there is also some distortion of the $X^2$ values due to limited population sizes as discussed below. Overall, the value of 1.1 provides a reasonable decision point.

As noted earlier, the validity of a metric should not be determined on the basis of one data set from the literature. A single literature data set usually presents only a limited range of structure/activity data and examines only a single biological activity. To obtain a proper sense of the overall validity/quality of a metric, its behavior over many data sets representing many different biological activities must be considered. It should be expected for randomly selected data sets that due to biological variability, an otherwise valid metric may appear invalid for some particular set. An examination of the data in Table 1 confirms this observation.

Except for data sets 6, 8, and 11, the ratios in Table 1 clearly confirm for the topomeric CoMFA metric that the density of points in the LRT is greater than in the ULT, and the $X^2$ values confirm the significance of the plots. At the same time, the data for the two test metrics clearly demonstrates with great sensitivity that this validation technique yields exactly the results expected for a meaningless metric; specifically, a density ratio substantially equal to 1 and no significance as determined by the $X^2$ test. Contrary to accepted notions in the prior art, with the discovery of this invention, random literature data sets can be used to validate metrics. The type of publicly unavailable data set (as will be discussed in relation to the Abbott data set below) where the bioactivity or inactivity for each molecule in the set has been experimentally verified is not required.

Sets 6, 8, and 11 are the exceptions which help establish the rule. It is realistic to expect that randomly selected data sets would include some where molecular edge (typically a collision with receptor atoms) or other distorting effects would be present. For set 6, one experimental value was so inconsistent with other reported values that the authors even called attention to that fact. In addition to a problematic experimental value, all the structural changes are rather small but some of the biological changes are fairly large. Something very unusual is clearly happening with this system. For set 8, there is simply not enough data. Only 5 compounds (10 differences) were included and this proved insufficient to analyze even with the sensitivity of the Patterson plot. For data set 11, there were two contributing factors. First, the data set was small (only 7 compounds). Second, this set is a good example of an edge effect where a methyl group protruding from the molecules interacts with the receptor site in a unique manner which dramatically alters the activity Generally, the $X^2$ values support the significance (or lack of significance) of the ratio values. However, for data sets 9, 13, 14, and 15 the 95% confidence limit is not met. As with all statistical tests, $X^2$ is sensitive to the sample size of the population. For these data sets the N was simply too low. This sensitivity is well demonstrated by the difference in $X^2$ for sets 14 and 20. The ratio values of the two sets are virtually identical, but the $X^2$s differ significantly since set 14 has few points and set 20 many points. Thus, $X^2$ may be used to confirm the significance of a ratio value, but, on the other hand, can not be used to discredit a ratio value when too few data points are present. It can be clearly seen that the topomeric CoMFA metric appears to define a useful dimensional space (measures chemistry space) better for some of the target sets than for others.

As was discussed above, a metric need not be perfect to be valid. Even using an imperfect metric significantly increases the probability that molecules can be properly characterized based on structural differences. As the quality of the metric increases, the probability increases. Thus, metrics which appear valid by the above analysis with respect to only a few test data sets are still useful. Metrics, like topomeric CoMFA, which are valid for 85% (17/20) of the data sets yield a higher probability that structurally diverse molecules can be identified.

Only with respect to data sets 6, 8, and 11 does the topomeric CoMFA metric not appear to provide a useful measure. Considering the fact that some of the data sets have limited samples and that a very wide range of biological interactions is represented, it is not unexpected that random variations like this will appear. The critically important aspect of this analysis is the fact that the metric is valid over a truly diverse range of types of ligand-substrate interactions. This strongly confirms its generally applicability as a valid measure of the diversity of molecules which can be used to select optimally diverse molecules from large data sets such as for use in combinatorial screening library design.

Another important aspect of the invention can be derived from these plots. Upon close examination it can be seen that molecules having topomeric CoMFA differences (distances) of less than approximately 80–100 generally have activities within 2 log units of each other. This provides a quantitative definition of the radius of an area encompassing molecules possessing similar characteristics (similarly diverse) in topomeric CoMFA metric space—the neighborhood radius. Because the topomeric CoMFA metric is a valid molecular structural descriptor, it is known that molecules with similar structure and activity will cluster in topomeric CoMFA space. Topomeric CoMFA distances can, therefore, be usefully used as a diversity measure in selecting which molecules of a proposed combinatorial synthesis should be retained in the combinatorial screening library in order to have a high probability that most of the diversity available in that combinatorial synthesis is represented in the library. Thus, for a combinatorial screening library, only one example of a molecular pair having a pairwise distance from the other of less than approximately 80–100 kcal/mole (belonging to the same diversity cluster) would be included. However, every molecule of a pair having a pairwise distance greater than approximately 80–100 would be included. Of course, the "fineness" of the resolution (the radius of the neighborhood in metric space) can be changed by using a different activity difference. The Patterson plot permits by direct inspection the determination of a neighborhood distance appropriate to any chosen biological activity difference. It is suggested, however, that for a reasonable search of chemistry space for biologically significant molecules, a difference of 2 log units is appropriate. The exact value chosen be adjusted to the circumstances. Clearly, the opportunity for real world perturbing effects to dominate the measure is magnified by using less than 2 log units difference in biological activity. This is another example of the general signal to noise ratio problem often encountered in measurements of biological systems. For more accurate signal detection less perturbed by unusual effects, the data sets would ideally contain biological activity values spread over a wider range than what is usually encountered. The neighborhood radius predicted from an analysis of the topomeric CoMFA metric can now be used to cluster molecules for use in selecting those of similar structure and activity (such as is desired in designing a combinatorial screening library of optimal diversity).

The teachings of this disclosure so far may be summarized as follows: 1) a generalizable method for validating metric descriptors has been taught; 2) a specific descriptor, topomeric CoMFA, has been described; and 3) the topomeric CoMFA descriptor has been validated over a diverse sampling of different types of biological interactions from published data sets.

The extraordinary power inherent in the validation method to quantitatively determine a significant neighborhood radius is further demonstrated by a remarkable result obtained in the analysis of a data set of potential reactants for a combinatorial synthesis (all 736 commercially available thiols) from the chemical literature. The results were obtained by "complete linkage" hierarchical cluster analysis of the resulting steric field matrices, using "CoMFA_STD" or "NONE" scaling. (CoMFA_STD implies block standardization of each field, but without rescaling of the individual "columns" corresponding to particular lattice points, which here produces the same clusters as no scaling). For clustering the "distance" between any two molecules is calculated as the root sum of the squared differences in steric field values over all of the lattice intersections defined by the CoMFA "region".

In this example, cluster analysis using topomeric CoMFA fields produced a classification of reagents that makes sense to an experienced medicinal chemist. For example, when the topomerically aligned CoMFA fields of the 736 thiols are clustered, stopping when the smallest distance between clusters is about 91 kcal/mole (within the "neighborhood" distance of 80–100 found for these fields in the validation studies), 231 discrete clusters result differing from each other in steric size by at least a —$CH_2$— group. Upon inspection of the clustering, an experienced analyst will immediately recognize that at this clustering level of 231, a natural break occurs, ie: the separation between cluster level 231 and level 232 was greater than any encountered between levels 158 and 682. Further inspection of these results showed that, with perhaps ten exceptions, each cluster contained only compounds having a very similar 2D topology or connectivity, while different clusters always contained compounds having dissimilar 2D topology. Indeed, so logical was the grouping that it was possible to provide a characteristic and distinctive systematic name for each of the 238 clusters using mostly traditional or 2D chemical nomenclature as shown in Appendix "D". It is striking that this entirely automatic clustering procedure, based only on differences among the topomeric steric fields of 3D models of single conformers, generates a classification that coincides so well with chemical experience as embodied in an independently generated 2D nomenclature. From a pragmatic point of view, this result may also be said to validate the validation procedure in the eyes of an experienced medicinal chemist who will tend to judge a metric by whether its assessments of molecular similarity and diversity agree with his/her own experience.

The critical aspect of this clustering result is that the structurally most logical clustering was generated with a nearest neighbor separation of 91, in the middle of the 80–100 neighborhood distance determined from the validation procedure to be a good measure of similarity among the molecules in topomeric CoMFA metric space. That is, the neighborhood distance of approximately 80–100 (corresponding to an approximate 2 log biological difference) predicted from the topomeric CoMFA validation, generates, when used in a clustering analysis, logical systematic groupings of similar chemical structures. The exact size of the neighborhood radius useful for clustering analysis will vary depending upon: 1) the log range of activity which is to be included; and 2) the metric used since, in the real world, different metrics yield different distance values for the same differences in biological activity. As seen, the topomeric CoMFA metric can be used to distinguish diverse molecules from one another—the very quantitative definition of diversity lacking in the prior art which is necessary for the rationale construction of an optimally diverse combinatorial screening library.

The discovered validation method of this invention is not limited to the topomeric CoMFA field metric but is generalizable to any metric. Thus, once any metric is constructed, its validity can be tested by applying the metric to appropriate literature data sets and generating the corresponding Patterson plots. If the metric displays the neighborhood behavior and is valid/useful according to the analysis of the Patterson plots set forth above, the neighborhood radius is easily determined from the Patterson plots once an activity difference is selected. This neighborhood radius can then be used to stop a clustering analysis when the distance between clusters approaches the neighborhood radius. The resulting clusters are then representative of different aspects of molecular diversity with respect to the clustered property/metric. It should be noted that a metric, by definition, is only used to describe something which has a difference on a measurement scale. This necessarily implies a "distance" in some coordinate system. Mathematical transformations of the distances yielded by any metric are still "distances" and can be used in the preparation of the Patterson plots. For instance, the topomeric CoMFA field distances could be transformed into principal component scores and would still represent the same measure.

Since the validity of the metric is not dependent on the particular chemical/biological assays used to establish its validity, the metric can be applied to assemblies of chemical compounds of unknown activity. Clustering of these assemblies using the validated neighborhood radius for the metric will yield clusters of compounds representative of the different aspects of molecular diversity found in the assemblies. (It should be understood that active molecules for any given assay may or may not reside in more than one cluster, and the cluster(s) containing the active compound(s) in one assay may not include the active compound(s) in a different assay.)

As mentioned above, when designing an efficient combinatorial screening library, one wishes to avoid including more than one molecule which is representative of the same structural diversity. Therefore, if a single molecule is included from each cluster derived as above, a true sample of the diversity represented by all the molecules is achieved without overlap. This is what is meant by designing a combinatorial screening library for optimal diversity. The methodologies of the present invention for the first time enable the achievement of such a design.

5. Tanimoto Fingerprint Descriptor

There are other measures of molecular similarity which are not metrics, that is, they do not correspond to a distance in some coordinate system but for which differences between molecules can be calculated. One such measure is the Tanimoto[13] fingerprint similarity measure. This is one of the 2D measurements frequently used in the prior art to cluster molecules or to partially construct other molecular descriptors. (Technically descriptors containing a Tanimoto term are not metrics since the Tanimoto is not a metric). 2D fingerprint measures were originally constructed to rapidly screen molecular data bases for molecules having similar structural components. For the present purposes, a string of 988 has been found convenient and sufficiently long. A Tanimoto 2D fingerprint similarity measure (Tanimoto coefficient) between two molecules is defined as:

$$\frac{\text{No. Of Bits Occuring} \in \text{Both Molecules}}{\text{No. Of Bits} \in \text{Either Molecule}}$$

The Tanimoto fingerprint simply expresses the degree to which the substructures found in both compounds is a large fraction of the total substructures.

A. Neighborhood Property

At an American Chemical Society meeting in April, 1995, Brown, Martin, and Bures[3] of Abbott Laboratories presented clustering data generated in an attempt to determine which, if any, of the common descriptors available in the prior art produced "better clustering". "Better clustering" was defined as a greater tendency for active molecules to be found in the same cluster. One of the measures used was the Tanimoto 2D fingerprint coefficient calculated from the structures of the entire molecules (not just the side chains). Proprietary and publicly unavailable data sets were used by the Abbott group which covered a large number of compounds for which the activity or lack of activity in four assays had been experimentally verified over many years of pharmacological research. Although used as an analytical tool to measure clustering effectiveness and not itself a focus of the presentation, one of the graphs Martin presented plotted the "proportion of molecular pairs in which the second molecule is also active" against the "pairwise Tanimoto similarity between active molecules and all molecules" (hereafter referred to as a "sigmoid plot"). From the resulting graph Martin et al. essentially found that if the Tanimoto coefficient of molecule A (an active molecule) with respect to molecule B is greater than approximately 0.85, then there was a high probability that molecule B will also be active; ie., the activity of molecule B can be usefully predicted by the activity of molecule A and vice versa. While not recognized or taught by the Abbott group at the time, the present inventors recognized that, for a very restricted data set, the Abbott group had data suggesting that the Tanimoto coefficient displayed a neighborhood property.

B. Applicability of Tanimoto to Different Biological Systems

In order to determine whether the Tanimoto coefficient reflects a neighborhood property over a range of different biological assays, 11,400 compounds from Index Chemicus containing 18 activity measures with 10 or more structures were analyzed. (Index Chemicus covers novel compounds reported in the literature of 32 journals.) Lack of a reported activity was assumed to be an inactivity although, in reality, the absence of a report of activity probably means that the compound was just untested in that system. For comparison purposes, this assumption is a more difficult test in which to discriminate a trend than with the Abbott data base where it was experimentally known whether or not a molecule was active or inactive. However, all that is absolutely needed for this analysis is a high likelihood of having compounds that are "similar enough" in fingerprints to also be "similar enough" in biological activity. The converse, "similar biological activity must have similar fingerprints", is patently untrue and is not tested. Table 2 shows the structures and activities analyzed.

TABLE 2

Index Chemicus Activities

| Set No. | No. Anal. | Biological Activity |
|---|---|---|
| 1 | 30 | Antianaphylactic |
| 2 | 12 | Antiasthmatic |
| 3 | 71 | Antibacterial |
| 4 | 16 | Anticholinergic |
| 5 | 55 | Antifungal |
| 6 | 17 | Anti-inflammatory |
| 7 | 21 | Antimicrobial |
| 8 | 13 | B-adrenergic |
| 9 | 21 | Bronchodilator |
| 10 | 34 | Ca Antagonistic |
| 11 | 18 | Cytotoxic |
| 12 | 133 | Enzyme Inhibiting |
| 13 | 210 | Nematocidal |
| 14 | 12 | Opioid Rcptr. Bind |
| 15 | 39 | Platelet Aggr. Inh. |
| 16 | 11 | Radioprotective |
| 17 | 13 | Renin Inhibiting |
| 18 | 11 | Thrombin Inhib. |

Figure 9A:
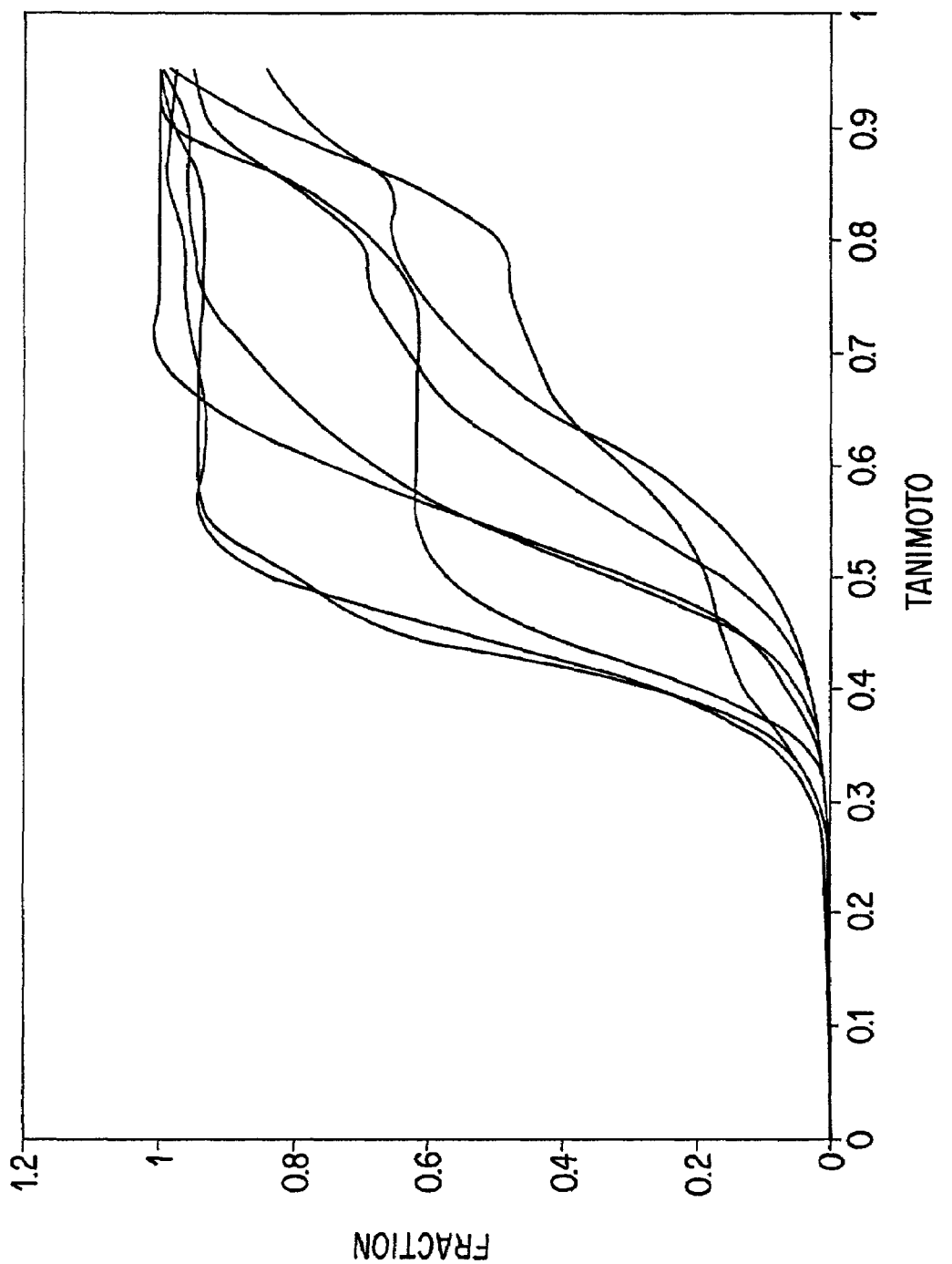
FIGS. 9A through 9C show the graphs of the Tanimoto similarity measure vs. the pairwise frequency of active molecules for 18 groups examined from Index Chemicus.
Figure 9B:
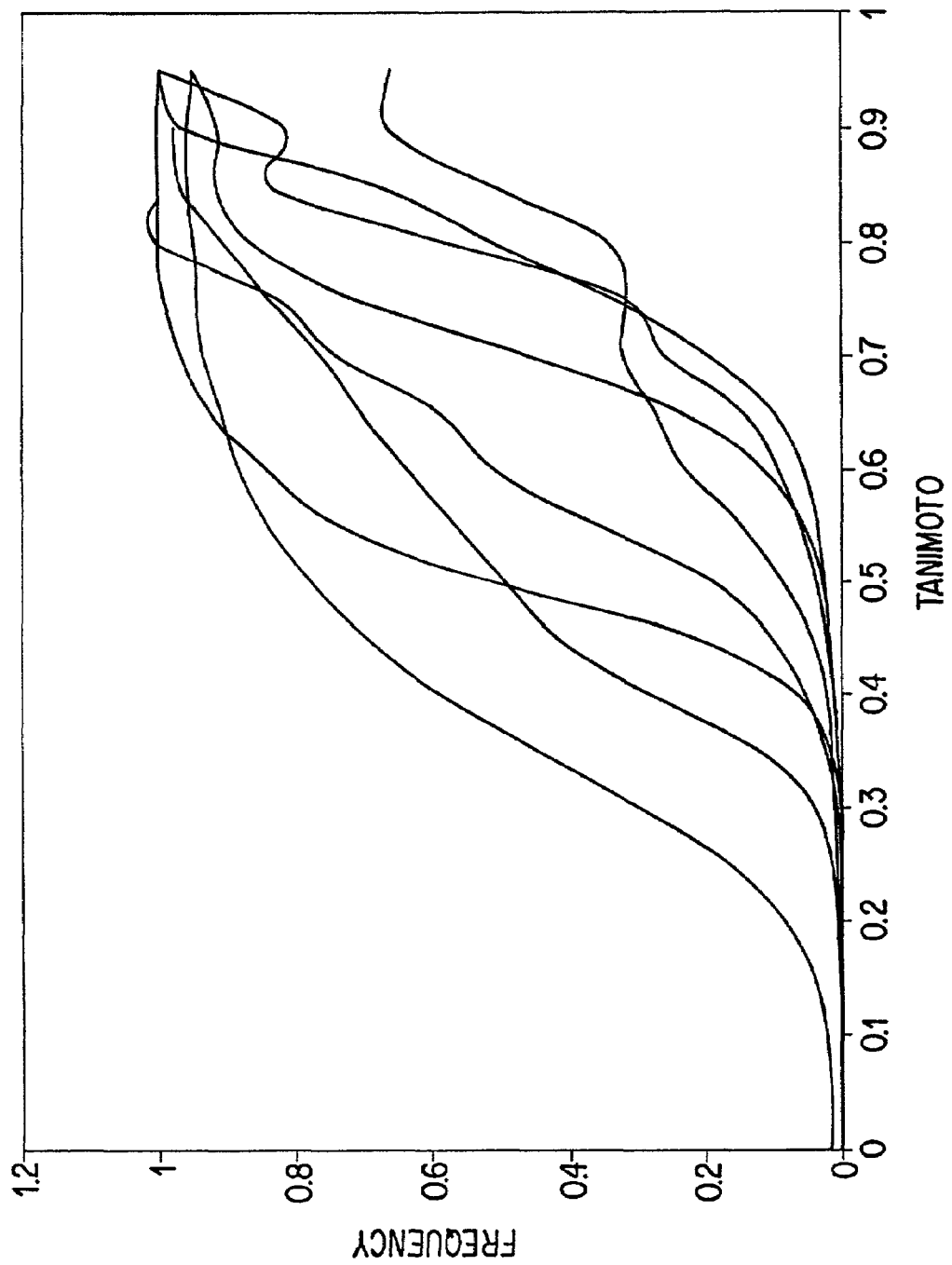
Figure 9C:
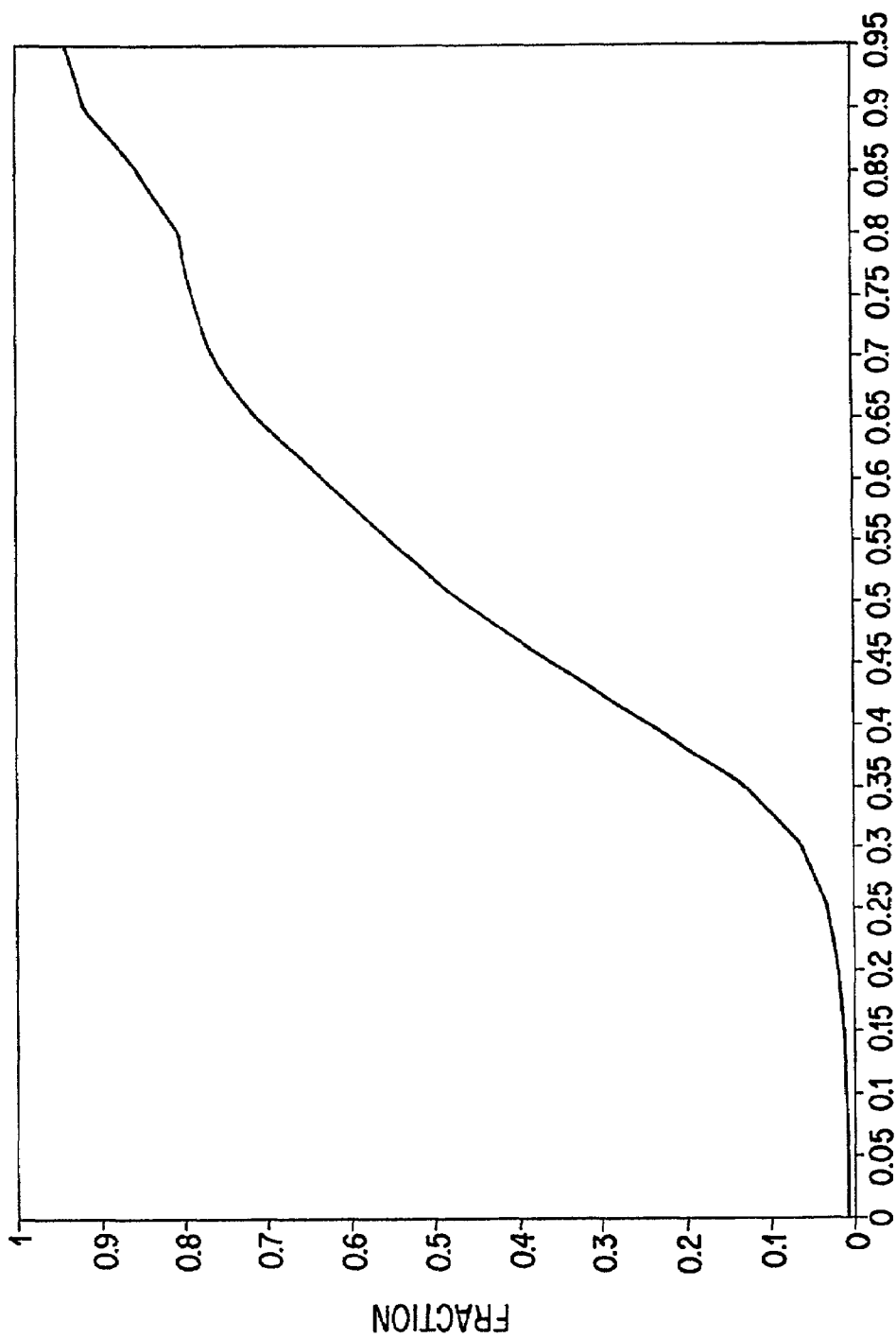

To convert this data to sigmoid plots, the data lists were examined for everything which was active, and a Tanimoto coefficient calculated (on the whole molecule) between every active molecule and everything else in the list. For plotting, the value of the number of molecules which were a given value (X) away from an active compound was determined. The proportion (frequency of such molecules) was plotted on the vertical axis and the Tanimoto coefficient on the horizontal axis. The bin widths for the X axis are 0.05 Tanimoto difference units wide, and the activity from Index Chemicus was simply "active" or "inactive". FIGS. 9A and 9B show the resulting plots for the 18 data sets broken down into sets of 9. Many of the curves have a sigmoid shape, but the inflection points clearly differ. Also, it is not clear what effect excluding the differences between active and inactive molecules has on the shape of the curves. To get an overall view, FIG. 9C shows the cumulative plot for both series of 9 activities. This plot generally indicates that, given an active molecule, the probability of an additional molecule, which falls within a Tanimoto similarity of 0.85 of the active, also being active is, itself, approximately 0.85. Stated slightly differently, when a Tanimoto similarity descriptor is summed over an arbitrary assortment of molecules and biological activities, it is clear that molecules having a Tanimoto similarity of approximately 0.85 are likely to share the same activity. Thus, the Tanimoto similarity displays a neighborhood behavior (neighborhood distance of approximately 0.15) when applied to a large enough number of arbitrary sets of compounds. As will be discussed later, one of the more powerful aspects of the Patterson plot validation method is that it can provide a relative ranking of metrics and distinguish on what type of data sets each may be more useful. In this regard, it will be seen that the whole molecule Tanimoto coefficient as a diversity descriptor has unanticipated and previously unknown drawbacks.

However, one of the principle features of the present invention, neither taught by the Abbott researchers nor recognized by anyone in the prior art, is that the Tanimoto descriptor can be used in a unique manner in the construction of a combinatorial screening library. In fact, as will be seen, it has been discovered that this descriptor can be used to provide an important end-point determination for the construction and merging of such libraries.

C. Comparison of Sigmoid and Patterson Plots

It is important to understand the difference in the types of information about descriptors and the neighborhood property which is yielded by the Abbott sigmoid plot and the generalized validation method and Patterson plot of the present invention To make a sigmoid plot, the molecules must be first be divided into two categories, active molecules and inactive molecules, based on a cut off value chosen for the biological activity. One molecule of a pair must be active (as defined by the cut off value) before the pair is included in the sigmoid plot. Pairs in which neither molecule has any activity, as well as those pairs in which neither molecule has an activity greater than the cut off value, do not contribute information to the sigmoid plot. Thus, the sigmoid plot does not use all of the information about the chemical data set under study. In fact, it uses a limited subset of data derivable from the more general Patterson plot described above. As a consequence very large sets of data (or sets for which both the activity and inactivity in an assay are experimentally known) are needed to get statistically significant results from the sigmoid plots.

By comparison, the Patterson plot clearly displays a great deal more information inherent in the data set which is relevant to evaluating the metric. Most importantly, the validity and usefulness of the metric can be quickly established by examining the Patterson plots resulting from application of the metric to random data sets. As will be shown in the next section, a metric may reflect a neighborhood property (such as in a sigmoid plot), but at the same time may not be a particularly valid/useful metric or may have limited utility. In Patterson plot analysis, all pairs of molecules and their associated activities or inactivities contribute to the validity analysis and to the determinations of the neighborhood radius. Thus, in a Patterson plot, it is easy to see what percentage of the total data set is included when the neighborhood definition is changed by choosing a different biological difference range. This has important consequences for choosing the correct neighborhood radius for clustering.

Figure 10A:
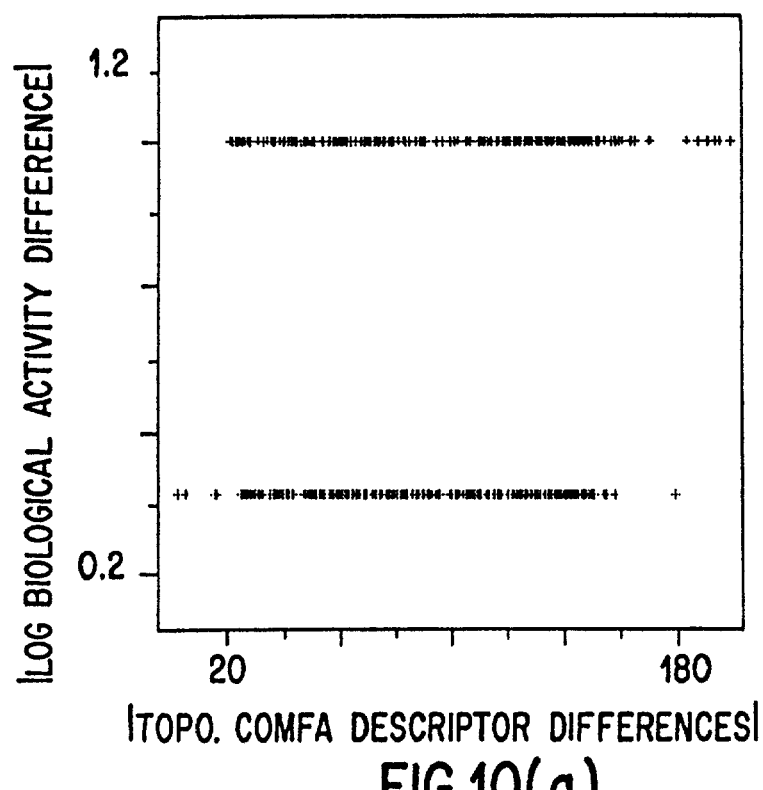
FIGS. 10A and 10B show a Patterson plot of the Cristalli data set using only those values which would have been used for a Tanimoto sigmoid plot of the same data set alongside a Patterson plot of the complete data set.
Figure 10B:
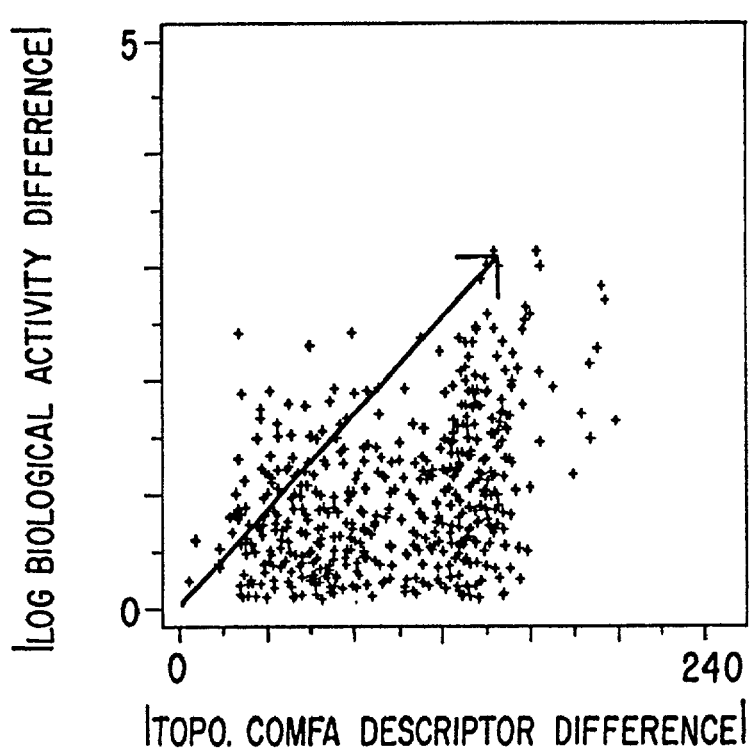

To better see the relationship between the information available from each type of plot, FIG. 10A shows a Patterson plot for the Cristalli data set reconstructed under the Abbott sigmoid plot simplification that the 32 molecules were either "active" (activity=1) or "inactive" (activity=0). The cut off value for biological activity was chosen to be 60 µM. Thus, "active" molecules were those with an A1 agonist potency of 60 µM or less, and "inactive" molecules were those with a potency greater than 60 µM. With this Abbott simplification, only two differences in bioactivities can occur for a pair of molecules: both active or inactive, difference=0; or one active and the other inactive, difference=1. The result of constructing a Patterson plot for this impoverished data set thus must appear as two parallel lines, as shown in FIG. 10A alongside the Patterson plot for the full Cristalli data set in FIG. 10B. Although a triangle and trapezoid should still be anticipated within such a reduced plot, the active/inactive classification so limits the observable biological differences that no pattern whatsoever is apparent. The very limited nature of the information retained is clearly seen. In particular, by only looking at molecular pairs in which one molecule is active above a predetermined cut off value, the sigmoid plot totally fails to take into account all the information about the behavior of the metric with respect to non-active pairs (in which one or both molecules have activities less than the cut off value) contained in the distribution of points in the Patterson plot. As a major consequence, the Patterson plot is: 1) able to derive information from much less data; and 2) much more sensitive to all the nuances contained in the data.

6. Comparison of Tanimoto and Topomeric CoMFA Metrics

Having recognized that both the topomeric CoMFA and Tanimoto coefficient metrics display the neighborhood property, a comparison (between Table 1 and columns 3 and 4 of Table 3) of the application of the two metrics to identical data sets yields interesting insights into their respective sensitivities. The prior art practice of using the value of (1−Tanimoto coefficient) as a distance was followed when performing the analysis. For columns 3 and 4 of Table 3, Patterson plots were constructed using the Tanimoto distances of the whole molecules represented in the 20 data sets which had been used for the topomeric CoMFA analysis. Patterson plots were also constructed using the Tanimoto distances of just the side chains (as was done with the topomeric CoMFA metric) of the molecules for the same 20 data sets. In Table 3 are shown the Tanimoto fingerprint density ratios for the whole molecule and side chain Tanimoto metrics and the corresponding $X^2$ values for the 20 data sets.

TABLE 3

Patterson Plot Ratios and Associated $X^2$

| No. | Reference | Col. 1 Side Chain Tanimoto Fingerprint Ratio | Col. 2 Side Chain Tanimoto Fingerprint $X^2$ | Col. 3 Whole Molecule Tanimoto Fingerprint Ratio | Col. 4 Whole Molecule Tanimoto Fingerprint $X^2$ |
|---|---|---|---|---|---|
| 1 | Uehling | 1.89 | 14.22 | 1.55 | 6.22 |
| 2 | Strupczewski | 1.70 | 143.48 | 1.41 | 59.61 |
| 3 | Siddiqi | 1.04 | 0.08 | 1.04 | 0.07 |
| 4 | Garratt-1 | 1.60 | 8.10 | 1.07 | 0.19 |
| 5 | Garratt-2 | 1.89 | 36.05 | 1.08 | 0.50 |
| 6 | Heyl | 1.71 | 13.83 | 1.01 | 0.00 |
| 7 | Cristalli | 1.75 | 144.54 | 1.31 | 30.27 |
| 8 | Stevenson | 0.94 | 0.05 | 1.07 | 0.04 |
| 9 | Doherty | 1.73 | 4.03 | 1.05 | 0.04 |
| 10 | Penning | 1.97 | 37.03 | 1.53 | 12.73 |
| 11 | Lewis | 1.64 | 4.80 | 1.01 | 0.00 |
| 12 | Krystek | 1.01 | 0.04 | 1.23 | 16.31 |

TABLE 3-continued

Patterson Plot Ratios and Associated $X^2$

| No. | Reference | Col. 1 Side Chain Tanimoto Fingerprint Ratio | Col. 2 Side Chain Tanimoto Fingerprint $X^2$ | Col. 3 Whole Molecule Tanimoto Fingerprint Ratio | Col. 4 Whole Molecule Tanimoto Fingerprint $X^2$ |
|---|---|---|---|---|---|
| 13 | Yokoyama-1 | 1.48 | 9.94 | 1.01 | 0.00 |
| 14 | Yokoyama-2 | 1.37 | 18.94 | 1.70 | 16.03 |
| 15 | Svensson | 1.64 | 16.61 | 1.02 | 0.02 |
| 16 | Tsutsumi | 1.74 | 21.56 | 1.58 | 14.35 |
| 17 | Chang | 1.34 | 145.00 | 1.13 | 8.36 |
| 18 | Rosowsky | 1.04 | 0.06 | 1.01 | 0.00 |
| 19 | Thompson | 1.72 | 7.83 | 1.17 | 0.68 |
| 20 | Depreux | 1.60 | 64.22 | 1.18 | 6.73 |
|  | MEAN | 1.54 | 34.62 | 1.21 | 8.61 |
|  | STANDARD DEVIATION | 0.32 | 49.85 | 0.23 | 14.57 |

Surprisingly the whole molecule Tanimoto appears to be a good descriptor for only 50% of the data sets (10/20 data sets with a ratio greater than 1.1). At first glance this is surprising in light of the original Abbott data, but, on second consideration, it is consistent with the observed significant individual variability of the plots obtained from the Index Chemicus analysis in FIGS. 9A and 9B. The Patterson plots confirm that the Tanimoto coefficient does display a neighborhood property for some data sets, but clearly it is less valid/useful for other sets. And it is not as consistent as the topomeric CoMFA or the side chain Tanimoto descriptor which were valid 85% (17/20) and 80% (16/20) of the time respectively. Upon inspection of the whole molecule Tanimoto data, it can be seen that the 10 data sets which do not have ratios greater than 1.1 all have a small Tanimoto range and/or contain relatively few compounds. The $X^2$ values for these data sets also confirm the lack of statistical significance. Essentially, the whole molecule Tanimoto is a less discriminating diversity measurement than the others and would appear to need, at the very least, more data and/or a greater range of values. The method of this invention clearly provides much more information and insight into the validation of the Tanimoto metric than did the Abbott style sigmoid plot.

For the majority of sets, 80%(16/20), the side chain Tanimoto metric also appears to be valid/useful. This is an extraordinarily surprising result since this metric has always been thought of in the prior art as useful only as a measure of whole molecule similarity. Overall, it compares favorably with topomeric CoMFA. A very interesting aspect, however, is that the sets for which validity is not apparent are not identical for the topomeric CoMFA and side chain Tanimoto metrics. The side chain Tanimoto metric does not appear valid with respect to sets 3, 8, 12, and 18. Clearly set 8 had too little data for either the topomeric CoMFA or the side chain Tanimoto descriptors. The most interesting comparison involves sets 3, 12, and 18 which validated the topomeric CoMFA metric but for which the side chain Tanimoto metric appears invalid. Upon inspection, these sets all contained substituents in which only the position of a particular side chain varied. Since the topomeric CoMFA metric is sensitive to the relative spatial orientations of the side chains, while the Tanimoto metric is only sensitive to the presence or absence of the side chains, the sterically driven topomeric CoMFA metric was sensitive to the differences in these sets while the Tanimoto was insensitive. In certain circumstances the Tanimoto may be a useful descriptor of molecular diversity for use on the reactants in a combinatorial synthesis; a result totally at odds with the wisdom of the prior art. Clearly, however, the differences in sensitivities between the metrics should be considered when applying them.

Further, considering the five metrics already discussed above (topomeric CoMFA, whole molecule Tanimoto, side chain Tanimoto, random numbers, and force field energy) it is clear that the validation method of this invention can be used to rank the relative quality (validity/usefulness) of the metrics. In addition, when enough metrics have been examined by the method of this invention, it will be possible to choose metrics appropriate to the type of molecular structural differences which it is desired to analyze. Correspondingly, when a metric, which has been validated over a very wide range of data sets and biological activities, yields surprising results (appears invalid) when applied to a new data set, one potential interpretation may be that the data are in error. This highlights another feature of the invention, the ability to reliably suggest that some experimental observations are generating unusual data. Instead of using a data set to validate a metric, the previously validated metric is used to examine the reliability of the data set. By constructing Patterson plots and checking the associated $X^2$ value for significance, experimental scientists have another tool with which they may independently assess their data, especially in situations where new biological activities are being investigated.

7. Additional Validation Results

At the present time, the results of performing validation studies on other possible metrics using the Patterson plot method of this invention and the 20 described data sets result in the following data:

TABLE 4

Patterson Plot Ratios

| No. | Reference | HB | LOGP | MR | AP | CONN | AUTO |
|---|---|---|---|---|---|---|---|
| 1 | Uehling | 1.83 | 1.09 | 1.07 | 1.55 | 1.19 | 1.66 |
| 2 | Strupczewski | 1.48 | 1.00 | 0.99 | 1.40 | 1.05 | 1.20 |
| 3 | Siddiqi | 1.47 | 0.97 | 0.92 | 1.00 | 1.07 | 1.00 |
| 4 | Garratt-1 | a | 1.01 | 1.01 | 0.90 | 1.11 | 1.14 |
| 5 | Garratt-2 | a | 1.01 | 1.00 | 0.97 | 1.09 | 1.09 |
| 6 | Heyl | 1.24 | 0.98 | 0.95 | 1.11 | b | 1.01 |
| 7 | Cristalli | 1.22 | 1.06 | 0.99 | 1.27 | 0.98 | 1.17 |
| 8 | Stevenson | a | 1.03 | 1.03 | 1.02 | 1.02 | 1.02 |
| 9 | Doherty | 1.07 | 1.00 | 1.01 | 1.18 | 1.02 | 1.28 |
| 10 | Penning | 1.72 | 1.00 | 0.97 | 1.05 | 1.00 | 1.36 |
| 11 | Lewis | *0.57 | 1.00 | 1.02 | 0.97 | 1.15 | 1.14 |
| 12 | Krystek | 1.69 | 0.85 | 0.85 | 1.43 | 1.01 | 1.00 |
| 13 | Yokoyama-1 | *0.71 | d | 1.01 | 1.25 | 1.01 | 0.99 |
| 14 | Yokoyama-2 | 1.00 | 1.00 | 0.99 | 1.25 | 1.05 | 0.99 |
| 15 | Svensson | *0.31 | 1.01 | 0.99 | 1.31 | 1.08 | 1.00 |
| 16 | Tsutsumi | 1.67 | 1.04 | 0.95 | 1.18 | 1.00 | 0.95 |
| 17 | Chang | 1.35 | 1.00 | 1.00 | 1.00 | c | 1.20 |
| 18 | Rosowsky | 1.44 | 1.03 | 0.96 | 1.23 | 1.08 | 1.21 |
| 19 | Thompson | a | 1.12 | 0.99 | 0.87 | 1.02 | 1.01 |
| 20 | Depreux | *0.44 | 1.02 | 0.99 | 0.99 | 1.01 | 0.98 |
|  | MEAN | *1.43 | 1.01 | 0.98 | 1.15 | 1.05 | 1.12 |
|  | STANDARD DEVIATION | *0.27 | 0.05 | 0.05 | 0.19 | 0.06 | 0.17 |

HB = Topomeric Hydrogen Bonding
LOGP = Calculated Log P
MR = Molar Refractivity
AP = Atom Pairs[14]
AUTO = Autocorrelation[15]
CONN = Connectivity Indices[16]

Combining the data from Table 4 with the data from Tables 1 and 3 permits the relative ranking of some known metrics:

| VALIDITY/USEFULNESS RANK: | No. Of Ratios > 1.1 |
|---|---|
| USEFUL | |
| Topomeric Steric CoMFA | 17/20 |
| Tanimoto 2D Fingerprints (Side Chain) | 16/20 |
| Topomeric HBond Spatial Fingerprints | 10/12 |
| LESS USEFUL: | |
| Tanimoto 2D Fingerprints (Whole Molecule) | 10/20 |
| Atom Pairs (R. Sheridan) | 11/20 |
| Autocorrelation | 9/20 |
| NOT USEFUL - INVALID: | |
| Connectivity Indices (Health Design Implementation, first 10) | 3/18 |
| Partition Coefficient (CLOGP) | 1/19 |
| Molar Refractivity (CMR) | 0/20 |
| Force Field Strain Energy | 0/18 |
| Random Numbers | 0/20 |

Note:
A denominator of less than 20 indicates that the metric could not be calculated for all 20 data sets.

8. Combinatorial Library Design Utilizing Validated Metrics

The starting point for the design of any combinatorial screening library is the choice of synthetic reaction scheme involving the selection of the core molecule and the possible reactants which could be used with any specific chemistry. As mentioned earlier, well known and understood organic reactions are generally utilized. Initially, information about the chemical structure of all the reactants (and cores, when appropriate) and the synthetic chemistry involved (what products can be built) is input as a database in the computer in a form recognizable by the computational software. Using the insights gained from the discovery of the validation method of this invention, it is now possible to design general purpose combinatorial screening libraries of optimal diversity.

Conceptually, the design process may be thought of as a filtering process in which the molecules available in a combinatorially accessible chemical universe are run through consecutive filters which remove different subsets of the universe according to specified criteria. The goal is to filter out (reduce the numbers of) as many compounds as possible while still retaining those compounds which are necessary to completely sample the molecular diversity of the combinatorially accessible universe. The basic design method of this invention along with several ancillary considerations is shown schematically in FIG. 11 using the filter analogy. For this example only two sets of reactants are considered with one reactant of each set being contributed to each final product molecule. The reactants are shown forming the top row and first column of a combinatorial matrix A. Only a portion of the possible combinatorial matrix is shown, the remainder being indicated by the sections connected to the matrix by dots. One set of reactants is represented by circles 1, and the other set by squares 2. Each empty matrix location represents one possible combinatorial product which can be formed from the two sets of reactants. (The matrix of possible products would be a rectangular prism for three sets of reactants, and a multidimensional prism for higher orders of reactant sets.) As the design process is implemented, the number of products to be included in the screening library design is reduced by each filter 4. Beside each filter step is indicated the corresponding text section describing that filter. Also set out opposite each filtering step is an indication of the software and its source required to implement that step.

A. Removal Of Reactants For Non-Diversity Reasons

In designing screening libraries derived from combinatorially accessible chemical universes, practical and end use considerations as well as diversity concerns can be used to reduce the number of reactants which will be used to combinatorially specify the product molecules. These practical and end-use criteria can be divided into those of general applicability and those of more specific applicability for a particular type of screening library (such as for drug discovery). The following discussion is not meant to be limiting, but rather is intended to suggest the types of selections which may be made.

i. General Removal Criteria

As a first consideration, reactants with unusual elements (such as the metals) are normally excluded when considering the synthesis of organic molecules. In addition, tautomerization of structures can cause problems when searching a universe of reactants data base either by missing structures that are actually present or by finding a specific functional group which is really not there. The most common example of this is the keto-enol tautomerism. Thus, possible tautomeric reactants must be examined and improper forms eliminated from consideration. Generally, reactants may be provided in solvent, as salts with counterions, or in hydrated forms. Before their structures can be analyzed for diversity purposes, the salt counter-ions, solvent, and/or other species (such as water) should be removed from the molecular structure to be used.

Figure 11A:
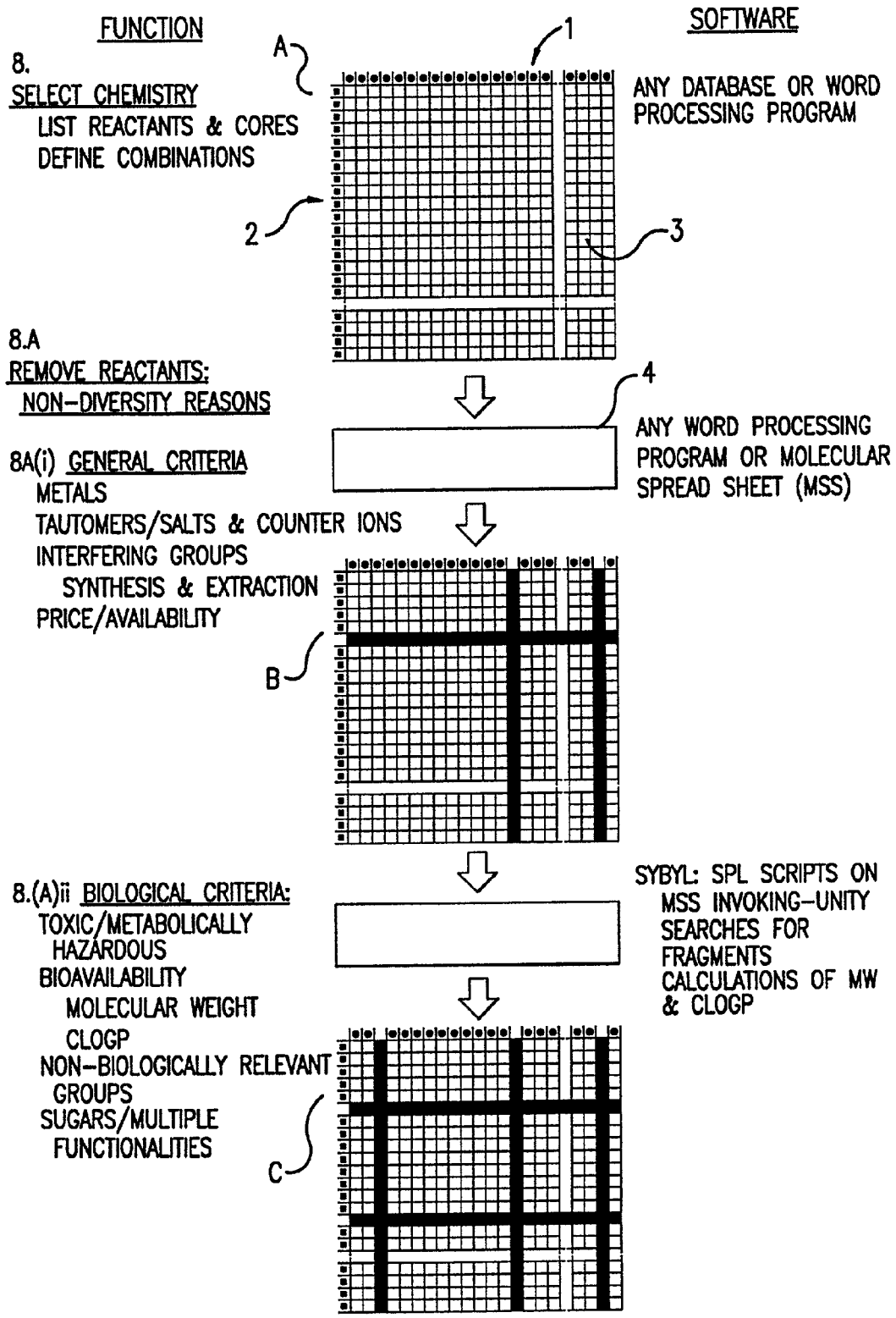
Figure 11C:
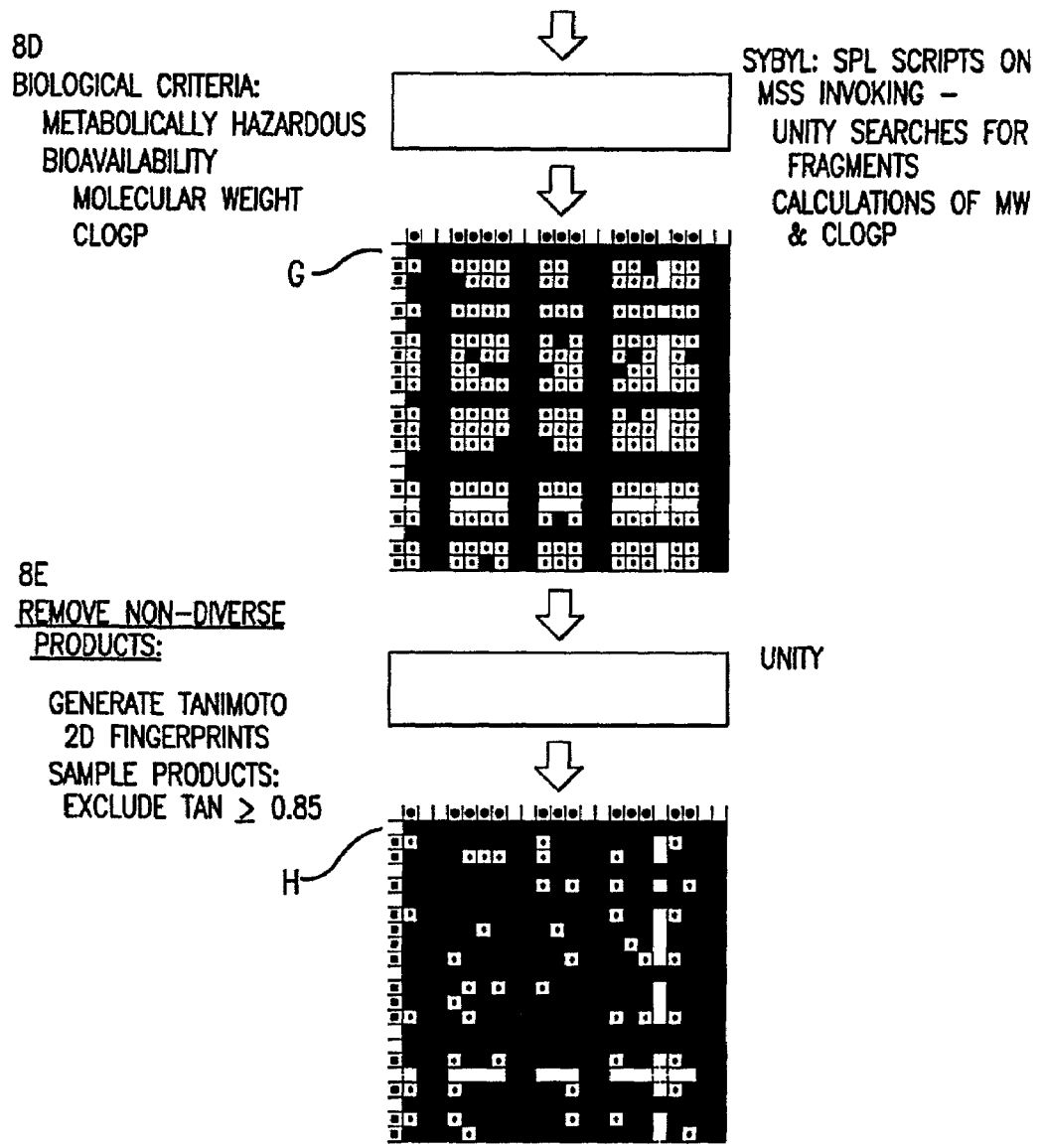

Additionally, reactants may contain chemical groups which would interfere with or prevent the synthetic reaction in which it is desired to use them. Clearly, either different reaction conditions must be used or these reactants removed from consideration. Sometimes, while the synthesis may be possible, extraction of the products resulting from some reactants may be difficult using the proposed synthetic conditions. Again, if possible, another synthetic scheme must be used or the reactants removed from consideration. Price and availability are not insignificant considerations in the real world. Some reactants may need to be specially synthesized for the combinatorial synthesis or are otherwise very expensive. In the prior art, expensive reactants would typically be eliminated before proceeding further with the library design unless they were felt to be particularly advantageous. One of the advantages of the method of this invention is that the decision whether to include expensive reactants may be postponed until the molecular structures have been analyzed by a validated descriptor. With confidence that the validated descriptor permits clustering of molecules representing similar diversity, often another, less expensive, reactant can be selected to represent the diversity cluster which also includes the expensive molecule. The specifics of any particular contemplated combinatorial synthesis may suggest additional appropriate filtering criteria at this level. In FIG. 11 the effect on the number of possible products of removing only a few reactants is easily seen in matrix B. For each reactant removed, whole rows and columns of possible products are excluded.

ii. Biologically Based Criteria

A library designed for screening potential pharmacological agents imposes it own limitations on the type and size of molecules. For instance, for drug discovery, toxic or metabolically hazardous reactants or those containing heavy metals (organometallics) would usually be excluded at this stage. In addition, the likely bioavailability of any synthetic compound would be a reasonable selection criteria. Thus, the size of the reactants needs to be considered since it is well known that molecules above a given range of molecular weights generally are not easily absorbed. Accordingly, the molecular weight for each reactant is calculated. Since the final molecular weight for a bioavailable drug typically ranges from 100 to 750 and since, by definition, at least two reactants are used in a combinatorial synthesis, reactants having a size over some set value are excluded. Typically, those above 600 are excluded at this stage at the present time. A lower value could be used, but it is felt that there is no reason to restrict the diversity unduly at this stage in the design process. Once again, of course, this value can be adjusted depending on the chemistry involved.

Another aspect of bioavailability is the diffusion rate of a compound across membranes such as the intestinal wall. Reactants not likely to cross membranes (as determined by a calculated LogP or other measure) would usually be eliminated. At the present time, although the CLOGP for reactants makes only a partial contribution to the product CLOGP, it is believed that if any reactant has a CLOGP greater than 10, it will not make a usable product. Accordingly, the CLOGP is calculated for each reactant and only those with CLOG$\leq$10 are kept. Again, in any particular case, a different value of CLOGP could be utilized. For those reactants for which it is difficult or impossible to calculate a LOGP, it is assumed the CLOGP would be less than 10 so that the reactants are kept in the library design at this point. As will be discussed later, a CLOGP will also be calculated on the products.

Other reactants are considered undesirable due to the presence of structural groups not considered "bio-relevant". Bio-relevance is judged by comparison with known drugs and by the experience of medicinal chemists involved in the design of the library. It is hoped that a future formal analysis of drug databases will yield further information about which groups should be excluded. Exclusion on this basis should be minimized since one of the goals of the combinatorial library design process is to find biologically active molecules through the exploration of combinatorial chemistry space which might not otherwise be found. Other removal criteria may be based on whether possible reactants involved sugars or had multiple functionalities. At the present time, the compounds shown in Table 5 are believed to be undesirable and are generally excluded at the initial stage of library design.

TABLE 5

Biologically Non-Relevant Groups

| GROUP DEFINITION | SYBYL Line Notation (SLN) | Reason(s) For Exclusion |
| --- | --- | --- |
| BOC | C(OC(=O)N)(CH3)(CH3)CH3 | Stability |
| FMOC | C[1]H:C[2]:C(:CH:CH:CH@1)CH(CH2OC(=O)N)\ C[22]:C@2:CH:CH:CCH:CH:@22 | Stability |
| Hydrolyzable acyclic groups | Lvg-[!r]C(-Any)-[!r]Lvg{Lvg:O\|N\|Br\|Cl\|I} | Stability |
| Silicon, Aluminium, Calcium | Si, Al, Ca | Unfashionable |
| Polyhydroxyls/sugars | HOCC(OH)COH | Extraction Difficulties |
| Allyl halides | HaloC(Any)C=:Any{Halo:Br\|Cl\|I} | Stability, alkylating agent |
| Benzyl halides | HaloC(Any)C=:Any{Halo:Br\|Cl\|I} | Stability, alkylating agent |
| Phenacyl halides | HaloC(Any)C=:Any{Halo:Br\|Cl\|I} | Stability, alkylating agent |
| Alpha-halo carbonyls | HaloC(Any)C=:Any{Halo:Br\|Cl\|I} | Stability, alkylating agent |
| Acyl halides | Csp(=O)Hal{Csp:C\|S\|P} | Stability, alkylating agent |
| Phosphyl halides | Csp(=O)Hal{Csp:C\|S\|P} | Stability, alkylating agent |
| Thio halides | Csp(=O)Hal{Csp:C\|S\|P} | Stability, alkylating agent |
| Carbamates | NoroC(=O)Hal{Noro:N\|O\|S} | Stability, alkylating agent |
| Chloroformates | NoroC(=O)Hal{Noro:N\|O\|S} | Stability, alkylating agent |
| Isocyanates | N=C=Het | Stability, alkylating agent |
| Thioisocyanates | N=C=Het | Stability, alkylating agent |
| Diimides | N=C=Het | Stability, alkylating agent |
| Sulfonating agents | Het(=O)(=O))Lvg{Lvg:OHev\|Hal} | Stability, alkylating agent |
| Phosphorylating agents | Het(=O)(=O))Lvg{Lvg:OHev\|Hal} | Stability, alkylating agent |
| Epoxides, etc. | C[1]HetC@1 | Stability, alkylating agent |
| Diazos | Any~N[F]~N[F] | Stability, toxicity |
| Azides | Any~N[F]~N[F]~Oorn[F]{Oorn:O\|N} | Stability, toxicity |
| Nitroso | Any~N[F]~N[F]~Oorn[F]{Oorn:O\|N} | Toxicity |
| Mustards | HaloC(Any)C(Any)Lvg{Lvg:Het\|Halo}{Halo:Br\|Cl\|I} | Stability, alkylating agent |
| 2-halo ethers | HaloC(Any)C(Any)Lvg{Lvg:Het\|Halo}{Halo:Br\|Cl\|I} | Stability, alkylating agent |
| Quaternary Nitrogens | Hev~Norp(~Hev)(~Hev)~Hev{Norp:P\|N} | Extraction difficulties |
| Quaternary Phosphorus | Hev~Norp(~Hev)(~Hev)~Hev{Norp:P\|N} | Extraction difficulties |
| Acid anhydrides | Het=Any-[!r]O-[!r]Any=Het | Stability, alkylating agent |
| Aldehyde | CCH=O | Stability, alkylating agent |
| Polyfluorinates | FC(F)C(F)F | Unfashionable |
| Michael acceptor | O=C(Nothet)-C=Any(H)Nothet{Nothet:C\|H} | Toxicity |
| Trialkylphosphines | P(C)(C)C | Stability |
| Other Triaryls | Any:Any-[!r]Any(-[!r]Any:Any)\ (-[!r]Any:Any)Lvg{Lvg:Het\|Hal} | Stability |
| Alpha-dicarbonyls | Oorn=[!r]Any(AnyHev)-C=[!r]Oorn{Oorn:O\|N} | Stability |

The choice of whether to eliminate some reactants based on such general and specific considerations will vary with the given situation. Except in the case of toxic materials, it is recognized that any other limiting selection decreases the diversity of the combinatorial library and potentially eliminates active molecules. As always, when eliminating reactants at the very beginning of library design, the problem boils down to a question of probabilities: what is the likelihood of missing a significant lead molecule? In the real world, what is desired at the very least is a high probability that it is unlikely that such a molecule will be missed if the selection criteria under consideration are implemented. The application of many of these selection criteria (price, availability, toxicity, bioavailability, diffusion, and non-biologically relevant structural groups) can occur before, during, or after the screening library has been selected based on other criteria. Clearly, however, the earlier these selection criteria are applied, the greater will be the reduction in the number of combinatorial possibilities which will need to be evaluated later in the design process. As will be discussed below, not only are these criteria applied at the reactant level, but some of them will also be applied again at the product level. Reduction of the number of reactants (for the reasons set forth above) in the early stages of the library design process is indicated in FIG. 11 at matrix C.

B. Removal of Non-Diverse Reactants

As noted earlier, an ideal combinatorial screening library will: 1) have molecules representing the entire range of diversity present in the chemical universe accessible with a given set of combinatorial materials; and 2) will not have two examples of the same diversity when one will suffice. The goal is to obtain as complete a sampling of the diversity of chemical space as is possible with the fewest number of molecules, and, coincidentally, at lowest cost. In selecting a subset of a possible combinatorial universe to include in a screening library, there are two opportunities based on diversity considerations to reduce the number of included molecules. The first opportunity occurs when selecting reactants for the combinatorial synthesis. The fewer the number of reactants, the much fewer the number of combinatorial possibilities. The second opportunity occurs after all the combinatorial possibilities from the chosen reactants (and core) have been selected. The method of the present invention utilizes both opportunities by using validated metrics appropriate to each situation.

Any metric which has been shown by the Patterson plot validation methodology to be valid/useful when applied to reactants may be used at this stage of the library design process. However, there are a number of reasons to use a metric which reflects the steric diversity of the combinatorially accessible chemical universe. The principle reason is that the accumulated observation of biological systems is that ligand-substrate binding is primarily governed by three dimensional considerations. Before a reactive side group can get to the active site, before appropriate electrostatic interactions can occur, before appropriate hydrogen bonds can be formed, and before hydrophobic effects can come into play, the ligand molecule must basically "fit" into the three dimensional site of the substrate. Thus a principal consideration in designing screening libraries should be to sample as much of the three dimensional (steric) diversity of the combinatorial universe as is possible. The preferred method of the present invention does this by utilizing the validated topomeric CoMFA metric to analyze the steric properties of the proposed reactants.

Figure 12:
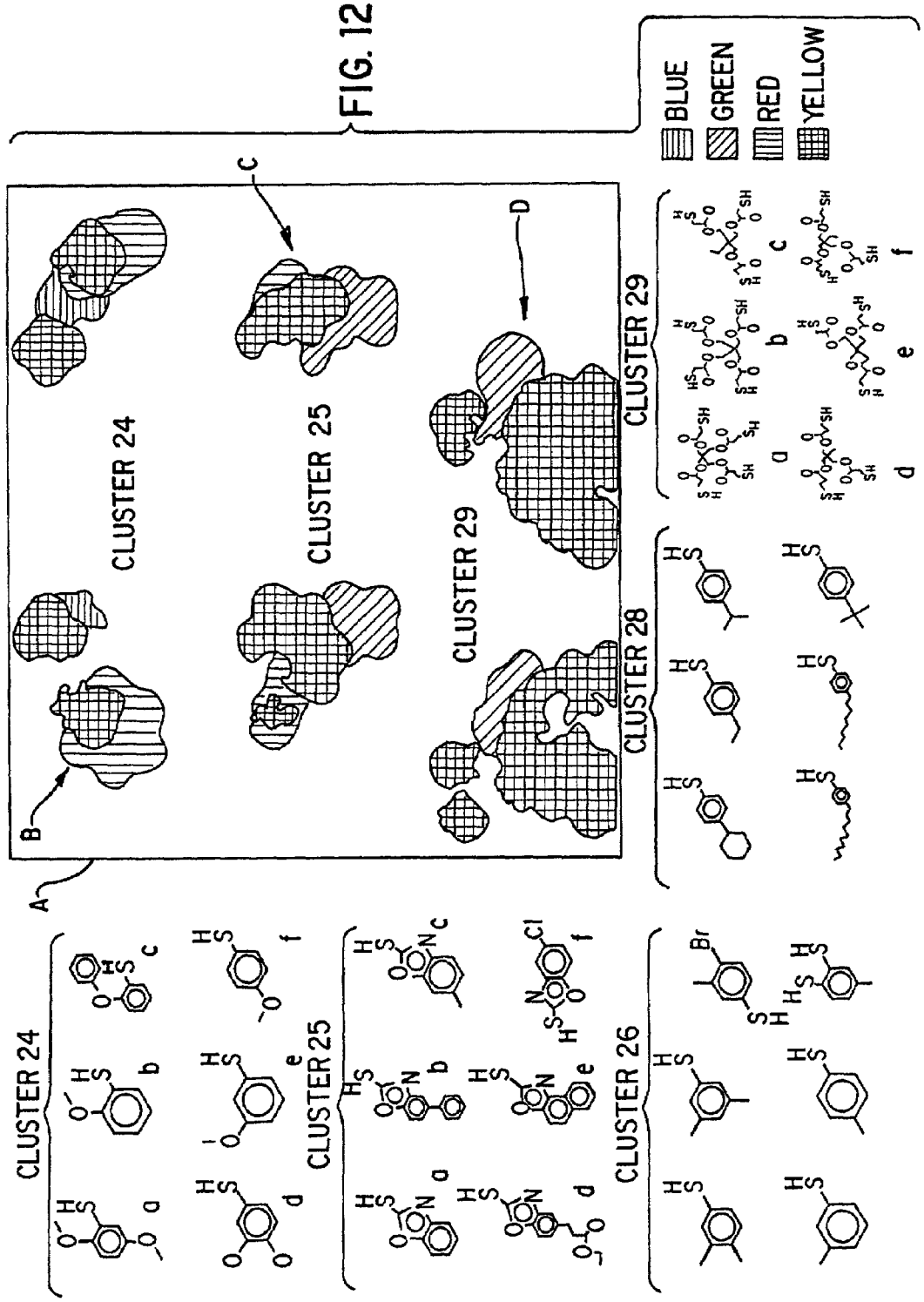
FIG. 12 shows a comparison of the volumes of space occupied by different molecules which are determined to be similar according to the Tanimoto 2D fingerprint descriptor but which are determined to be dissimilar according to the topomeric CoMFA field descriptor.

A second reason for applying a steric metric to the reactants is that all of the three dimensional variability of the products resulting from a combinatorial synthesis resides in the substituents added by the reactants since the core three dimensional structure is common to all molecules in any particular combinatorial synthesis. In a sense it would be redundant to measure the contribution to each product molecule of a core which is common to all the products. A third reason for applying a three dimensional metric to the reactants is that a sterically sensitive metric distinguishes differences among molecules that are not revealed using other presently known metrics. For instance, the topomeric ComFA metric is more sensitive to the volume and shape of the space occupied by a molecule than is, for instance, either the side chain or whole molecule Tanimoto descriptor. FIG. 12 provides an illustrative example of this feature drawn from the thiol study which confirms what was seen in the Patterson plots of the topomeric CoMFA and Tanimoto whole molecule descriptor. FIG. 12 shows three clusters labeled 24, 25, and 29 for which the Tanimoto whole molecule fingerprint metric does not indicate any substantial difference in molecular structure among the molecules, labeled (a) through (f), maling up each of the clusters. The large panel A in the upper right of FIG. 12 shows orthogonal 3D views of the volume differences within clusters 24, 25, and 29 comparing each of the molecules that are not in the majority steric field cluster. For example, the Cluster 24 figure B at the top shows four contours (yellow, green [hidden], red, and blue) indicating the differences in volumes occupied by compounds 24(a), 24(b), 24(c) and 24(f) compared to compounds 24(d) and 24(e) which are found in the same steric field cluster, number 10. The middle C and bottom D figures in the large panel A show similar distinguishable volume differences for Clusters 25 and 29. While the whole molecule Tanimoto metric does not distinguish much difference between the molecules within each of these clusters, it is readily apparent from FIG. 12, even to an untrained eye, that the molecules in the clusters represent very different types of structural diversity; that is, significantly different three dimensional volumes are occupied by the molecules within each whole molecule Tanimoto determined cluster. The topomeric CoMFA metric clearly shows steric differences that are not indicated by the 2D Tanimoto. As seen earlier, a side chain Tanimoto similarity descriptor also does not distinguish steric differences amongst some molecules. A metric responsive to steric differences is, therefore, clearly preferred as a diversity discriminator for reactants.

The preferred method for selecting reactants based on diversity is shown schematically at the third filter in FIG. 11. A diversity selection based on three dimensional steric measures begins by: 1) generating 3D structures for the reactants; 2) aligning the 3D molecular structures according to the topomeric alignment rules; 3) generating CoMFA steric field values for the reactants including, if desired, hydrogen bonding fields, and applying a rotatable bond attenuation factor; and 4) calculating pairwise topomeric CoMFA differences for every pair of reactants. At this point the steric diversity of the reactant space has been mapped into the topomeric CoMFA metric space. From the validation of the topomeric CoMFA metric, it was found that the neighborhood radius for an apparent activity difference of 2 log units was defined by a distance of approximately 80–100 topomeric CoMFA units (kcal/mole). Therefore, at this point, the method of the invention clusters (using hierarchical clustering) the reactants in topomeric CoMFA space so that reactants having a pairwise difference of less than approximately 80–100 units are assigned to the same cluster. Put another way, clustering is continued until the inter-cluster separation is greater than approximately 80–100 units. (If desired, there is some leeway in choosing the exact neighborhood radius in and about the neighborhood range to use for any given biological system. An experienced practitioner of the clustering art will easily be able to determine, by noting the natural breaks in the clustering, where about the 80–100 range best clustering is obtained.) This process will produce clusters having reactants whose product activities will only rarely differ by more than approximately 2 log units. If reactant clusters having products activities differing by a greater or lesser amount are desired, the neighborhood distance used may be increased or decreased accordingly. The effect on the neighborhood distance of choosing such other activity range can be seen by viewing the Patterson validating plots for the topomeric CoMFA descriptor.

The clustering process now identifies groups (clusters) of reactants having steric diversity from one another but also having the same steric properties within each cluster. Or put in terms familiar to medicinal chemists, the molecules of each cluster should be bioisosters. For purposes of designing a combinatorial screening library which has within it molecules representing the full range of steric diversity present in the universe of reactants, it is now only necessary to select one reactant from each cluster for inclusion in the library. A reasonable way to select the one reactant from each cluster would be to select the lowest priced or most readily available one. However, additional criteria may be considered. The diverse reactants remaining at matrix D need not be adjacent to each other on the combinatorial matrix and are only shown this way for graphic convenience. At this point the first stage of library design has been completed.

While the use of a topomeric CoMFA metric to measure the three dimensional structural diversity of the reactants has been discussed, it should be apparent that any metric: 1) reflective of the three dimensional properties of molecules; and 2) validated as taught above, could be applied to the reactants to be used in a combinatorial synthesis in the manner taught above. The teaching of this invention is not limited to the use of the topomeric CoMFA metric, but also includes the use on reactants of all validated three dimensional metrics. As seen earlier, at the present time initial studies of topomeric hydrogen bonding fields indicate that it should be a very useful metric. For those reactants expected to form large number of hydrogen bonds, this may be the metric of choice. The hydrogen bonding metric would be used as an adjunct to the topomeric CoMFA metric in those situations. There may be situations where a sterically sensitive metric is not needed, in which case it should be clear that any valid metric appropriate to reactants could be used.

C. Identification (Building) of Products

Once the set of diverse reactants has been identified by the above method, the structures of the product molecules can be combinatorially determined based on the synthetic reaction scheme and any desired cores. The reactants are used to build the structures of the combinatorial products using LEGION and are stored in molecular spread sheets. In matrix F the products which can still be built from the available reactants are shown as asterisks in each matrix location.

D. Removal of Products for Non-Diversity Reasons

After the possible product structures have been identified, another opportunity exists to reduce the number of products due to general non-diversity considerations. These considerations will generally be related to the particular chemistry involved and might relate to product instabilities, cyclic structures, etc. (Matrix F)

During the building of the combinatorial product molecules, the size of the product molecules increase and various combinations of core and substituents will affect the likely diffusion of the molecule (and may even form one of the biologically undesirable molecular groupings). Thus, in order to eliminate molecules which would not be used as drugs, the product molecules should be examined with many of the same selection criteria applied to reactants. In particular, molecular weights should be calculated and those compounds which have molecular weights over a predetermined value should be rejected. Typically, a value of 750 is used at this time as a representative weight above which bioavailability may become a problem. In addition, CLOGP should be calculated and any proposed molecule with a value under −2.5 or over 7.5 rejected. The number of structures eliminated at this point will depend in part both on the chemistry involved and the molecular weight range retained at the reactant stage. These additional product structures which are eliminated are reflected in matrix G.

E. Removal of Non-Diverse Products

As noted, a second opportunity based on diversity considerations to reduce the number of molecules to be included in the combinatorial screening library occurs after the products of a proposed combinatorial synthesis have been "built" by the software in the computer. Such an additional reduction is usually necessary since the number of combinatorial products at this stage may still be astronomically large. This is reflected in matrix G. In addition, it makes no sense to screen any more molecules than is absolutely necessary, and redundancy may occur in the products for several reasons. In a simple case, if two diverse reactants may react independently at each of two possible sites on a symmetric core molecule, two identical product molecules will be generated. In a more complex case, it is possible that one combination of core and reactants is similar (due to the similarities of structures contained in the core to the structure of the reactants) to another combination of core and reactants. That is, when the reactants are combined with the core molecule, it is possible that substructures within the core can combine with different substituents to form similar structures. Clearly, it would be redundant to screen both. How to select product molecules has been a vexing problem in the prior art, and this is one reason why the prior art has basically been concerned with clustering criteria. The general approach taken in the prior art to avoid oversampling combinatorial product molecules representing the same diversity has been to cluster the molecules and then maximize the distance between clusters with whatever metric was applied to the products.

Based upon an understanding developed from the theoretical considerations of validating a metric outlined above, the library design method of this invention again makes use of the neighborhood principle to solve this problem. However, it is important to understand that, unlike some methods of the prior art, the method of this invention specifically does not use a metric to cluster product molecules. Rather, the neighborhood definition may be used to decide which product molecules to retain in the final screening library and, correspondingly, when the appropriate number of product molecules have been selected for inclusion in the library. Essentially, starting with one product molecule, additional molecules are selected as far apart as possible (in the validated metric space) from any molecule already in the library until the next molecule to be selected would fall within the neighborhood distance of a molecule already included. Additional molecules are not included because to do so would include two or more molecules within the library representing the same structural diversity. Therefore, the neighborhood principle is used as a sampling rule to insure that molecules representative of the same diversity or otherwise too similar are not included in the library. The resulting combinatorial screening library is not redundant and has not oversampled the diversity space.

In the present invention, the Tanimoto 2D whole molecule similarity coefficient is used for the final product selection. As was seen above, this metric possesses the neighborhood property. Accordingly, from the combinatorial products either a first product is arbitrarily chosen for inclusion in the library or an initial seed of one or more products may be specified. (If an arbitrary product molecule is chosen, Tanimoto coefficients are calculated for all other molecules to the first molecule and a second molecule with the smallest Tanimoto coefficient [greatest distance—least similarity] from the first is chosen for inclusion.) For the efficient selection of additional molecules to be included, the distance (1−Tan. Coeff.) between each additional molecule and all molecules already included in the library is calculated. For each additional molecule, the distance to the closest molecule already in the library is identified. These closest distances for each additional molecule are compared, and the additional molecule whose closest distance is the greatest is selected next for inclusion; that is, the molecule which is farthest away from the closest molecule in the library is selected. A new set of distances is calculated and the process continued, selecting one molecule at a time, until no more molecules remain which are farther away than 0.15 ([1−0.85] the definition of a Tanimoto "distance" using the neighborhood value of 0.85). While this example is presented in terms of the Tanimoto similarity coefficient, any validated whole molecule metric and its neighborhood definition may be used with this sampling procedure.

As noted earlier, the value of 0.85 for the Tanimoto neighborhood definition originally appeared in the sigmoid plots. To confirm whether this is the correct neighborhood definition for the Tanimoto metric, the Patterson plots for the whole molecule Tanimoto in which the $X^2$ indicated significance were used to calculate the neighborhood value. The metric distances corresponding to 2-log and 3-log biological differences were determined by dividing the slope of the density determined line by the values 2 and 3 respectively. Over the data sets, the average metric distance for a 2 log biological difference was 0.14 and the average metric distance for a 3-log biological difference was 0.21. Since the Tanimoto distance of (1−Tan. Coeff.) is plotted in the Patterson plot, these values correspond to a 2-log similarity of 0.86 and a 3-log similarity of 0.79. This confirms the reasonableness of using 0.85 in the sampling process. Also, as discussed earlier, it is reasonable to have more confidence in the definition of the neighborhood derived from the Patterson plots which utilize all the molecular data. As noted with reference to selection of a neighborhood distance using the topomeric CoMFA metric on reactants, there may be a situation where a different biological activity may be appropriate and a correspondingly different neighborhood distance used for product selection.

Figure 13:
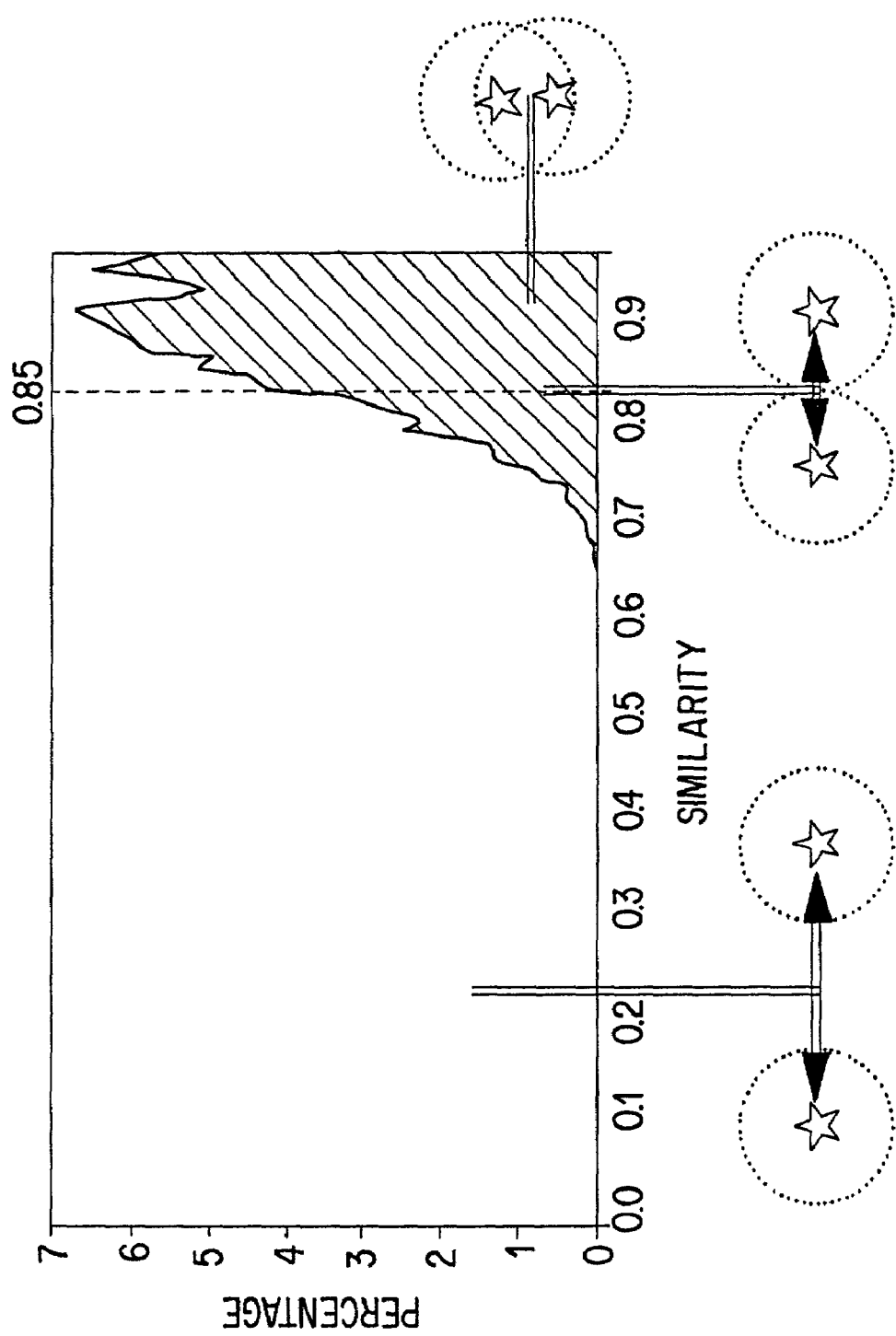
FIG. 13 shows a plot of the Tanimoto 2D pairwise similarities for a typical combinatorial product universe.

Conceptually this selection process is reflected in FIG. 13. FIG. 13 shows a plot of the Tanimoto 2D pairwise similarities for a typical combinatorial product universe in which there has been some selection of reactants based on diversity. As can be seen, a very large percentage of the products have similar structures (Tanimoto coefficients>0.85). The sampling process outlined above results in the following. Molecules having pairwise similarities above approximately 0.85 have overlapping neighborhood radii as shown at 1 and one of each pair is excluded from the library. Molecules having pairwise similarities of approximately 0.85 have almost touching but not overlapping neighborhood radii as shown at 2 and are included in the library. Molecules having pairwise similarities significantly less than approximately 0.85 have no overlapping neighborhood radii as shown at 3 and are also included in the library. Excluding molecules with a Tanimoto similarity greater than 0.85 will eliminate a significant number of molecules in this representative product assembly. This reduction is also reflected in matrix F. While the circles of similarity shown in FIG. 13 represent convenient conceptualizations of the neighborhood distance concept, it should be remembered that most metrics will not define a space in which the "distance" corresponds to an area or volume. In particular, a Tanimoto similarity space does not have this property, yet the "similarity" to a neighbor can be defined and is very useful.

Figure 14:
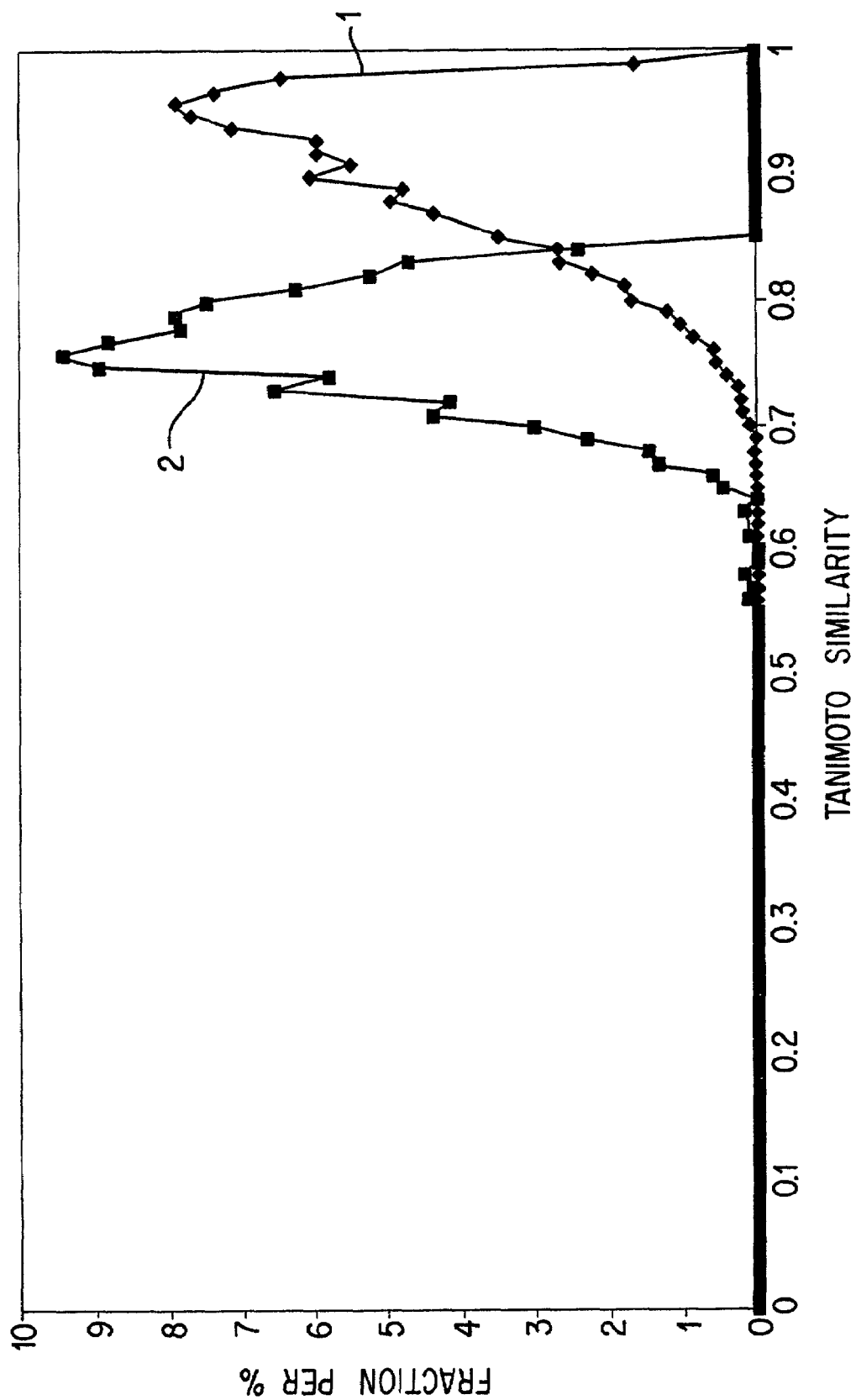
FIG. 14 shows the distribution of molecules resulting from a combinatorial screening library design plotted according to their Tanimoto 2D pariwise similarity after reactant filtering and after final product selection.

A specific example illustrates the dramatic power of the final selection stage in the design process. A proposed combinatorial screening library was designed using thiols and sulfonyl chlorides as reactants. (Many of the same thiols were considered in the study discussed earlier.) The original 716 thiols and 223 sulfonyl chlorides considered would make 159,668 potential products. Topomeric CoMFA analysis indicated that 170 thiols and 61 sulfonyl chloride reactants represented diverse molecules for the purposes of this design and should be used in further library design. 10,370 combinatorial products were now possible. Graph 1 of FIG. 14 shows the Tanimoto similarity distribution of the 10,370 possible products. It can be seen that a large percentage of the possible products were at least 0.85 similar to each other. Following the final stage selection process of the method of this invention, 1,656 product molecules were selected none of which was 0.85 similar to the other. Graph 2 of FIG. 14 shows the plot of the Tanimoto similarities of the final library design products. (The Y axis of the graph is plotted in fraction per % so that the integrated totals are proportional to 10,370 and 1,656 respectively.) The remarkable selectivity of the sampling process is immediately apparent. The products of the designed library have a clearly different similarity profile than the non-selected products. In addition, there has been a greater than 6:1 reduction in the number of product compounds. Thus, from a possible universe of 159,668 potential combinatorial products, 1,656 have been identified which represent the structural diversity of the large ensemble. An approximate 100:1 reduction has been achieved without sacrificing the diversity of the combinatorially accessible universe. As a result of the library design, only the 1,656 compounds have to be synthesized. In addition, these same 1,656 compounds can be tested in any number of biological assays with a high degree of assurance that even in assays with unknown biological activity requirements, these compounds will present the diversity of compounds accessible through this combinatorial universe to the biological assays. Thus there is not only a savings in time and expense in the synthesis and testing of the identified molecules in the library, but it is not necessary to change library design (with concomitant time and expense) each time it is desired to screen a different biological assay. Over time, using the library design of this invention and the process for merging libraries discussed below, it will be possible to build up an optimally diverse combinatorial screening library based on many different combinatorially accessible universes, and this combined library will represent the first real general purpose screening library available to the art—a realization of a long sought after, and previously believed unattainable, goal.

Clearly, other validated whole molecule metrics and their associated neighborhood distances can be used with the sampling process described above to select product molecules for inclusion in a screening library. However, it makes no sense to use the same metric for the products as was used for the reactants. For instance, in the case of the topomeric CoMFA metric, no information would be gained if the metric was used again with the products since all the steric information from the reactants has been transferred to the products. What is critical is that the combinatorial screening library should be constructed by including product molecules which do not fall within the neighborhood radius of other molecules and excluding product molecules which fall within the neighborhood radius of previously chosen molecules. At the end of the design process of this invention, a list of product structures and the reactant sources for each is available in the computer and can be output either in electronically readable or visually discernable form. This data defines the combinatorial screening library. The list of reactants is supplied to synthetic organic chemists. Actual synthesized molecules are then available for testing in the biological assays, typically on multiple well plates. The list of products from each library design can be used to create a definition of a larger combinatorial screening library when merged with other such libraries as discussed below.

The combinatorial screening library designed by the method of this invention is both locally diverse (no two reactants representing the same steric space are present) and globally diverse (no two products having overall similar structures are present). Such a library thus meets the desired combinatorial screening library criteria of being representative of the diversity of the entire combinatorially accessible chemistry universe while at the same time not containing more than one sample of each diversity present (no oversampling). An optimally diverse combinatorial screening library has thus been achieved. By designing an optimally diverse screening library, a reduction in the number of combinatorially generated structures which need to be synthesized and tested of substantially greater than $10^2$–$10^3$ should be possible.

9. Lead Compound Optimization

Unless an entire combinatorially accessible chemical universe is screened, a lead molecule found from screening a library will rarely be the most active or the optimal molecule desired. Therefore, extensive additional work is usually required searching for a related compound possessing the greatest activity or some combination of activity and another desirable feature such as bioavailability. Most of the time, the design of the screening library from which the compound was identified provides little, if any, help in this search. Again, medicinal chemists must resort to traditional methods of lead development. Combinatorial screening libraries based on the methods of this invention provide the means for a directed search of the chemistry space in a way not possible with prior art libraries.

This feature results directly from the fact that the libraries are constructed at each level by selecting molecules which are representative samples of particular molecular diversities. Thus, once a lead is identified, it is a straightforward matter to identify and test compounds representative of the same and/or closely related diversity; ie., it is known how to identify molecules within the neighborhood of the active lead, as defined by the validated metrics used to construct the screening library. Furthermore, the synthetic chemical methods used to construct the screening library are already known and tested and can be used to synthesize additional molecules of the same or similar molecular structural diversity. Since time is always of the essence, especially in exploring a newly discovered biological target, a rational follow up search through an optimally designed library of this invention permits homing in on crucial molecular structures directly and quickly. Not only does this procedure speed up the development process, but it also avoids wasting the time and effort synthesizing and analyzing large numbers of compounds not in the neighborhood of the lead compound which would be erroneously tried prior to knowledge of this invention.

Because the libraries of this invention have been constructed using two selection steps based on molecular structural differences, each step provides an opportunity to identify and explore compounds having similar structural features.

A. Advantages Resulting From Product Filter

Due to the way the final product molecules were selected for inclusion in the library, all compounds with a Tanimoto similarity of approximately 0.85 or greater to a compound already in the library were excluded. Therefore, the first place to look for compounds likely to have the same activity as the lead compound is in the group of all compounds in the combinatorial universe from which the lead was identified having a Tanimoto coefficient with respect to the lead compound of approximately 0.85 or greater. Then, since each of these initial compounds will also have an associated group of different compounds within approximately 0.85 Tanimoto similarity of themselves, this larger group forms the second layer of what can be an expanding area of similar compounds to investigate. How far outwards from the lead compound the search is carried (each time searching within a Tanimoto coefficient of approximately 0.85) will be determined by the success of these additional compounds showing activity in the same assay as the lead compound. Thus, the library design itself identifies and permits a directed search for compounds from the utilized combinatorial universe most likely to have activity similar to the lead compound. The same procedure is followed if another valid metric, not the Tanimoto similarity) was used to create the library. Then all compounds within the neighborhood distance to a compound already in the library were excluded and the first place to look would be for compounds which fall within the neighborhood distance. The process is exactly identical to that followed using the Tanimoto descriptor.

B. Advantages Resulting From Reactant Filter

Two consequences flow from the selection of only one reactant from each cluster. First, combinatorial products containing that reactant may or may not be the most active with respect to any particular given biological screening test. There is no way to guarantee that the reactant that yields the most active product will be selected from the cluster. For any reasonably sized cluster, the probabilities of finding the reactant that yields the most active product would not be greatly increased even if two reactants from that cluster were chosen, and, the size of the library to be tested would have been doubled.

However, the second consequence of selecting only one reactant from each cluster presents the flip side of the selection coin. Once a lead compound is identified, the library design immediately indicates from which diverse clusters the reactant molecules were chosen. All the other possible reactants (in the combinatorial chemical universe under study) representing similar aspects of diversity are included in the clusters from which the reactants were chosen. For lead optimization, compounds containing the other reactants from the identified cluster(s) can be synthesized and tested. The library design itself assures that the exploration of these reactants is likely to yield compounds with similar activity to the lead compound. Thus the reactant selection process not only reduces the number of molecules that need to be screened, but simultaneously identifies the molecular structures which should be subsequently explored to find the compound with the highest activity similar to the identified lead. No other prior art library design process provides so much information for lead optimization.

C. Additional Optimization Methods Using Validated Metrics

The knowledge that a metric is valid, and what that implies for the metric space as discussed earlier, immediately enables methods for lead optimization not previously possible. In particular, knowing that a metric will define a design space where compounds with similar biological properties are found measurably near each other (the definition of a valid metric), now permits for the first time the quantitative examination of the array of molecules used in any screening assay to determine whether any molecules are measurably close to the identified lead compound. One aspect of this approach has already been discussed in sections 9.A and 9.B and certainly works best with an optimal library designed by the method of this invention. In addition, however, validated metrics will permit useful examination of any assemblage of compounds whether or not the lead compound is identified from within the assemblage. There is no restriction on the source of the additional compounds to be examined and they may range from prior art screening libraries to chemical databases. Once a lead is identified, a validated metric would be used to map the lead and all other compounds in the assemblage to be examined into the metric space; ie, the metric characteristics/values are determined for all possible compounds. For reactants (possible substituents) a metric validated on reactants would be used. For whole molecules, a metric validated on whole molecules would be used. Metric differences between the lead molecule and all the other molecules would then be calculated. All molecules with metric distances to the lead within the neighborhood distance of the validated metric should have similar biological activities. Again, if the metric distances from each molecule thus identified as falling within the neighborhood distance of the lead are then calculated with respect to all other molecules (excluding the lead and each other), a second layer of molecules is identified which should have activity similar to the active neighbors of the lead molecule. Additional layers may be similarly identified and explored experimentally. Depending on the structures involved, at least two layers would normally be explored. Thus, because validated metrics are now available, lead optimization will much less often be the hit or miss procedure characteristic of the prior art.

An extension of this procedure yields yet another major advance. In the prior art it was not possible to tell how far away from the lead (in structural terms) one should explore in the search for a compound more active than the lead. In terms of the two dimensional activity island analogy of FIG. 1, no procedure existed for exploring the shape or extent of the island of activity. Without knowledge of the island's shape and extent, not only was it impossible to know by how far a compound missed the island, but even when an active compound was found, it was also not possible to know if the island had been sufficiently explored; that is, whether all compounds representing the range of diversity spanned by the activity island had been identified. In other words, had everyplace been explored that should have been?

With the molecules identified by the expansion procedure outlined above, it will now be possible to map the island. Starting with molecules within the neighborhood distance of the lead, molecules would be synthesized and tested for activity. If all the molecules within the neighborhood distance ("nearest neighbors") show activity, each still falls within the boundary of the island, and the next layer of molecules in the neighborhood distance expansion would be synthesized and tested. If only some of the nearest neighbor molecules show activity, the neighborhood radius of the lead must span an edge of the activity island, and only molecules falling within the neighborhood distance of these nearest neighbor active molecules would be included in the next layer of the expansion and synthesized and tested. Again, some of the newly tested molecules may show activity and some may not. This process of nearest neighbor molecule identification and testing should be repeated until no molecule in the next expansion layer shows any activity. The active molecules determined by this procedure will define the limits and shape of the activity island in terms of structural differences.

The resolution obtainable with this procedure depends upon how well the structural diversity of the activity island is represented by the molecules in the original assemblage. That is, if only a portion of the activity island structural diversity is represented in the assemblage of molecules, that is the only part of the island which can be explored.

Alternatively, perhaps only the island's rough outline can be perceived. Within the constraints of the diversity present in the assemblage, exploration of the full extent of the island and of the space within its boundaries can be accomplished with the guidance of the validated metric with which the island is mapped. To explore the island further it is only necessary to identify molecular structures not included within the original assemblage with which to test the unknown territory. In some cases in order to distinguish particular structural differences, it may be necessary to consider additional sources of structurally diverse molecules and, perhaps, to map the lead and additional compounds in more than one metric space. Thus, possible structures can be proposed and examined with the validated metric. If the proposed structures fall within the neighborhood distance of an active molecule, they can be experimentally tested. If those are active, further structures can be proposed and again examined to determine whether they fall within the neighborhood distance of the newly identified active molecule. If they do, they would be experimentally tested. Repeating this cycle of identification and testing will ultimately yield a higher resolution map of the island and assure the searcher that the island has been thoroughly explored and no activity peak has been missed.

The availability of validated metrics enables yet another method of rationally directed lead optimization from a knowledge of the structure of a lead molecule which was not identified from screening an optimally diverse combinatorial screening library. Essentially, the reactant screening process is utilized backwards to identify similar molecular structures, and then the product screening process is utilized to confirm structural similarity of proposed products to the lead. Two cases are important. The first involves lead molecules which can be synthesized directly from reactants. In this method, the lead molecule would be analyzed to determine from what constituent reactants it may be synthesized. These reactants would then be characterized using a reactant metric such as topomeric CoMFA. Molecules in databases of potential reactants would be characterized using the reactant metric and searched for reactants falling within the neighborhood radius of each of the original reactants. The identified reactants will provide a basis for building proposed products having the same structural characteristics (diversity) as the original lead compound. However, before the product is synthesized, its similarity in metric space to the lead would be checked using a product appropriate metric to make sure that it falls within the neighborhood radius of the lead.

The second case involves lead compounds in which substituent groups are bonded to a central or core molecule. The reactants which form the basis of the substituents as well as the core molecule would then be characterized using appropriate validated metrics. Again, molecules in databases of possible reactants and core molecules would be characterized with validated metrics and searched for molecules falling within the neighborhood radius of each of the original reactants and core. The molecules thus identified would provide a basis for building proposed products with structural diversity similar to the lead compound. Again, before synthesis, the proposed products would be evaluated with an appropriate metric to confirm that they fall within the neighborhood distance of the lead compound.

Since it is known that molecules resulting from different chemistries and involving different constituents often show activity in the same biological assay, it would be desirable to search as wide a range of molecules as possible when performing the searches outlined above to identify additional molecules that are within the neighborhood distance of some lead compound. Clearly, when contemplating these procedures, it must be recognized that the universe of all accessible chemical substances, even under the constraints of molecular weight that characterize a useful drug, numbers trillions of structures. While such unprecedented directed searches are only now possible with validated metrics, even with today's powerful computers, the practicality of such large searches depends on preorganizing the trillions of candidate structures in such a way that the vast majority of candidates can be excluded, to the greatest extent possible, at the start of the search.

One such useful preorganization involves dividing the candidates into series of molecules accessible by some common synthetic route, and thus describable in terms of a core and reactants. (Typically, the synthetic route used to create the lead would be the first investigated and other sets of alternative routes explored secondarily.) A combinatorial SYBYL Line Notation (cSLN) affords a useful description of such a series of molecules.

Molecules represented by a cSLN would be considered for overall similarity to an active lead molecule in the manner discussed above. Using validated metrics, it is most efficient to: 1) first identify each of the individual lists of reactants within the cSLN with the most similar side chain within the active lead; 2) next, to consider the similarity of the "core" within the lead (the atoms remaining after the side chains are identified) to the non-variant core within the cSLN; and 3) then, if the "core" similarity is not so low that this series of molecules can immediately be excluded, to order the variation lists by similarity to the corresponding side chains within the lead. The advantage of such a partitioning and preordering by similarity is the ability to break off the search as soon as no remaining member of the series would be likely to be sufficiently similar.

As an overly simplistic example, consider the series of sixteen possible dihalogenated methanes which may be represented by a cSLN as: X2CH2X1{X1:F|Cl|Br|I}\{X2:F|Cl|Br|I}.) If bromobenzene were the "active lead" and the dihalomethanes were the series to be considered, an appropriate metric that indicated the lack of similarity of the aromatic core of bromobenzene to the methylene core of the dihalomethanes would immediately eliminate all dihalomethanes without considering each of the sixteen individual possibilities. However, if ethyl bromide were the "active lead", an appropriate metric might show that the methylene and ethylene moieties were sufficiently similar to warrant consideration of the individual methylene dihalides, and preordering of the variation list might immediately lead to dibromomethane as the most similar dihalomethane to ethyl bromide (the first bromine atom being identical to the ethyl bromide bromine, and the second bromine atom probably being the most similar to the $CH_3$ of the ethyl bromide). In this hypothetical example only one molecule instead of sixteen would need to be considered in identifying similar molecules most likely to lie within the same neighborhood as the lead. Within actual cSLNs (each possibly representing perhaps millions of structures by including more points of variation and many more and larger variations at each point), the speed enhancement obtainable from this searching strategy would be many orders of magnitude greater than sixteen.

There may be other variations of the applications of the methods outlined above which are not yet recognized at the present time since the concepts and applications of this invention are still so new. However, reasonable extrapolations/techniques of molecular discovery which follow from the disclosure of the present invention and, in particular, from the ability to validate metrics, are considered within the teaching of this application.

10. Merging Libraries

The final selection (sampling) methodology of this invention has broader uses than yet described. So far, this disclosure has been primarily concerned with the design of a combinatorial screening library based upon either sets of reactants or sets of reactants and central cores. Each combinatorial screening library based on these materials only explores the diversity of that part of the chemical universe accessible with those compounds. Unless as much of the diversity of the entire combinatorially accessible chemical universe is explored in a screening library as is possible, there is no assurance that a molecule possessing activity with respect to any particular unknown biological assay will be found. Clearly, the useful diversity of the combinatorially accessible chemical universe can only be explored with as many sets of reactants attached to as many cores as is possible. Stated slightly differently, there may be large parts of the diversity of the chemical universe not explored by one or even a few combinatorial schemes. Thus, combinatorial screening libraries based on multiple reactants and multiple cores would be desirable. However, even with screening libraries constructed with the method of this invention, the simple addition to each other of many such libraries will quickly increase the total number of molecules which need to be screened. Worse yet, since many of the possible reactants used for combinatorial synthesis with different cores have similar structures, and since many of the possible cores used for combinatorial synthesis may differ little from each other, it is highly likely that much of the same diversity is represented to a greater or lesser extent in each of the libraries generated from these materials. Simply combining the libraries would again result in oversampling of the same diversity space. It would clearly be more useful and economical (efficient) in terms of time, money, and opportunity to use additional screening to explore different aspects of the diversity of the chemical universe.

Another significant feature of this invention is the recognition that the neighborhood selection (sampling) criteria also provides a method to combine combinatorial screening libraries to avoid this oversampling problem. Starting with an arbitrary first library, using a validated metric which can be applied to whole molecules, each molecule of a second library is added to the first library if the molecule does not fall within the neighborhood radius of any molecule in the first library as supplemented by all the added molecules from the second library. This process is continued until all the molecules in the second library have been examined. In this manner, only molecules representative of a different aspect of diversity are added from the second library to the first. Each successive library is added in the same manner. The molecules in a final combined library formed from smaller libraries selected according to the method of this invention represent diverse molecular compounds and have the optimal diversity which is desired of a general combinatorial screening library. However, even if the groups of molecules to be merged have not been selected by the methods of this invention, they may be merged according to the above procedure if first, a subset of each group of molecules is selected according to the product sampling method of the design process. This will insure that similar molecules within each group are eliminated. The resulting merged library will not be optimally diverse, but it should not redundantly sample the diversity present in the separate groups.

Figure 15:
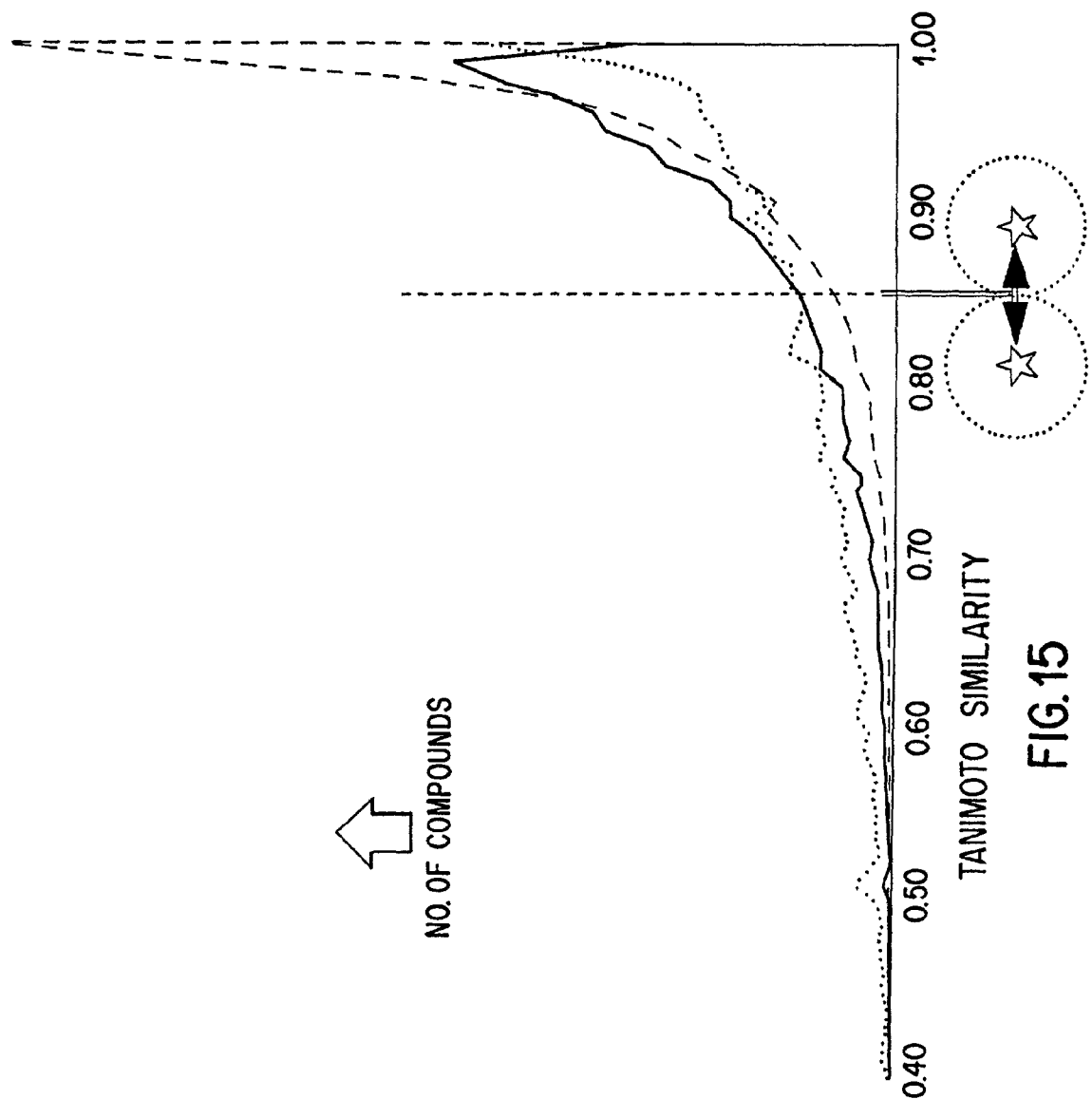
FIG. 15 shows the distribution of molecules plotted according to their Tanimoto 2D pairwise similarity of three database libraries (Chapman & Hall) from the prior art.

The 2D Tanimoto fingerprint metric is useful in performing the library additions. The 2D Tanimoto similarity coefficient of each molecule in the first library to all molecules in a subsequent library are calculated. Each molecule of the second library is added to the first library if the molecule does not fall within a 0.85 Tanimoto coefficient (the neighborhood radius) of any molecule in the first library as supplemented by all the added molecules from the second library. As long as the metric used for sampling and endpoint determination is valid (has the neighborhood property), this selection method guarantees a combined library in which all of the accessible diversity space is represented with little likelihood of oversampling. An example of three prior art libraries not designed with the method of this invention which might be merged using the neighborhood sampling criteria is shown in FIG. 15. FIG. 14 shows the distribution of molecules plotted according to their Tanimoto 2D pairwise similarity of the Chapman & Hall Dictionary of Natural Products, Dictionary of Pharmacological Agents, and Dictionary of Organic Compounds (CD ROM Versions). It is immediately clear from FIG. 14 that simply adding the three libraries together would produce a combined library in which most of the compounds would be very similar to each other (Tanimoto similarities>0.85). Further redundant similarity would be expected from a comparison of the similarities between the molecules in the three libraries! The position of the 0.85 similarity point to the bulk of the molecules in each library indicates that, most of the molecules in these databases would be excluded from a combined library formed by merging the databases by the procedure outline above.

11. Other Advantages of Optimally Diverse Libraries

There are additional benefits achieved by designing combinatorial libraries according to the method of this invention. For instance, as noted earlier, one of the difficulties of screening several compounds simultaneously is the possibility of non-specific activity being detected due to the contributory effect of the combination of compounds. In fact, the likelihood of this effect is increased when compounds of the same molecular structural and chemical diversity are tested in the same assay. With the libraries of this invention, it will be possible to design the assay combinations so that only compounds representing different aspects of diversity are tested together. While this procedure can not guarantee that no combination effects will occur, it makes it much less likely. Another benefit achieved is that complex deconvolutions will generally be unnecessary. Deconvolution problems are accepted in the prior art as a necessary evil due to the enormous number of molecules which must be synthesized and screened since virtually all combinatorial possibilities are included in the libraries. Clearly, with smaller optimally diverse combinatorial screening libraries covering the same search territory as the larger prior art libraries, it is possible with the aid of computer controlled robots and data bases to individually synthesize and track each compound.

As mentioned at the beginning of this disclosure, the methods of this invention are also applicable to problems outside the specific area of drug research. The notion of choosing compounds based on diversity is a general concept with many applications and is applicable any time the problem is presented of having more compounds than can usefully be tested/used. The example was given earlier of determining what compounds had the same structural diversity as a previously identified (biologically active) compound. Of course, with the methods of this invention, the activity may be any chemical activity. In addition, the universe of chemicals from which only some are to be selected does not have to result from a combinatorial synthesis, but may result from any synthesis or no synthesis at all. An example of the later would be the solution to the question of selecting molecules of similar diversity from among those in a large corporate or catalog data base. In these cases, an appropriate metric (remembering that different metrics are applicable in different circumstances) would be applied to all the compounds and clustering would result in compounds of the same diversity. The methods of this invention, including metric validation, topomeric CoMFA metric characterization, end-point neighborhood sampling, lead compound optimization, and library design can all be applied separately and together to solve the selection problem.

Thus, while this invention has been particularly described with reference to the drug lead identification art, it is clear that the validation of molecular structural descriptors and their use in selecting structurally diverse sets of chemical compounds can be applied anywhere a large number of compounds is encountered from which a representative subset is desired. Since the implications and advances in the art provided by the methods of this invention are still so new, the entire range of possible uses for the methods of this invention can not be fully described at the present time. However, such as yet identified uses are considered to fall under the teachings and claims of this invention if validated molecular structural descriptors are employed to characterize the diversity of molecules.

REFERENCES CITED

1. Seligmann, B. (1995) *Synthesis, Screening, Identification of Positive Compounds and Optimization of Leads from Combinatorial Libraries: Validation of Success*, p. 69–70. Symposium: "Exploiting Molecular Diversity: Small Molecule Libraries for Drug Discovery", La Jolla, Calif. Jan. 23–25, 1995 [conference summary available from Wendy Warr & Associates, 6 Berwick Court, Cheshire, UK CW4 7 HZ]
2. Johnson, M. and Maggiora, G. (Editors) *Concepts and Applications of Molecular Similarity*, John Wiley, New York, 1990
3. Martin, E., Blaney, J., Siani, M., Spellmeyer, D., Wong, A., and Moos, W. (1995) *Measuring Diversity: Experimental Design of Combinatorial Libraries for Drug Discovery*. J. Med. Chem. 38, 1431–1436
4. Martin, E., Blaney, J., Siani, M. and Spellmeyer, D. (1995) *Measuring diversity: Experimental design of combinatorial libraries for drug discovery*. Abstract, ACS Meeting, Anaheim, Calif. COMP 32, and Martin, E. (1995) *Measuring Chemical Diversity: Random Screening or Rationale Library Design*, p. 27–30. Symposium: "Exploiting Molecular Diversity: Small Molecule Libraries for Drug Discovery", La Jolla, Calif. Jan. 23–25, 1995 [conference summary available from Wendy Warr & Associates, 6 Berwick Court, Cheshire, UK CW4 7 HZ]
5. Brown, R., Bures, M., and Martin, Y. (1995) *Similarity and cluster analysis applied to molecular diversity*. Abstract, ACS Meeting, Anaheim, Calif. COMP 3
6. Herndon, W. (1995). *Similarity and Dissimilarity of Molecular Structures*. p. 25–27. Symposium: "Exploiting Molecular Diversity: Small Molecule Libraries for Drug Discovery", La Jolla, Calif. Jan. 23–25, 1995 [conference summary available from Wendy Warr & Associates, 6 Berwick Court, Cheshire, UK CW4 7 HZ]
7. Chapman, D. and Ross, M. (1994) Poster at the symposium: "Chemical and Biomolecular Diversity", San Diego, Calif. Dec. 14–16, 1994, and Ross, M. (1995) *Assessing Diversity (Or Lack Of It) in Chemical Libraries*. p. 63–65. Symposium: "Exploiting Molecular Diversity: Small Molecule Libraries for Drug Discovery", La Jolla, Calif. Jan. 23–25, 1995 [conference summary available from Wendy Warr & Associates, 6 Berwick Court, Cheshire, UK CW4 7 HZ]
8. Cramer, R., Redl, G., and Berkoff, C. (1974) *Substructural Analysis: A Novel Approach to the Problem of Drug Design*. J. Med. Chem. 17, 533
9. U.S. Pat. No. 5,025,388 (1988) and Cramer, Patterson, D., and Bunce, J. (1988) *Comparative Molecular Field Analysis (CoMFA). Effect of Shape on Binding of Steroids to Carrier Proteins*. J. Am Chem. Soc. 110, 5959–5967
10. Kubinyi, H. Editor (1993) *3D QSAR in Drug Design, Theory, Methods, and Applications*. ESCOM, Leiden, Holland
11. Dean, P. Editor (1995) *Molecular Similarity in Drug Design*. Chapter 12, Kim, K. *Comparative molecularfield analysis* (ComFA). p. 291–324. Chapman & Hill, London, UK
12. Y. Martin, M. Bures, E. Danaher, J. DeLazzer, I. Lico, P. Pavlik (1993) *A Fast Approach to Pharmacophore Mapping and its Application to Dopaminergic and Benziodiazepine Agonists*. J. Comp.-Aid. Mol. Des. 7, 83–102
13. P. Willett, V. Winterman (1986) *A comparison of some measures for the determination of intermolecular structural similarity*. Quantitative Structure-Activity Relationships 5, 18–23
14. R. P. Sheridan, R. B. Nachbar, B. L. Bush (1994) *Extending the trend vector: The trend matrix and sample-based partial least squares*. J. Comp.-Aid. Mol. Des. 8, 323–340
15. G. Moreau, P. Broto (1980) (no title given). Nouv. J. Chim. 4, 757–7644
16. L. B. Kier, L. H. Hall (1976) *Molecular Connectivity in Chemistry and Drug Research*. Academic press, NY

APPENDIX A

The following sections of code accomplish two tasks:

I) Calculation of the topomeric conformation for a particular molecule, assuming that the molecule is referenced by a particular row of a Tripos Molecular Spreadsheet (MSS). With minor adaptations this code could be used in other molecular modeling environments, such as Cerius 2, Quanta, or Insight.

II) Calculation of the line slope assuming that the biological data and one or more columns of property data are stored in a Tripos Molecular Spreadsheet (MSS). Almost any other software for manipulating data in a spreadsheet or other tabular representation could be adapted to perform similar calculations, assuming a Tanimoto function for expressing "distances" between bitsets of equal cardinality.

Both sections of code include procedures written in two languages. The first is C, familiar to all programmers, and includes both all specialized structure declarations and also brief explanations of all functions used. The second is SPL, an interpretative language available within the SYBYL molecular modeling program, whose syntax is similar to a Unix shell script. The SPL language is described fully in the volume entitled <u>SPL Manual</u>, found within the documentation set for SYBYL 6.2, release date July 1995. This volume includes descriptions of all "expression generators" (functions returning a value) and "macro commands" not specifically explained below.

I. Topomeric Field Code:
    A. SPL macro *CHOM!BUILD3D*. To build topomerically aligned 3D models, the third argument must have the value ALIGN, and the global associative array element CHOM!Align[ALICYC] must have the value All_trans. Code to allow user adjustment of these and other 3D model-building parameters appearing in this code as other elements of CHOM!Align[] is not shown.
    B. Under these circumstances the following SPL macro *CHOM!Alltrans* sets all torsions provided to their topomeric values.
    C. To determine the atoms defining each torsion to be adjusted, *CHOM!Alltrans* invokes the expression generator %trans_path(), which executes the following C subroutine *SYB_MGEN_CONN_BEST*, with its associated subroutines *syb_mgen_conn_att_atoms*,

*get_path_mw*, *get_path_xyz*, and (if debugging) *ashow*. No user-adjustable values are used by this code. All non-obvious include files and a brief functional description of subroutines external to this code are provided in section III below.

D. The computation of rotatable-bond-attenuated steric (and/or electrostatic, hydrogen bonding) fields for the topomerically aligned conformation is carried out by the C subroutine *QSAR_FIELD_EVAL_RB_ATTEN*, which uses the accompanying subroutine *QSAR_FIELD_RB_WTS* to generate an attenuated weight for each atom's contribution to the field(s). (Pseudo code for the latter subroutine appears in its header comment.) The attenuation factor (recommended value of 0.85) is a user-adjustable or "tailorable" value, here shown as COMFA!AGGREG_SCALING. The user-adjustable HBOND_RAD_SCALING parameter affects the steric "radius" of a hydrogen-bonding hydrogen.

II. Patterson-Distribution Validation Code

A. The SPL expression generator *lrt_fast* returns the slope of the "best" line along with the count of data points and the fractional area, within a "virtual" or conceptual graph of absolute differences in biological activities vs absolute differences in the diversity measurement to be validated. The format of its output appears in the header comment.

B. The short SPL expression generator *dochi* shows the computation of the chi-squared statistic resulting from the output of the lrt_fast expression generator.

C. The C code functions *QSHELL_HIER_LRT*, *QSHELL_HIER_DO_LRT*, and *fpt_heapsort* generate the results produced by lrt_fast. These routines generate the biological differences themselves but rely on some external procedure, not shown, to generate the distances between the diversity measurements. (The reason is that the method of calculating differences depends on the diversity parameter(s). Typically a Euclidean distance is calculated for scalar properties, or a Tanimoto difference is calculated for bitsets, and if multiple parameters are combined to form the diversity measurement to be validated then the relative weighting must also be specified by the user.)

Section III. Supporting information for interpretation of the C code in Sections I and II.

A. Declarations of complex and non-standard data structures referenced by the declarations within these C procedures, specifically for molecules, atoms, and the regions, fields, and other user input information that are part of a CoMFA field description.

B. Functional descriptions of all external subroutines called by these C procedures, ordered alphabetically.

```

# SECTION I-A. Macro BUILD_3D for generating and storing topomeric alignments

#========================================================================
@macro BUILD_3D CHOM
# builds 3D models,
#     storage in a database or in a conformer column

#     either not-aligned (just uses Concord or as-is if from Unity,
#         or minimizes input structure)
#     or aligned for CoMFA (requires core structure as alignment template)
#         with optional fixup of side chains, charge calculation
#   $1 is row ids in current MSS
#   $2 is storage code (will retrieve structure from same place or somewhere)
#   $3 is align (U or A)
#   $4 is basic building technique
# other arguments, used only if ALIGN is true, are elements
of the global associative array CHOM!ALIGN set up mol retrieval from MSS to be fast and clean localvar AFFECT_SUBSET_save
localvar EXAMINE_TAILOR_MODE_save
localvar HIGHLIGHT_MSS_save
localvar INFORM_save
localvar INPUT_MODE_save
localvar RELATE_save
localvar SHOW_MOLECULE_save
localvar USER_FUNCTION_save natmcore heavy ys
localvar align ma rid cgq_save tailor_bumps_save newc \
         a b max_save usehs rat yrat nrat noth setvar AFFECT_SUBSET_save        $TAILOR!EXAMINE!AFFECT_SUBSET
setvar EXAMINE_TAILOR_MODE_save  $TAILOR!EXAMINE!EXAMINE_TAILOR_MODE
setvar HIGHLIGHT_MSS_save        $TAILOR!EXAMINE!HIGHLIGHT_MSS
setvar INFORM_save               $TAILOR!EXAMINE!INFORM
setvar INPUT_MODE_save           $TAILOR!EXAMINE!INPUT_MODE
setvar RELATE_save               $TAILOR!EXAMINE!RELATE
setvar SHOW_MOLECULE_save        $TAILOR!EXAMINE!SHOW_MOLECULE
setvar USER_FUNCTION_save        $TAILOR!EXAMINE!USER_FUNCTION
setvar cgq_save $CGQ_TIMEOUT
set CGQ_timeout 0 setvar TAILOR!EXAMINE!AFFECT_SUBSET         NONE
setvar TAILOR!EXAMINE!EXAMINE_TAILOR_MODE   SILENT
setvar TAILOR!EXAMINE!HIGHLIGHT_MSS         NO
setvar TAILOR!EXAMINE!INFORM                NO
setvar TAILOR!EXAMINE!INPUT_MODE            ROW_COLUMN_EXPR
setvar TAILOR!EXAMINE!RELATE                NO
setvar TAILOR!EXAMINE!SHOW_MOLECULE         YES
setvar TAILOR!EXAMINE!USER_FUNCTION         NONE
setvar max_save $TAILOR!MAXIMIN2!LS_STEP_SIZE $TAILOR!MAXIMIN2!MAXIMUM_ITERATION setvar ma %table_attribute( MOL_AREA )

if needed make new place to put output
setvar newc
switch %substr( $2 1 3 )
case NEW)
   setvar newc %math( %table( * COL COUNT ) + 1 )
```

```
   table column sln %cat( CONF $newc )
;;
case SYB)
   database open %qspr_table_db( %table_default() ) update
   table ATTRIBUTE SET CONFORMER 0
;;
case )
   setvar newc %substr( $2 1 %math( %pos( _ $2 ) - 1 )
   TABLE CONFORMER $newc
;;
endswitch if %streql( %substr( $3 1 1 ) "A" )
are we bump checking ?
   if $CHOM!Align[BUMPS]
      setvar tailor_bumps_save $TAILOR!GENERAL!bumps_contact_distance
      tailor set general bumps_contact_distance %math( $CHOM!Align[BUMPS] - 1.0 )
   endif

# STEP 1: prepare template fragment

   setvar mcore $CHOM!Align[ MCORE ]
# save original template
   setvar mcsav %molempty()
   copy $mcore $mcsav default $mcore >$nulldev
   if $CHOM!Align[DEBUG]
      label id *
    endif
    setvar capsln %cat( %sln( $mcore ) )
    setvar natcore %mol_info( $mcore NATOMS )

# IF the alignment template has just one free valence,
# make geometrically acceptable template by adding heavy atoms, minimizing
# else use as is
   setvar heavy TRUE
   fillvalence *-H* Hal >$nulldev
   if %gt( %math( %mol_info( $mcore NATOMS ) - $natcore ) 1 )
      copy $mcsav $mcore
      setvar heavy
   endif
   if $heavy
    for a in %atoms(<H*>-<H>)
      modify atom type $a C.3   >$nulldev
      modify atom name $a X1 >$nulldev
    endfor
   endif
   TAILOR SET MAXIMIN2 LS_STEP_SIZE 0.0001 MAXIMUM_ITERATIONS 1000 | |
   MAXIMIN $mcore DONE INTERACTIVE >$nulldev if $heavy
   for a in %atoms(X1)
      modify atom type $a HEV    >$nulldev
# must rename it !!
      modify atom name $a X1 >$nulldev
   endfor setvar ys %set_create( %atoms(X1) )
orient template so that an R points in the positive X direction
```

A-5

```
    setvar rat %arg( 1 %set_unpack( $ys ) )
    setvar nrat %arg( 1 %atom_info( $rat NEIGHBORS ) )
    setvar yrat %arg( 1 %set_unpack( %set_diff( \
        %set_create( %atom_info( $nrat NEIGHBORS ) ) $rat ) ) )
    ORIENT USER $nrat $rat $yrat >$nulldev
endif identify all the non-primary atoms for FIT, in/out of the search pattern
and all the basic torsions (bonds to Ys) that potentially need setting
    setvar tpat %arg( 1 %search2d( %cat( %sln( $mcore ) ) $capsln NoDup 0 y ) )
    setvar hvinpat
    setvar patats
    setvar tors
    setvar usehs
    setvar sybhvats %set_create(%atoms(*-<H>))
    if %lt( %set_size( $sybhvats ) 3 )
        setvar usehs TRUE
        setvar sybhvats %set_create(%atoms(*))
    endif for a in %range(1 %sln_atom_count( $capsln ) )
        if %or( "$usehs" "%not( %set_and( %sln_atom_symbol( $capsln $a ) \
                H,F,Cl,Br,I ) )" )
# for FIT, need to know the SYBYL IDs of the heavy atoms
            setvar hvinpat $hvinpat $a
            setvar patats[ $a ] %sln_rgroup_sybid( $mcore $tpat $a )
            setvar patats[ $a ][ YS ] %set_and( "$ys" "%set_create( \
                %atom_info( $patats[ $a ] NEIGHBORS ) )" )
# for each torsion root, need to save the SLN ID of an arbitrary
#          heavy atom torsional definer
            if $patats[ $a ][ YS ]
                setvar tors[ $a ] %set_and( %set_diff( "%set_create( \
%atom_info( $patats[ $a ] NEIGHBORS ) )" $patats[ $a ][ YS ] ) $sybhvats )

# if there are several possibilities, prefer the lowest #'d carbon
#                to define trans-ness
                if %gt( %set_size( $tors[ $a ] ) 1 )
                    if %set_and( $tors[ $a ] %set_create( %atoms(<C*>) ) )
                        setvar tors[ $a ] %set_and( $tors[ $a ] \
                            %set_create( %atoms(<C*>) ) )
                    endif
                    setvar tors[ $a ] %arg( 1 %set_unpack( $tors[ $a ] ) )
                endif
                for a1 in %range(1 %sln_atom_count( $capsln ) )
                    if %eq( $tors[ $a ] %sln_rgroup_sybid( $mcore $tpat $a1 ) )
                        setvar tors[$a] $a1
                        break
                    endif
                endfor
            endif
        endif
    endfor
if $CHOM!Align[DEBUG]
 echo %prompt( INT 1 " " " " )
endif
endif default $ma >$nulldev
setvar CHOM!BadRows
```

```

#              build 3D models

# off we go !! Get MSS row IDs to build models for
if %streql( $1 * )
   setvar rids %table( * ROW NUM )
else
   setvar rids %set_unpack( $1 )
endif for rid in $rids get the next MSS entry to be modelled
   table examine $rid | | >$nulldev fix NO2's (egad what a pain) because Concord & SYBYL are inconsistent
   setvar pat %search2d( %sln( $ma ) N(=O)O ALL 0 y )
   while $pat
      setvar pat %sln_rgroup_sybid( $ma %arg( 1 $pat ) 1 3 )
      modify bond type %bonds( %cat( %arg( 1 $pat ) "=" \
                %arg( 2 $pat ) ) )   2 >$nulldev
      modify atom type %arg( 2 $pat ) o.2
      setvar pat %search2d( %sln( $ma ) N(=O)O ALL 0 y )
   endwhile if $CHOM!Align[DEBUG]
     label id *
   endif basic optimization
   switch $4
case CONCORD)
   CONCORD MOL $ma >$nulldev
# if Concord failed, we may still be awfully flat
# minimize if there are heavy atoms not part of a single aromatic system ..
      setvar noth %atoms( *-<H> )
      setvar a1 %arg( 1 $noth )
      if %set_diff( "%set_create( $noth )" \
         "%set_create( %atoms( %cat( "{aromatic(" "$a1" ")}" ) ) )" )
         setvar zs %extent_3d( %cat( $ma "(*)" )
         setvar zs %math( %arg( 5 $zs ) - %arg( 6 $zs ) )
         if %eq( $zs 0.0 )
            %unflatten( %cat( $ma "(*)" ) )
            MAXIMIN $ma DONE INTERACTIVE
         endif
      endif
;;
case MINIMIZE)
    MAXIMIN $ma DONE INTERACTIVE >$nulldev
;;
   endswitch done, if only 3d coord, but for topomeric CoMFA ..
   if %streql( %substr( $3 1 1 ) "A" )
# find any arbitrary 2D hit
      setvar pat %search2d( %cat( %sln( $ma ) )  $capsln NoDup 0 y )
      if %not( $pat )
         setvar CHOM!BadRows %set_or( "$CHOM!BadRows" $rid )
         echo $capsln not found in molecule for Row $rid .. skipping
         goto next1
```

A-7

```
        endif
        setvar pat %arg(1 $pat )
        setvar allpatats %set_create( %sln_rgroup_sybid( $ma $pat \
            %range( 1 %sln_atom_count( $capsln ) ) ) )

# collect all appropriate heavy atoms for FIT and torsions
        setvar mat1
        setvar mat2
        setvar schns
        for a in $hvinpat
            setvar mat1 $mat1 $patats[ $a ]
            setvar sybat %sln_rgroup_sybid( $ma $pat $a )
            setvar mat2 $mat2 $sybat
# are there heavy atom neighbors to FIT also (and generate torsion lists)?
            if $patats[$a][YS]
                setvar ans %set_diff( %set_create( \
                    %atom_info( $sybat NEIGHBORS ) ) $allpatats )
                setvar ans %atoms($ans-<H>)
                setvar i 1
                for p in %set_unpack( $patats[$a][YS] )
# add heavy atom neighbors to FIT list
                    if %arg( $i $ans )
                        setvar mat1 $mat1 $p
                        setvar mat2 $mat2 %arg( $i $ans )
# generate another torsion for CHOM!alltrans
                        setvar schns $schns %cat( $sybat "," \
%sln_rgroup_sybid( $ma $pat $tors[ $a ] ) "," %arg( $i $ans ) )

endif
                    setvar i %math( $i + 1 )
                endfor
            endif
        endfor setvar dofit MATCH %cat( $mcore "(" %set_create( $mat1 ) ")" ) \
            %cat( $ma "(" %set_create( $mat2 ) ")" )
        $dofit >$nulldev
if $CHOM!Align[DEBUG]
    echo %prompt( INT 1 " " " " )
endif do FIT
    if %gt( $MATCH_RMS $CHOM!Align[ FITRMS ] )
        setvar CHOM!BadRows %set_or( "$CHOM!BadRows" $rid )
        echo Bad geometric alignment (MATCH_RMS = $MATCH_RMS) for Row $rid .. sk
        goto next1
    endif
# side chain alignments ..
    switch $CHOM!Align[ ALICYC ]
case User_Macro)
        $CHOM!Align[ ALIDATA ] $ma $CHOM!ALIGN[ MCORE ]
;;
case All_trans)
case With_Templates)
        setvar nojrings TRUE
        setvar rbds %set_create( %bonds({rings()}) )
        for i in $schns
            setvar jbds %set_unpack( $i )
# can set "side chain" bonds only if connecting bond is not cyclic
            if %set_and( "$rbds" "%bonds( %cat( %arg( 3 $jbds ) = \
```

A-8

```
                        %arg( 1 $jbds ) ) )" )
                setvar nojrings
            else
                CHOM!AllTrans $jbds
            endif
          endfor
if $CHOM!Align[DEBUG]
  echo %prompt( INT 1 " " " " )
endif
        if %streql( $CHOM!Align[ ALICYC ] With_Templates )
            setvar f %open( $CHOM!Align[ ALIDATA ] "r" )
            setvar buff %read( $f )
            setvar slnma %cat( %sln( $ma ) )
            while $buff
# each line of text should have pattern, SLN IDs for the 4 torsion atoms,
#       and a torsion value to set
                if %eq( %count( $buff ) 5 )
                    setvar torpat %search2d( $slnma %arg( 1 $buff ) NoDup 0 y )
                    for t in $torpat
                        MODIFY TORSION %sln_rgroup_sybid( $ma $t %arg( 2 $buff ) \
            %arg( 3 $buff ) %arg( 4 $buff ) ) %arg( 5 $buff ) >$nulldev endfor
                endif
            endwhile
            %close( $f )
        endif
;;
    endswitch
  endif do a bump check?
  if $CHOM!Align[BUMPS]
      if %atoms({bumps(*,*)})
          setvar CHOM!BadRows %set_or( "$CHOM!BadRows" $rid )
          echo Bad steric contacts in aligned conformer for Row $rid .. skipping
          goto next1
      endif
  endif
# partial charges ..
  switch $CHOM!Align[ CHARGE ]
case None)
;;
case User_Macro)
    exec $CHOM!Align[ CHARGEDATA ] $ma
;;
case )
    CHARGE $ma COMPUTE $CHOM!Align[ CHARGE ] | >$nulldev
;;
  endswitch put conformer away
  switch %substr( $2 1 3 )
case SYB)
    database add $ma r >$nulldev
;;
case )
    %wcell( $rid $newc %cat( %cat( %sln( $ma FULL CHARGE ) ) ) ) >$nulldev
;;
  endswitch
```

A-9

```
    echo Built row $rid
nextl:
endfor if %streql( %substr( $3 1 1 ) "A" )
    copy $mcsav $mcore
    zap $mcsav
endif if $CHOM!Align[BUMPS]
    TAILOR SET GENERAL bumps_contact_distance $tailor_bumps_save | |
endif
done, restore initial EXAMINE settings set CGQ_TIMEOUT $cgq_save
setvar TAILOR!EXAMINE!AFFECT_SUBSET          $AFFECT_SUBSET_save
setvar TAILOR!EXAMINE!EXAMINE_TAILOR_MODE    $EXAMINE_TAILOR_MODE_save
setvar TAILOR!EXAMINE!HIGHLIGHT_MSS          $HIGHLIGHT_MSS_save
setvar TAILOR!EXAMINE!INFORM                 $INFORM_save
setvar TAILOR!EXAMINE!INPUT_MODE             $INPUT_MODE_save
setvar TAILOR!EXAMINE!RELATE                 $RELATE_save
setvar TAILOR!EXAMINE!SHOW_MOLECULE          $SHOW_MOLECULE_save
setvar TAILOR!EXAMINE!USER_FUNCTION          $USER_FUNCTION_save
TAILOR SET MAXIMIN2 LS_STEP_SIZE %arg( 1 $max_save ) \
        MAXIMUM_ITERATIONS %arg( 2 $max_save ) | | update row and column information if %streql( %substr( $2 1 3 ) NEW )
make any new conformer column become the source of molecules
    TABLE CONF %table( * COL COUNT )
    CHOM!UPDATE_ROW_SEL $CHOM!CID_Last
    setvar CHOM!CID_Last %math( $CHOM!CID_Last + 1 )
else
    CHOM!UPDATE_ROW_SEL
endif

.

# Section I-B. Generates the topomeric conformation of the 3D model

#=========================================================================
@macro ALLTRANS chom
# assumes default molecule, takes argument atoms $1 and $2
# where $1 is the JOINed atom of the core, $2 is the atom that
#   the rest of the substituent is to be trans to,
#   and $3 is the JOINed atom of the substituent
# starts from that atom and sets all side chains
to a topomeric conformation localvar bds b bdset a1 a2 tmp sbonds sats rbond pbds torsion ringbonds doit check input for legality
    setvar tmp %set_create( %atom_info( $1 NEIGHBORS ) )
    if %not( %eq( 2 %count( %set_unpack( %set_and( \
            "$tmp" %cat( $2 "," $3 ) ) ) ) ) )
        echo Bad input to ALLTRANS (atoms $2 $3 not bonded to $1)
        return
```

A-10

```
     endif save key bonds
     setvar rbond %bonds( %cat( $3 "=" $1 ) )
     setvar sats %conn_atoms( $3 $1 )
     if %not( $sats )
#       echo No substituent atoms found in ALLTRANS
       return
     endif setvar sats $3 $sats
     setvar sbonds %set_create( %bonds( \
         %cat( "{TO_ATOMS(" %set_create($sats) ")}" )) )

# define the other bonds that might need adjusting
     setvar bds %set_create( %bonds( (*-{RINGS()})&<1> ) )
     setvar bds %set_and( "$sbonds" "$bds" )
     if %not( $bds )
        return
     endif
# discard bonds to primary atoms
     setvar mval %set_create( %atoms( \
         <H>+<o.2>+<F>+<I>+<Cl>+<Br>+<n.1>+<LP>+<Du> ) )
     setvar pds %set_create( %bonds( %cat( "{TO_ATOMS(" $mval ")}" ) ) )
     setvar bds %set_diff( $bds $pds )
     setvar ringbonds %set_create(%bonds({RINGS()}) )

# walk all the important bonds
 for b in %set_unpack( $bds )
     setvar doit TRUE
# if this is the JOIN bond, already have some info
     if %eq( $b $rbond )
       setvar a0 $2
       setvar a1 $1
       setvar a2 $3
# still need to be SURE we're not monovalent
       if %or( "%eq( 1 %count( %atom_info( $a1 NEIGHBORS ) ) )" \
           "%eq( 1 %count( %atom_info( $a2 NEIGHBORS ) ) )" )
         setvar doit
       endif
     else
       setvar bdat %bond_info( $b ORIGIN TARGET )
       setvar a1 %arg( 1 $bdat )
       setvar a2 %arg( 2 $bdat )
       if %or( "%eq( 1 %count( %atom_info( $a1 NEIGHBORS ) ) )" \
           "%eq( 1 %count( %atom_info( $a2 NEIGHBORS ) ) )" )
         setvar doit
       endif
       if $doit
# which end leads to root atom? if necessary flip a1,a2 to make that one be a1
         if %set_and( "%set_create( %conn_atoms( $a2 $a1 ) )" $1 )
            setvar tmp $a1
            setvar a1 $a2
            setvar a2 $tmp
         endif
         setvar a0 %trans_path( $a1 $a2 $1 )
       endif
     endif
     if $doit
       setvar a3 %trans_path( $a2 $a1 )
```

A-11

```
    switch %count( %set_unpack( "%set_and( "$ringbonds" \
        %set_create( %bonds( %cat( $a0 "=" $a1 "," $a2 "=" $a3 ) ) )" ) )
case 0)
        setvar torsion 180
;;
case 1)
        setvar torsion 90
;;
case 2)
        setvar torsion 60
;;
    endswitch
    modify torsion $a0 $a1 $a2 $a3 $torsion >$nulldev
   endif
 endfor /* Beginning of section I-C, C code implementing the trans_path expression gener /*E+:SYB_MGEN_CONN_BEST*/
/****************************************************************
* int SYB_MGEN_CONN_BEST( identifier, nargs, args, writer )      *
*       Dick Cramer, Apr. 9, 1995 (written for SELECTOR use)     *
*                                                                *
* Expression generator that returns the atoms attached to a given *
*       atom, excepting the second, in a prioritized order.      *
* If there are two arguments, the ordering is by decreasing branch *
*       "size", where "size" is first any path with rings encountered, then
* number of attached atoms, then MW (paths in cycles end when an atom
* in another path is encountered.)
*    If three arguments, the atom that is returned is the one that
* begins the shortest path containing the atom referred to by the
* third argument. If multiple such paths, ordering is same as for
* two arguments.
*    Further prioritization of paths is by molecular weight,
*       and then by lowest X, Y, Z values.
*    If last argument is DEBUG, all paths are written to stdout.
*
* User interface:
*    %trans_path( a1 a2 ( a3 ) (DEBUG)  )
****************************************************************/ int SYB_MGEN_CONN_BEST( identifier, nargs, args, Writer )
/* following arguments contain the text supplied to the %trans_path()
   expression generator, and provide an avenue for producing text output. */
char    *identifier;
int     nargs;
char    *args[];
PFI     Writer;
{ define MAX_NP 8 struct pathrec {
          int root, nrings, chosen, nats;
          float mw, xyz[3];
          set_ptr path;
        } ;

struct pathrec p[MAX_NP];
```

```
                int retval, i, np, toroot, a1, a2, a4, a, pnow, pdone, growing,
                    final_pos, area_num, new_rings, nats, nuats, elem, ncycles,
                    best, debug, ringclosed;
                List_Ptr    atom_exp_list=NIL,SYB_EXPR_ANALYZE();
                mol_ptr     m1, m2, SYB_AREA_GET_MOLECULE();
                atom_ptr    arec, SYB_ATOM_FIND_REC();
/* A set_ptr data structure is a Boolean set, first word containing
its cardinality. */
                set_ptr     atom_set1=NIL, a2chk = NIL, nuls = NIL, cnats = NIL,
                    nxcn = NIL, end_atoms = NIL, scratch = NIL,
                    SYB_ATOM_FIND_SET(), UTL_SET_CREATE();
                char        tempString[256];
                float       get_path_mw(), diff;
                void        get_path_xyz();

retval = 0;
                /* Check the number of arguments */
                if ( nargs < 2 || nargs > 4 ) {
                        UIMS2_WRITE_ERROR(
                            "Error: %trans_path requires 2 to 4 arguments\n" );
                        return 0;
                }
                np = 0;
                debug = (!UTL_STR_CMP_NOCASE( args[ nargs - 1], "DEBUG" ));
                toroot = (debug && nargs == 4) || (!debug && nargs == 3);

/* PARSE THE INPUT */

/* get first atom */
    if (!(atom_exp_list = SYB_EXPR_ANALYZE( SYB_EXPR_GET_ATOM_TOKEN, args[0],
        &final_pos, &area_num )))
        goto error;

if (!(m1 = SYB_AREA_GET_MOLECULE (area_num)))
        goto cleanup;
    if (!(atom_set1 = SYB_ATOM_FIND_SET ( m1, atom_exp_list)))
        goto error;
    if( atom_exp_list)
        SYB_EXPR_DELETE_RPN_LIST( atom_exp_list);
    atom_exp_list = (List_Ptr) NIL;

if(!(1 == UTL_SET_CARDINALITY(atom_set1))) {
            UIMS2_WRITE_ERROR(
                "Error: First argument must be only one atom\n");
            goto error;
    }
    if (!(arec = SYB_ATOM_FIND_REC (m1, UTL_SET_NEXT (atom_set1, -1)) )) goto er
    a1 = arec->recno;
    UTL_SET_DESTROY( atom_set1 );
    atom_set1 = NIL;
/* get 2nd atom */
    if (!(atom_exp_list = SYB_EXPR_ANALYZE( SYB_EXPR_GET_ATOM_TOKEN, args[1],
        &final_pos, &area_num ).))
        goto error;

if (!(m2 = SYB_AREA_GET_MOLECULE (area_num)))
        goto cleanup;
    if (!(end_atoms = SYB_ATOM_FIND_SET ( m2, atom_exp_list)))
        goto error;
```

```
        if( atom_exp_list)
              SYB_EXPR_DELETE_RPN_LIST( atom_exp_list);

atom_exp_list = (List_Ptr) NIL;

if (m1 != m2 ) {
                    UIMS2_WRITE_ERROR(
                      "Error: atoms must be in the same molecule\n");
                    goto error;
        }
        if(!(1 == UTL_SET_CARDINALITY(end_atoms))) {
                    UIMS2_WRITE_ERROR(
                      "Error: Second argument must be only one atom\n");
                    goto error;
        }
        if (!(arec = SYB_ATOM_FIND_REC (m1, UTL_SET_NEXT (end_atoms, -1)) )) goto er
        a2 = arec->recno;

/* get 3rd atom */
  if (toroot) {
        if (!(atom_exp_list = SYB_EXPR_ANALYZE( SYB_EXPR_GET_ATOM_TOKEN, args[2],
              &final_pos, &area_num )))
          goto error;

if (!(m2 = SYB_AREA_GET_MOLECULE (area_num)))
           goto cleanup;
        if (!(atom_set1 = SYB_ATOM_FIND_SET ( m2, atom_exp_list)))
           goto error;
        if( atom_exp_list)
              SYB_EXPR_DELETE_RPN_LIST( atom_exp_list);

atom_exp_list = (List_Ptr) NIL;

if (m1 != m2 ) {
                    UIMS2_WRITE_ERROR(
                      "Error: atoms must be in the same molecule\n");
                    goto error;
        }
        if(!(1 == UTL_SET_CARDINALITY(atom_set1))) {
                    UIMS2_WRITE_ERROR(
                      "Error: Second argument must be only one atom\n");
                    goto error;
        }
        if (!(arec = SYB_ATOM_FIND_REC (m1, UTL_SET_NEXT (atom_set1, -1)) )) goto er
        a4 = arec->recno;

UTL_SET_DESTROY( atom_set1 );
        atom_set1 = NIL;
  }
/* GENERATE the paths */

/* set up paths */
        if (!(a2chk = UTL_SET_CREATE( m1->max_atoms + 1 ) )) goto error;
        if (!(nuls  = UTL_SET_CREATE( m1->max_atoms + 1 ) )) goto error;
        if (!(cnats = UTL_SET_CREATE( m1->max_atoms + 1 ) )) goto error;
        if (!(nxcn  = UTL_SET_CREATE( m1->max_atoms + 1 ) )) goto error;
        if (!(scratch = UTL_SET_CREATE( m1->max_atoms + 1 ) )) goto error;

if (!syb_mgen_conn_att_atoms( a2chk, m1, a1 )) goto error;
        if (!UTL_SET_MEMBER( a2chk, a2 )) {
```

A-14

```
            UIMS2_WRITE_ERROR (
               "Error: second argument atom is not bonded to first argument atom/\n")
            goto error;
      }
      UTL_SET_DELETE( a2chk, a2 );
      a = -1;
      np = 0;
      while (np < MAX_NP && (a = UTL_SET_NEXT( a2chk, a)) >= 0 ) {
         if (!(p[np].path = UTL_SET_CREATE( m1->max_atoms + 1 ) )) goto error;
         p[np].root = a;
         p[np].nrings = 0;
         UTL_SET_INSERT( p[np].path, a );
         np++;
      }
/* grow the paths */
      growing = TRUE;
      nats = 0;
      ncycles = 0;
      while (growing ) {
         nuats = 0;
         ringclosed = FALSE;
         for (pnow = 0; pnow < np; pnow++ ) {
            UTL_SET_COPY_INPLACE( cnats, p[pnow].path );
            UTL_SET_CLEAR( nxcn );
            elem = -1;
/* accumnulate this generation of attached atoms into nxcn */
            while ( (elem = UTL_SET_NEXT( cnats, elem)) >= 0 ) {
               UTL_SET_CLEAR( nuls );
               if (!syb_mgen_conn_att_atoms( nuls, m1, elem )) return( FALSE );
               UTL_SET_DELETE( nuls, a1 );
               UTL_SET_DIFF_INPLACE( nuls, end_atoms, nuls );

UTL_SET_OR_INPLACE( nxcn, nuls, nxcn );
               UTL_SET_DIFF_INPLACE( nxcn, p[pnow].path, nxcn );
            }
            UTL_SET_OR_INPLACE( p[pnow].path, nxcn, p[pnow].path );
/* remove and mark ring closures when growing out */
            if (!toroot) for (pdone = 0; pdone < np; pdone++ ) if (pdone != pnow) {
               UTL_SET_AND_INPLACE( p[pnow].path, p[pdone].path, a2chk );
               if ((new_rings = UTL_SET_CARDINALITY( a2chk ))) {
/* we have ring closure(s) */
                  p[pnow].nrings += new_rings;
                  p[pdone].nrings += new_rings;
                  ringclosed = TRUE;
                  UTL_SET_OR_INPLACE( end_atoms, a2chk, end_atoms );
/* if pdone < pnow, two branches are now same lengths, drop common atom from bot
      but if >, branches are different, and must avoid repeated closing */
                  if (pdone < pnow) {
/* remove atom(s) in the previous branch because paths are really same length
                     UTL_SET_DIFF_INPLACE( p[pdone].path, a2chk, p[pdone].path );
                     UTL_SET_DIFF_INPLACE( p[pnow].path, a2chk, p[pnow].path );
                  }
                  else {
/* must identify and mark each atom in nxcn that is attached to a2chk atom */
                     elem = -1;
                     while ( (elem = UTL_SET_NEXT( a2chk, elem)) >= 0 ) {
                        UTL_SET_CLEAR( scratch );
                        if (!syb_mgen_conn_att_atoms( scratch, m1, elem ))
                              return( FALSE );
                        UTL_SET_AND_INPLACE( scratch, nxcn, scratch );
```

```c
                    UTL_SET_OR_INPLACE( end_atoms, scratch, end_atoms );
                }
            }
        }
    }
/* done growing paths if no more atoms added to any path .. */
        for (pdone = 0, nuats = 0; pdone < np; pdone++ )
                nuats += UTL_SET_CARDINALITY( p[pdone].path );
        if (nuats<=nats && !ringclosed) growing = FALSE;
        nats = nuats;
/* .. or looking for the 4th atom and found it .. */
        if (toroot) for (pdone = 0; pdone < np; pdone++ )
            if (UTL_SET_MEMBER( p[pdone].path, a4 )) growing = FALSE;
/* .. or after 100 atom layers out regardless */
        ncycles++;
        if (ncycles >= 100) growing = FALSE;
    }
/* debugging */
    if (debug) for (pdone = 0; pdone < np; pdone++) {
        sprintf( tempString, "Path %d (%d rings, from %d): ",
            pdone+1, p[pdone].nrings, p[pdone].root );
        UBS_OUTPUT_MESSAGE( stdout, tempString );
        ashow( p[pdone].path, m1 );
    }
/* compute the path properties */
    for (pdone = 0; pdone < np; pdone++) {
 /* mark as already chosen any path that can't be an answer */
        p[pdone].chosen = toroot && !UTL_SET_MEMBER(p[pdone].path, a4);
        p[pdone].nats = UTL_SET_CARDINALITY( p[pdone].path );
        p[pdone].nrings = p[pdone].nrings ? 1 : 0;
        p[pdone].mw = 0.0;
        p[pdone].xyz[0] = p[pdone].xyz[1] = p[pdone].xyz[2] = 0.0;
    }
/* return the best result */
    best = 0;
    for (pdone = 1; pdone < np; pdone++) {
        if (toroot) {
            if (p[best].chosen && !p[pdone].chosen) best = pdone;
/* looking backward along chain, always grow away from more negative coord value
            if (!p[best].chosen && !p[pdone].chosen) {
                get_path_xyz( p[pdone].root, m1, p[pdone].xyz );
                get_path_xyz( p[best].root, m1, p[best].xyz );
                for ( i = 0; i < 3; i++ ) {
                    diff = p[pdone].xyz[i] - p[best].xyz[i];
                    if (diff < -0.1) {
                        best = pdone;
                        break;
                    }
                    if (diff > 0.1 ) break;
/* checking other coords if basically tied at this coord */
                }
            }
        }
        else {
           if (p[pdone].nrings && !p[best].nrings) best = pdone;
           else if (p[pdone].nats > p[best].nats) best = pdone;
           else if (p[pdone].nats == p[best].nats) {
            p[pdone].mw = get_path_mw( p[pdone].path, m1, p[pdone].mw );
            p[best].mw = get_path_mw( p[best].path, m1, p[best].mw );
```

```
            if (p[pdone].mw > p[best].mw) best = pdone;
         }
      }
   }
   arec = SYB_ATOM_FIND_REC( m1, p[best].root );

sprintf(tempString,"%d", arec->id );
   if(!(*Writer)(tempString)) goto error;

retval = TRUE;
error:
cleanup:
   if( atom_exp_list)
         SYB_EXPR_DELETE_RPN_LIST( atom_exp_list);
   if(atom_set1)
         UTL_SET_DESTROY(atom_set1);
   if(end_atoms)
         UTL_SET_DESTROY(end_atoms);
   if(a2chk)
         UTL_SET_DESTROY(a2chk);
   if(nuls)
         UTL_SET_DESTROY(nuls);
   if(nxcn)
         UTL_SET_DESTROY(nxcn);
   if(cnats)
         UTL_SET_DESTROY(cnats);
   if(scratch)
         UTL_SET_DESTROY(scratch);

return( retval );
} static int syb_mgen_conn_att_atoms( aset, m, atid )
/* ors atoms attached to atm into aset */
/* WORKS STRUCTLY WITH RECNOS */
set_ptr aset;
mol_ptr m;
int atid;
{
   atom_ptr at, SYB_ATOM_FIND_ID();
   List_Ptr tohs, UTL_LIST_RETRIEVE_P();
   atom_ptr toh, SYB_ATOM_FIND_REC();
   acon_ptr conn1;
   int nbytes1;

at = SYB_ATOM_FIND_REC( m, atid );
   tohs = at->conn_atom;
   while (tohs) {
         tohs = UTL_LIST_RETRIEVE_P( tohs, &conn1, &nbytes1);
         toh = SYB_ATOM_FIND_REC( m, conn1->target );
         UTL_SET_INSERT( aset, toh->recno );
   }
   return( TRUE );
} static float get_path_mw( aset, m, mw )
/* returns the total atomic weight of all atoms in aset */
set_ptr aset;
mol_ptr m;
float mw;
```

```
{
  int elem = -1;
  float ans = 0.0;
  atom_ptr at, SYB_ATOM_FIND_REC();
  fpt SYB_ATAB_ATOMIC_WEIGHT();

if (mw) return( mw );
  elem = -1;
  while ( (elem = UTL_SET_NEXT( aset, elem)) >= 0 ) {
     at = SYB_ATOM_FIND_REC( m, elem );
     ans += (float) SYB_ATAB_ATOMIC_WEIGHT( at->type );
  }
  return( ans );
} static void get_path_xyz( aid, m, mw )
/* returns the xyz of the supplied atom */
int aid;
mol_ptr m;
float mw[3];
{
  int i;
  atom_ptr at, SYB_ATOM_FIND_REC();

if (mw[0]) return;
  at = SYB_ATOM_FIND_REC( m, aid );
  for (i = 0; i < 3; i++) mw[i] = at->xyz[i];
  return;
} static int ashow( aset, m )
/* for interactive debugging, shows a set's membership in terms of atom ID */
set_ptr aset;
mol_ptr m;
{
    char buff[1000], *b;
    atom_ptr at, SYB_ATOM_FIND_REC();
    int elem;

*buff = '/0';
    b = buff;
    elem = -1;
    while ( (elem = UTL_SET_NEXT( aset, elem)) >= 0 ) {
         at = SYB_ATOM_FIND_REC( m, elem );
         sprintf( b, " %d", at->id );
         b = buff + strlen( buff );
    }
    sprintf( b, "\n" );
    UBS_OUTPUT_MESSAGE( stdout, buff );
}

/* BEGINNING OF SUBROUTINES I-D. Calculation of attenuated fields */

/*+E:QSAR_FIELD_EVAL_RB_ATTEN()*/
/**********************************************************************/
/*                                                                    */
/* int QSAR_FIELD_EVAL_RB_ATTEN( molp, stfldp, elfldp, regp, no_st, no_el, ctp ) */
/*                                                                    */
/* Dick Cramer    May 13, 1995                                        */
/*                                                                    */
```

A-18

```
/*
       "Standard CoMFA" -- except that the contribution of any atom
       to the field falls off with an inverse power of its distance
       from a root atom, measured in NUMBER OF ROTATABLE BONDS!
           This means also that each individual atom's contribution
       has a similarly scaled upper bound, rather than checking
       the upper bound only for the sum over all atoms.
*/
/* This procedure computes vdW 6-12 steric values at each point in region   */
/* and the electrostatic interactions (initially assuming 1/r dielectric).  */
/*                                                                          */
/*  NOTE:: initially ignoring space averaging, other user knobs.            */
/*  note:: assuming valid input here; error checking higher up !            */
/*                                                                          */
/*                                                                          */
/* Input:                                                                   */
/*    molp     - molecule pointer, molecule to place in region.             */
/*    stfldp   - steric field pointer, where values will be placed.         */
/*    elfldp   - electrostatic field pointer, where values will be placed.  */
/*    regp     - region pointer, locations where values are to be evaluated.*/
/*    no_st    - flag to skip steric evaluations                            */
/*    no_el    - flag to skip electrostatic evaluations                     */
/*    ctp      - ComfaTopPtr, for dummy/lp values                           */
/*                                                                          */
/* Returns 0 on failure, 1 otherwise.                                       */
/*                                                                          */
/****************************************************************************/
/*+E:QSAR_FIELD_EVAL_RB_ATTEN()*/ int QSAR_FIELD_EVAL_RB_ATTEN ( molp, stfldp, elfldp, regp , no_st, no_el, ctp)
mol_ptr molp;
FieldPtr  stfldp, elfldp;
RegionPtr regp;
int no_st, no_el ;
ComfaTopPtr  ctp;
{
BoxPtr box;
atom_ptr at, SYB_ATOM_FIND_ID();
int pid, b, ix, iy, iz, nat, vol_avg, repulsive ;
fpt *steric, *elect, SYB_ATAB_VDW_RADII() ;
fpt diff, dis, dis2, x, y, z, sum_steric, sum_elect ;
fpt dis6, dis12 , repuls_val, offs[9][3], atm_ste, atm_ele;
fpt *charge, *ctemp, *coord, *ftemp, *wt, scale_vol_avg, atm_steric, atm_elect;
int *atyp , *itemp,  dohbd, dohba, ishbd, retval, dielectric , off, atid;
static fpt hbond_scal;
fpt hbond_A, hbond_B, *AtWts = NIL, *QSAR_FIELD_RB_WTS();
int *HAs, *HDs, *HAp, *HDp; /* sets would be more efficient but slower */
int do_steric, do_elect;
set_ptr hdonor, SYB_HBOND_DONORS(), pset = NIL, aset = NIL;

#define Q2KC 332.0
#define MIN_SQ_DISTANCE 1.0e-4
/* ^^^ any atom within 10-2 Angstroms is hereby zapped !
       this is about it: 10^6 / 10^-24 is close to overflow!   */ ftemp = NIL; ctemp = NIL; itemp = NIL; retval = FALSE; HAs = NIL; HDs = NIL;
    hdonor = NIL;

/* for now, make root atom the one closest to 0,0,0 */
    for (nat = 1; nat <= molp->natoms; nat++) {
```

```
      at = SYB_ATOM_FIND_ID( molp, nat );
      dis2 = at->xyz[0] * at->xyz[0] + at->xyz[1] * at->xyz[1] +
             at->xyz[2] * at->xyz[2];
      if (nat == 1 || dis2 < dis) {
        dis = dis2;
        atid = nat;
      }
   }

/* following is specific to topomeric fields */
 if (!(AtWts = QSAR_FIELD_RB_WTS( molp, atid ) )) goto cleanup;

if (!no_el)
   {dielectric = elfldp->dielectric ;
    vol_avg    = elfldp->vol_avg_type;
    scale_vol_avg = elfldp->scale_vol_avg;
    repulsive  = elfldp->repulsive;
    repuls_val=repexp[repulsive]; elect =   elfldp -> field_value;}
 if (!no_st)
   {vol_avg    = stfldp->vol_avg_type;
    scale_vol_avg = stfldp->scale_vol_avg;
    repulsive  = stfldp->repulsive;
    repuls_val=repexp[repulsive]; steric =   stfldp -> field_value;} if (!(ftemp = (fpt *) UTL_MEM_ALLOC(3*sizeof(fpt)*molp->natoms))) goto cleanup;
 if (!(ctemp = (fpt *) UTL_MEM_ALLOC( sizeof(fpt)*molp->natoms))) goto cleanup;
 if (!(itemp = (int *) UTL_MEM_ALLOC( sizeof(int)*molp->natoms))) goto cleanup;
 if (!(HAs = (int *) UTL_MEM_ALLOC( sizeof(int)*molp->natoms))) goto cleanup;
 if (!(HDs = (int *) UTL_MEM_ALLOC( sizeof(int)*molp->natoms))) goto cleanup;
/* get just those H's which are capable of Hbonding */
 if (!(hdonor = SYB_HBOND_DONORS( molp, NIL ) )) goto cleanup;

for (coord=ftemp,atyp=itemp,charge=ctemp,HAp=HAs,HDp=HDs, nat=1;
              nat<=molp->natoms;nat++)
   { if (NIL ==(at = SYB_ATOM_FIND_ID(molp, nat) ) ) goto cleanup;
     *coord++  = at->xyz[0];
     *coord++  = at->xyz[1];
     *coord++  = at->xyz[2];
     *atyp++   = at->type -1 ;
     *charge++ = at->charge;
     *HAp++    = SYB_ATAB_HBOND_ACCEPT(at->type) ;
     *HDp++    = UTL_SET_MEMBER(hdonor, at->recno) ;
   }
 for (b=0; b<regp->n_boxes; b++) {
   box = & regp->box_array[b];
   dohbd = (SYB_ATAB_ATOMIC_NUMBER( box->atom_type) == 1) &&
           (box->pt_charge == 1.0);
   dohba = (SYB_ATAB_ATOMIC_NUMBER( box->atom_type ) == 8) &&
           (box->pt_charge == -1.0);
   if (dohbd || dohba) {
       if (!TAILOR_STORE_IT_HERE( "TAILOR!FORCE_FIELD!HBOND_RAD_SCALING",
                  &hbond_scal, 1)) goto cleanup;
       hbond_A = pow( hbond_scal, 6.0 );
       hbond_B = hbond_A * hbond_A;
    }
   if (vol_avg)
     QSAR_FIELD_EVAL_GETOFF(offs,box->stepsize,vol_avg,scale_vol_avg);
   if ( !no_st )
     QSAR_FIELD_VDWTAB ( box -> atom_type, repuls_val, ctp->du_lp_steric );
   for (iz=0, z=box->lo[2] ; iz < box->nstep[2]; iz++, z += box->stepsize[2])
```

```c
      for (iy=0, y=box->lo[1] ; iy < box->nstep[1]; iy++, y += box->stepsize[1])
        for (ix=0, x=box->lo[0] ; ix < box->nstep[0]; ix++, x += box->stepsize[0])
        {
          for ( coord = ftemp, charge = ctemp, atyp = itemp, HAp=HAs, HDp=HDs,
                do_steric=TRUE, do_elect=TRUE, nat=0, sum_steric = sum_elect = 0.0,
            nat<molp->natoms;
            nat++, wt++)
          {
            if ( ( *atyp == DUMMY-1 || *atyp == LP-1 ) && !ctp->du_lp_elect )
              *charge = 0.0;   /* set charge to 0 since ignoring Du/lp */
            if (!vol_avg) /* the "normal" case */
            {
              dis2 =  x - *coord++ ;
              dis2 *= dis2;
              diff =  y - *coord++ ;
              diff *= diff;
              dis2 += diff;
              diff =  z - *coord++ ;
              diff *= diff;
              dis2 += diff;
              if ( !no_el && elfldp->zap_el==2 && do_elect)  {
                 dis = sqrt( dis2 );
                 if ( dis < SYB_ATAB_VDW_RADII( *atyp+1 ) )  {
/* no shortcircuits! */
/*
                   *elect++ = 0.0;
                   do_elect = FALSE;
*/
                 }
              }
              if ( dis2 < MIN_SQ_DISTANCE ) {
                 if ( !no_st )
                   /* if atom has no steric value, we don't care about
                      MIN_SQ_DISTANCE since it has no contribution anyway */
                   if ( vdw_a[*atyp] != 0.0 && vdw_b[*atyp] != 0.0 ) {
                     /* set sterics to its max value at current grid pt. */
                     atm_steric = (*wt) * stfldp->max_value;
                   }
                 if ( !no_el && do_elect) {
                    if ( !no_st && !do_steric && elfldp->zap_el ) {
                       *elect++ = DAB_F_MISSING;
                    }
                     else if ( *charge != 0.0 ) {
                       if ( *charge > 0.0 )
                         atm_elect = (*wt) * elfldp->max_value;
                       else atm_elect = (*wt) * -elfldp->max_value;
                    }
                 } if ( !do_elect && !do_steric )
                   break;    /* break out of loop since neither el. or st.
                                need to be calculated for this grid point */

/* setting dis2 to 1 (an arbitrary no.) will prevent a zero
                    divide in the sum_steric or sum_elect calculations below */
                 dis2 = 1.0;
              } if ( ! no_st && do_steric ) {
                dis6 = dis2 * dis2 * dis2;
```

```
          dis12= dis6 * dis6 ;
          if (repulsive)
             dis12 = (repulsive==1) ? dis12 / dis2 : dis12 / dis2 / dis2;
          if (dohbd && *HAp)
                 atm_steric = hbond_B * vdw_b[*atyp]/dis12 -
                              hbond_A * vdw_a[*atyp]/dis6 ;
             else if (dohba && *HDp)
                 atm_steric = hbond_B * vdw_b[*atyp]/dis12 -
                              hbond_A * vdw_a[*atyp]/dis6 ;
             else
                 atm_steric = vdw_b[*atyp]/dis12 - vdw_a[*atyp]/dis6 ;
          HAp++; HDp++;          }
          atm_steric = atm_steric > stfldp->max_value ? stfldp->max_value
                     : atm_steric;
          atm_steric *= (*wt);
         if ( ! no_el && do_elect ) {
          atm_elect = *charge++ /
                         ( dielectric ? sqrt(dis2) : dis2  ) ;
          atm_elect = atm_elect > elfldp->max_value ? elfldp->max_value
                    : atm_elect;
          atm_elect = atm_elect < -(elfldp->max_value) ? -(elfldp->max_value)
                    : atm_elect;
          atm_elect *= (*wt);
          sum_elect += atm_elect;
         }
          atyp++;
          sum_steric += atm_steric;
        }
        else
        { for (off=0;off<9;off++)
        {
        } coord += 3;
        atyp ++   ;
        charge ++ ;
        HAp ++    ;
        HDp ++    ;
            }
        } /* atom loop */
doneatoms:
     if ( do_steric || do_elect ) {
       if (vol_avg) { sum_elect /= 9.0; sum_steric /= 9.0 ; }
       if ( !no_el && do_elect )
        { *elect  = sum_elect * box-> pt_charge * Q2KC  ;
          if ( *elect > elfldp->max_value ) *elect = elfldp->max_value;
          else if ( *elect < - elfldp->max_value ) *elect =
               - elfldp->max_value;
            transform_field(elfldp->max_value,elect,ctp);
            elect ++;
         }
       if ( !no_st && do_steric )
        { *steric = sum_steric ;
          if ( *steric > stfldp->max_value)
          { *steric = stfldp->max_value;
             if (!no_el && elfldp->zap_el==1 ) *(elect-1) = DAB_F_MISSING; }
          transform_field(stfldp->max_value,steric,ctp);
          steric ++ ; }
       }
     } /* points in box loop */
```

A-22

```
    } /* boxes loop */ retval = TRUE;
cleanup:
  if ( itemp) UTL_MEM_FREE( itemp);
  if ( ftemp) UTL_MEM_FREE( ftemp);
  if ( ctemp) UTL_MEM_FREE( ctemp);
  if (HAs) UTL_MEM_FREE( HAs );
  if (HDs) UTL_MEM_FREE( HDs );
  if (hdonor) UTL_SET_DESTROY( hdonor );
  if (AtWts) UTL_MEM_FREE( AtWts );
  if (pset) UTL_MEM_FREE( pset );
  if (aset) UTL_MEM_FREE( aset );
return retval;

#undef Q2KC
#undef MIN_SQ_DISTANCE
}
/* ----------------------------------------------------------------- */
static fpt *QSAR_FIELD_RB_WTS( molp, rootid )
/* generates rotational-bond wts for each atom */
mol_ptr molp;
int rootid;
{
/* pseudo code for FIELD_RB_WTS()

while saw new atoms
      uncover atoms that stopped last shell growth
      grow next "rotational shell"
      while adding to shell
         for each atom in shell
            get neighbors not seen
            for each neighbor
               if bond is rotatable (acyclic, >1 attached atom, not =,am,#)
                  cover all other atoms attached to atom for this shell
               add it to shell
*/ fpt       *ansr = NIL, *vals = NIL, factor, nowfact = 1.0;
   int        found, aggcount, atid, aggid, loop, size;
   set_ptr    aggats = NIL, allats = NIL, nuls = NIL, endatms = NIL, end_cands
   atom_ptr   root, SYB_ATOM_FIND_REC(), at, atrec ;
   bond_ptr   b, SYB_BOND_FIND_REC();
   List_Ptr   toats, UTL_LIST_RETRIEVE_P();
   acon_ptr   cptr;
   char       tempString[200];
   void       ashow(), qsar_field_attached_atoms();

if (!( vals =  (fpt *) UTL_MEM_ALLOC( sizeof(fpt)*molp->natoms))) return( NI
   if (!UIMS2_VAR_GET_TOKEN( "TAILOR!COMFA!AGGREG_DESCALE",
      &factor ) ) return( NIL );
   if (!(allats = UTL_SET_CREATE( molp->max_atoms + 1 ) )) goto cleanup;
   if (!(aggats = UTL_SET_CREATE( molp->max_atoms + 1 ) )) goto cleanup;
   if (!(nuls = UTL_SET_CREATE( molp->max_atoms + 1 ) )) goto cleanup;
   if (!(endatms = UTL_SET_CREATE( molp->max_atoms + 1 ) )) goto cleanup;
   if (!(end_cands = UTL_SET_CREATE( molp->max_atoms + 1 ) )) goto cleanup;
   if (!( root = SYB_ATOM_FIND_REC( molp, rootid ) )) goto cleanup;
   UTL_SET_INSERT( aggats, root->recno );
   UTL_SET_INSERT( allats, root-> recno );
   aggcount = loop = 1;
```

```
    while (TRUE) {
        while (TRUE) {
            aggid = -1;
            while ((aggid = UTL_SET_NEXT( allats, aggid )) >= 0 ) {
                UTL_SET_CLEAR( nuls );
                qsar_field_attached_atoms( nuls, molp, aggid );
                UTL_SET_DIFF_INPLACE( nuls, allats, nuls );
                UTL_SET_DIFF_INPLACE( nuls, endatms, nuls );
/* identifying any atoms that terminate this aggregate */
                atid = -1;
                while ((atid = UTL_SET_NEXT( nuls, atid )) >= 0 ) {
                    if (!( at = SYB_ATOM_FIND_REC( molp, atid ) )) goto cleanup;
/* skipping monovalent atoms */
                    if (at->nbond > 1) {
/* find bond record that attaches to aggid */
                        toats = at->conn_atom;
                        found = FALSE;
                        while (toats && !found ) {
                            toats = UTL_LIST_RETRIEVE_P( toats, &cptr, &size );
                            found = (cptr-> target == aggid );
                        }
                        if (!found) goto cleanup;
                        b = SYB_BOND_FIND_REC (molp, cptr->bond_rec);
                        if ( !(b->status & BOND_V_IRING) && !(b->status & BOND_V_ERI
                                && (b->type == SYB_BTAB_MNEM_TO_TYPE("1") ) ) {
/* have an end-of-aggregate atom, mark as end atoms all other attached atoms */
                            UTL_SET_CLEAR( end_cands );
                            qsar_field_attached_atoms( end_cands, molp, at->recno );
                            UTL_SET_DELETE( end_cands, aggid );
                            UTL_SET_OR_INPLACE( endatms, end_cands, endatms );
                        }
                    }
                }
                UTL_SET_OR_INPLACE( aggats, nuls, aggats );
            }
            if (UTL_SET_CARDINALITY( aggats ) <= aggcount ) break;
            aggcount = UTL_SET_CARDINALITY( aggats );
            UTL_SET_OR_INPLACE( allats, aggats, allats );
        }
/* debugging stuff .. */
/*
        sprintf( tempString, "Aggregate %d (weight = %f ):", loop, nowfact );
        UBS_OUTPUT_MESSAGE( stdout, tempString );
        ashow( aggats, molp );
*/
/* if no atoms added, we are done! */
        if (UTL_SET_EMPTY( aggats )) break;
/* record scaling factor for atoms in this aggregate */
        atid = -1;
        while ((atid = UTL_SET_NEXT( aggats, atid )) >= 0 ) {
            if (!(atrec = SYB_ATOM_FIND_REC( molp, atid ))) goto cleanup;
            vals[ (atrec->id)-1 ] = nowfact;
        }
        UTL_SET_OR_INPLACE( allats, aggats, allats );
        UTL_SET_CLEAR( aggats );
        UTL_SET_CLEAR( endatms );
        aggcount = 0;
        nowfact *= factor;
        loop++;
    }
```

A-24

```
   ansr = vals;

cleanup:
   if (aggats) UTL_SET_DESTROY( aggats );
   if (allats) UTL_SET_DESTROY( allats );
   if (endatms) UTL_SET_DESTROY( endatms );
   if (end_cands) UTL_SET_DESTROY( end_cands );
   if (nuls) UTL_SET_DESTROY( nuls );
   return( ansr );
} static void qsar_field_attached_atoms( aset, m, atid )
/* ors atoms attached to atm into aset */
/* WORKS STRUCTLY WITH RECNOS */
set_ptr aset;
mol_ptr m;
int atid;
{
   atom_ptr at, SYB_ATOM_FIND_ID();
   List_Ptr tohs, UTL_LIST_RETRIEVE_P();
   atom_ptr toh, SYB_ATOM_FIND_REC();
   acon_ptr conn1;
   int nbytes1;

at = SYB_ATOM_FIND_REC( m, atid );
   tohs = at->conn_atom;
   while (tohs) {
        tohs = UTL_LIST_RETRIEVE_P( tohs, &conn1, &nbytes1);
        toh = SYB_ATOM_FIND_REC( m, conn1->target );
        UTL_SET_INSERT( aset, toh->recno );
   }
   return;
} static void ashow( aset, m )
/* for interactive debugging, shows a set's membership in terms of atom ID */
set_ptr aset;
mol_ptr m;
{
    char buff[1000], *b;
    atom_ptr at, SYB_ATOM_FIND_REC();
    int elem;

*buff = '/0';
    b = buff;
    elem = -1;
    while ( (elem = UTL_SET_NEXT( aset, elem)) >= 0 ) {
         at = SYB_ATOM_FIND_REC( m, elem );
         sprintf( b, " %d", at->id );
         b = buff + strlen( buff );
    }
    sprintf( b, "\n" );
    UBS_OUTPUT_MESSAGE( stdout, buff );
}
```

```

#   Section II-A.  SPL invoked shell for computing the diagonal defining the
#       "best" triangle, e.g., the one with the highest density of points below.

@expression_generator LRT_FAST
# Usage:
#   lrt_fast rows descriptor_cols bio_col [pls flags like scaling in quotes]
#       rows (*) - rows to take
#       descriptor_cols - which columns are the neighborhood metrics
#       bio_col  - which column has the bio (probably log bio) data
#       [...]  - if need to SCAL NONE or anything like that, do it here

# returns a line of the form
#     3.09691 / 0.000546509 = 5666.71 - 496 : 496 :: 15.6981 : 15.6989
#       ^ max bio difference
#                ^ optimal distance division for max bio
#                            ^ slope
#                                        ^number in the lrt
#                                            ^total number
#                                                    ^area in the lrt
#                                                            ^total area
# Significance is related to whether ratio of numbers is
#   much above ratio of areas.

 globalvar SAMPLS_IN_PROGRESS DONE_CHECKED_OUT
 localvar hold distname rows cols bio setvar rows %promptif("$1" ROW_EXP "*" "Rows to use in lrt")
 setvar cols %promptif("$2" COL_EXP "COMFA*" "Columns of mol descriptors")
 setvar bio  %promptif("$3" COL_EXP "LOGBIO" "Column of bio data")

setvar hold SAMPLS_IN_PROGRESS
 setvar SAMPLS_IN_PROGRESS $bio setvar distname TAILOR!HIER!DIST_FNAME
 setvar TAILOR!HIER!DIST_FNAME lrt_fort.3 here the information is computed and written to a file
whose name is passed in via a TAILOR value
 QSAR ANA DO I >$NULLDEV   $rows $cols HIER $4 | setvar SAMPLS_IN_PROGRESS $hold
 setvar TAILOR!HIER!DIST_FNAME $distname contents of the file are returned to the caller
 setvar hold %system("cat lrt_fort.3")
 %return( "$hold" )
.

# Section II-B.  SPL script for computing the significance of the distribution
#       found by lrt_fast

@expression_generator dochi
# computes the chi-square statistic for the number of points below
# the diagonal, null hyptheses being the area fraction of the total.

#       To be called as: %dochi( %lrt_fast( ) ), i.e., its inputs
```

```
# are exactly the output of %lrt_fast as described in the lrt_fast header.

   setvar expected %math( $9 * $11 / $13 )
   setvar sq %math( $7 - $expected )
   setvar sq %math( $sq * $sq / $expected )
   %return( $sq )
.

/* Section II-C. Computes the best diagonal in the "virtual graph" of biological
distances vs property differences. */ int QSHELL_HIER_LRT(table,biocol,dmat,nrow,order,lmsg)
char *table;
int biocol, /* column in MSS with biological data */
    nrow,   /* dimension of dmat and order */
    *order; /* array of row IDs to consider */
fpt *dmat;  /* distance matrix for property distances */
char *lmsg; /* file name for results */
{
fpt *p, *q, fabs(), bmax;
int i,j, count, status_array;
char *fpt_colname;
FILE *out, *UTL_FILE_FOPEN();

/* need to get the bio values
     In the n^2 we can repack into n(n-1)/2 then add the n bio values
     and finish with the bio distances */
  /*
     No error handling. Better be data in those rows!
  */ for (count=0, i=0; i<nrow; i++)
  for (j=0; j<i; j++)
    dmat[count++] = dmat[i*nrow + j];

q = p = dmat + ( (nrow-1) * nrow) / 2;
TBL_ACCESS_INDEX_TO_COLNAME(table, biocol-1, &fpt_colname);
TBL_GRAB_INIT_FPTS(table, 1, &fpt_colname );
for ( i=0;i<nrow;i++, p++)
   TBL_GRAB_GET_FPTS_INV(order[i]-1,  &status_array, p);
TBL_GRAB_COMPLETE_FPTS();

bmax = 0.0;
for (count=0, i=0; i<nrow; i++)
  for (j=0; j<i; j++, count++)
    if ( (p[count] = fabs(q[i] - q[j])) > bmax) bmax = p[count];

out = UTL_FILE_FOPEN(lmsg,"w");
QSHELL_HIER_DO_LRT(out,count,dmat,p, bmax);

UTL_FILE_FCLOSE(out);
}
```

```
int QSHELL_HIER_DO_LRT( out, index, xsort, ysort, bmax )
FILE *out;
fpt *xsort, *ysort, bmax;
int index;
{
 int *order, count, j, i, bad;
 int bestN, bestI;
 fpt den,bestDen;

#define CUTOFF ( bmax * ( xsort[order[i]] / xsort[order[j]] ) )

if (!(order = (int    *) UTL_MEM_ALLOC( index *sizeof(int   )))) return 0;
 for (i=0;i<index;i++) order[i]=i;
 bestN = bestI = bad = 0;
 bestDen = 0.0;

fpt_heapsort(index, xsort, order);

for (j=0;count=0, bad=0, j<index ;j++)
 {
    if (xsort[order[j]] <= 0.0) continue;
    for (i=0;i<=j;i++)
    {
       if (ysort[order[i]] <= CUTOFF) count++;
       else                           bad++;
    } /* loop over all d <= this distance     */
    if ( (den = count/ bmax / xsort[order[j]] *2.0) > bestDen)
       {bestDen = den; bestI = j; bestN = index - bad;}
 }   /* loop over all distances               */ den = bmax * xsort[order[index-1]];
 sprintf(msg,"%g / %g = %g   - %d : %d :: %g : %g\n",
         bmax,xsort[order[bestI]], bmax/xsort[order[bestI]],
         bestN,index,den-xsort[order[bestI]]*bmax/2.0, den);
 UBS_OUTPUT_MESSAGE(out,msg);
 UTL_MEM_FREE(order);
 return 1;
}
```

```
/* n is number of elements
   arrin is array of floats to be sorted
   indx is array of ints initially 0...n-1
*/
int fpt_heapsort(n,arrin,indx)
int n;
fpt *arrin;
int *indx;
{
 int l, ir, indxt, i, j;
 fpt q;

l = n/2 ;
 ir = n -1 ;

while (TRUE)     /* the "10" loop */
 {
   if (l>0) { indxt = indx[--l]; q = arrin[indxt]; }
   else
      {
        indxt = indx[ir];  q = arrin[indxt];
        indx[ir--] = indx[0];
        if ( ir == 0 )
           { indx[0] = indxt; return 1; }    /* <=== Only way out !  */
      }
   i = l;
   i = l;
   j = l + 1    +1;
   while (j <= ir)  /* the "20" loop */
   {
     if ( (j<ir) && (arrin[indx[j]] < arrin[indx[j+1]]) ) j++ ;
     if (q < arrin[indx[j]])  { indx[i] = indx[j]; i = j; j = j+j+1; }
     else                     { j = ir+1;                            }
   }
   indx[i] = indxt;
 }
}
```

/* SECTION III-A. Declarations for all non-standard data structures referenced
in the C code functions shown in Sections I and II. */

```
/**********************************************************************/
/*         Molecule and Supporting Structure Definitions              */
/*                                                                    */
/*              John McAlister      09-Aug-1985                       */
/*                                                                    */
/*     This file contains the definitions for the molecular data struc-*/
/*     tures required within SYBYL.  The contents of this file are des-*/
/*     described in detail in the document "SYBYL Molecular Data Struc-*/
/*     tures".                                                        */
/*                                                                    */
/**********************************************************************/

/* Define the molecule descriptor template                            */
    typedef struct  molecule_struct  {
        char         *name;         /* pointer to molecule name             */
        i32          type;          /* molecule type                        */
        List_Ptr     dict;          /* list of dictionaries used with molecule */
        i32          status;        /* molecule status                      */
        char         *comment;      /* pointer to comment for molecule      */
        stamp        cre_time;      /* creation time/user/version stamp     */
        stamp        mod_time;      /* modification time/user/version stamp */
        int          max_props;     /* maximum properties currently allocated */
        int          nprops;        /* number of molecular properties       */
        List_Ptr     props;         /* pointer to list of properties        */
        int          max_feats;     /* maximum features currently allocated */
        int          nfeats;        /* number of molecular features         */
        List_Ptr     feats;         /* pointer to list of molecular features */
        int          max_subst;     /* maximum substructures currently allocated*/
        int          nsubst;        /* number of substructures in molecule  */
        List_Ptr     subst;         /* pointer to list of substructures     */
        List_Ptr     subst_roots;   /* pointer to list of root subst offsets */
        int          max_atoms;     /* maximum atoms currently allocated    */
        int          natoms;        /* number of atoms in molecule          */
        List_Ptr     atoms;         /* pointer to atom array segment list   */
        int          max_bonds;     /* maximum bonds currently allocated    */
        int          nbonds;        /* number of bonds in molecule          */
        List_Ptr     bonds;         /* pointer to bond array segment list   */
        int          charges;       /* type of atomic charges, if present   */
        fpt          vector[3];     /* translation vector for molecule      */
        fpt          matrix[9];     /* rotation matrix for molecule         */
        List_Ptr     assoc_data;    /* pointer to list of associated data   */
                                    /*       descriptors                    */
    } molecule, *mol_ptr;

/*********************** ATOM DEFINITION ******************************/
/*                                                                    */
/* Define the atom entry record template                              */
    typedef struct  atom_struct  {
        char         *name;         /* atom name                            */
        int          type;          /* atom type                            */
        i32          status;        /* atom status                          */
        int          recno;         /* cumulative atom record number        */
        int          id;            /* atom id (logical atom number)        */
        int          link;          /* link to next atom record             */
        int          subst;         /* offset to substructure containing atom */
        List_Ptr     property;      /* pointer to list of properties for atom */
        List_Ptr     feature;       /* pointer to list of features including */
                                    /*    this atom                         */
        int          nbond;         /* number of bonds involving this atom  */
```

```
    List_Ptr    conn_atom;   /* pointer to list of bonded atoms         */
    fpt         xyz[3];      /* coordinates of atom                     */
    fpt         charge;      /* point charge on atom                    */
    }  atom,    *atom_ptr;

/* Define the atom array segment descriptor template                    */
    typedef struct  atom_seg_struct  {
        atom_ptr    seg_head;   /* pointer to head of atom array segment    */
        mol_ptr     molecule;   /* pointer to molecule containing atom seg  */
        int         max_atom;   /* maximum number of atom records in seg    */
        int         natom;      /* number of filled atom records in seg     */
        int         used_atom;  /* offset to first filled record in segment */
        int         free_atom;  /* offset to first free record in segment   */
    }  atom_seg, *aseg_ptr;

/* Define the bond specifier records pointed to by the atom records     */
    typedef struct  atom_conn_struct  {
        int         target;     /* offset to target atom                    */
        int         bond_rec;   /* offset to bond descriptor record         */
    }  atom_conn, *acon_ptr;
```

```c
/********************** BOND DEFINITION ****************************/
/*                                                                  */
/* Define the bond entry record template                            */
    typedef struct  bond_struct  (
        int         type;       /* bond type                              */
        i32         status;     /* bond status                            */
        int         recno;      /* cumulative bond record number          */
        int         id;         /* bond id (logical bond number)          */
        int         link;       /* link to empty bond record              */
        List_Ptr    property;   /* pointer to bond property list          */
        List_Ptr    feature;    /* pointer to list of features including  */
                                /*      this bond                         */
        int         o_subst;    /* offset to origin atom substructure     */
        int         origin;     /* offset to atom at bond origin          */
        int         t_subst;    /* offset to target atom substructure     */
        int         target;     /* offset to atom at bond destination     */
    } bond,  *bond_ptr;

/* Define the bond array segment descriptor template                */
    typedef struct  bond_seg_struct  (
        bond_ptr    seg_head;   /* pointer to head of bond array segment  */
        mol_ptr     molecule;   /* pointer to molecule containing bond seg*/
        int         max_bond;   /* maximum number of bonds in segment     */
        int         nbond;      /* number of filled bond records in seg   */
        int         used_bond;  /* offset to first filled record in segment */
        int         free_bond;  /* offset to first free record in segment */
    } bond_seg, *bseg_ptr;
```

```
/*********************************************************************/
/*  =====    comfa.h  ======                                         */
/*  Regions are the set of points at which energy evaluations are made */
/*           in the CoMFA method of QSAR. A region is defined as the union */
/*           of a set of 3D boxes (which may be a single point in the */
/*           limit) and their associated attributes. Attributes needed for */
/*           CoMFA purposes are outlined below.                      */
/*                                                                   */
/*********************************************************************/ ifndef         QSAR_COMFA_DEFINITIONS
define         QSAR_COMFA_DEFINITIONS 1
#include        "ta_types.h"
#define         DUMMY 26        /* dummy atom id */
define         LP    20        /* lone pair atom id */ typedef enum {
  FDENGY_UNKNOWN,
  FDENGY_ELECT,
  FDENGY_STERIC,
  FDENGY_HOMO,
  FDENGY_LUMO,
  DOCK_ELECT,
  DOCK_STA_NOHB,
  DOCK_STA_HBD,
  DOCK_STA_HBA,
  DOCK_STB_NOHB,
  DOCK_STB_HBD,
  DOCK_STB_HBA } FldEngyTyp;

typedef enum {
  FDHD_ORIGINAL,
  FDHD_FFIT,
  FDHD_XTERN,
  FDHD_FUNC,
  FDHD_USER,
  FDHD_USR_AVG,
  FDHD_DOCK,
  FDHD_AVG,
  FDHD_SIG,
  FDHD_MAX,
  FDHD_MIN,
  FDHD_COEFF,
  FDHD_AVG_X,
  FDHD_SIG_X,
  FDHD_FLD_X,
  FDHD_RANGE,
  FDHD_PLS_XWT,
  FDHD_PLS_XLOAD,
  FDHD_FAC_LOAD,
  FDHD_FAC_COMM,
  FDHD_FAC_ROTLOAD,
  FDHD_SIMCA_LOAD,
  FDHD_SIMCA_MODEL,
  FDHD_SIMCA_DISCRIM,
  FDHD_HBD   } FldHowTyp;
```

```
typedef struct {
  fpt    lo[3],       /* corner with lowest values for each axis          */
         hi[3],       /*    "    "   hi-est    "    "    "    "           */
         stepsize[3]; /* increment between points                         */
  int    nstep[3],    /* derived as 1 + (hi-lo + epsilon) / stepsize      */
         n;           /*   n = product of nstep[i]                        */
  int    atom_type;   /* SYBYL atom type, for steric energy computation   */
  fpt    pt_charge;   /* elemental charge at point, for electrostatics    */
  fpt    *weight;     /* weight[n] is applied in all computations,e.g=1   */
  int    avg_type;    /* box of 'scale', sphere, sphere x vdw, ...?       */
  fpt    avg_scale;   /* scale whose meaning derived from avg_type        */
  int    arb,         /*    arbitrary int for later use                   */
         *parb;       /*        "    pointer   "    "                     */
       } Box, *BoxPtr ;

typedef struct {
  char *filename ;    /* name of the region's file (if any)               */
  int  n_boxes;       /* number of boxes which make up the region         */
  int  n_points ;     /* number of points in this region altogether       */
  BoxPtr box_array;   /* box_array[n_regions], each one a Box             */
  int  n_refs    ;    /* number of CURRENT references to this memory      */
  long when_made;     /* creation stamp                                   */
              } Region, *RegionPtr ;

typedef struct {
  char *reg_name;     /* name of the region's file (if any)               */
  char *fld_name;     /* name of this field's file (if any)               */
  RegionPtr reference; /* the region referenced by this field             */
  FldEngyTyp fld;     /* what type of field is referenced here            */
  int  num_avgd;      /* number of fields averaged into this one          */
  int  curr_iter;     /* number of iterations in current field fit run    */
  char *mol_id;       /* unspecified molecule id,
                          e.g. dbname/molname/alignname                   */ int  n_points ;     /* number of points in associated region            */
  int  zap_el;        /* whether electrostatics are MISSING when>max_st   */
  fpt  max_value;     /* largest permitted absolute value of energy       */
  fpt  *field_value;  /* values at each point of the field                */
  int  n_refs    ;    /* number of CURRENT references to this memory      */
  long when_made;     /* creation stamp                                   */
  int  vol_avg_type;     /*  added these 4 items 1/30/89 DEP */
  fpt  scale_vol_avg;
  int  dielectric;
  int  repulsive;
  FldHowTyp how_made;    /* perry's way = 1 or old way = 0 */
     } Field, *FieldPtr ;
```

A-35

```
/* molecule dependent information solicited by QSAR table operations,
   passed into COMFA column field evaluations                          */ typedef struct {
 boolean    already_field; /* whether a field name exists (otherwise alignment) */
 char       *some_name;    /* name of alignment;       NIl align==use as is (!) */
 char       *steric_name;  /* name of steric        field (if applicable)       */
 char       *elect_name;   /* name of electrostatic field (if applicable)       */
 FieldPtr sfld_p;          /* points to steric field in memory (when there)    */
 FieldPtr efld_p;          /* points to elect. field in memory (when there)    */
} ComfaMol, *ComfaMolPtr;

/* molecule-independent information for CoMFA evaluations */ typedef struct {
 int  vol_avg    ;     /* case for volume averaging: 0,1,2=none,box,sphere(0)*/
 fpt  vol_scale  ;     /* scale for volume averaging (1.0)                   */
 int  fld_types  ;     /* case for what fields: 0,1,2=both,steric,elect.(0)  */ fpt  steric_max;      /* maximum steric energy (30)                         */
 int  repulsive ;      /* steric repulsive exponent - 12,10,or 8 (12)        */
 fpt  elect_max ;      /* maximum electrostatic energy (30)                  */
 int  dielectric;      /* case for dielectric (AS FORCE FIELD TAILOR)        */
 int  elect_out ;      /* case to drop elect inside steric max: 0,1=T,F (1)  */ char *region_name;    /* name of region used in the CoMFA computations      */

FieldPtr sweight_fld; /* points to MEMORY field for weighting steric PLS    */
 FieldPtr eweight_fld; /* points to MEMORY field for weighting elect. PLS    */
 FldHowTyp how_done;      /* perry's way = 1 or old way = 0 */
 int  du_lp_steric;    /* include dummies and lone pairs in steric field
                          calculations */
 int  du_lp_elect;     /* include dummies and lone pairs in electrostatic
                          field calculations */
 int  spare1;          /* As of 6.1comfa , this is TAILOR!COMFA!TRANSFORM*/
 int  spare2;          /* INDICATOR SCALE among other things                 */
} ComfaTop, *ComfaTopPtr;

#endif
```

Section III-B. Functional descriptions of external procedures. (Routines that simply return dynamic memory to the heap are not described.)

BOND_V_ERING - TRUE if bond is in an external ring.

BOND_V_IRING - TRUE if bond is in an internal (simple) ring.

QSAR_FIELD_EVAL_GETOFF - provides coordinates for field computation when "volume averaging" is being done.

QSAR_FIELD_VDWTAB - returns steric parameters for the computation of the field contribution from the probe atom and each of the molecule atoms.

SYB_AREA_GET_MOLECULE - returns the internal representation of the molecule in some area or "container", if such exists.

SYB_ATAB_ATOMIC_NUMBER - returns the atomic number of the specified atom type.

SYB_ATAB_ATOMIC_WEIGHT - returns the atomic weight of the specified atom type.

SYB_ATAB_HBOND_ACCEPT - returns TRUE if the specified atomic type is a hydrogen-bond accepting atom.

SYB_ATAB_VDW_RADII - returns the atomic radius of the specified atomic type.

SYB_ATOM_FIND_ID - returns the internal representation of an atom referenced by its atom ID number (Atom IDs are guaranteed to be continuous but the ID of any single atom may change as atoms are added or deleted.)

SYB_ATOM_FIND_REC - returns the internal representation of an atom referenced by its record ID number. (Atom record IDs are invariant but there may be "holes" in their sequence such that the largest record ID may be greater than the number of atoms.)

SYB_ATOM_FIND_SET - returns the bitset of atoms corresponding to a list of atoms.

SYB_BOND_FIND_REC - returns the internal representation of a bond referenced by its (invariant) record ID number.

SYB_BTAB_MNEM_TO_TYPE - converts an ASCII representation of a bond type to its internal representation.

SYB_EXPR_ANALYZE - parses a user-entered ASCII description of atoms (e.g., M2(<H>) for all hydrogen atoms within molecule M2) into internally valid representations of molecule and atoms.

SYB_HBOND_DONORS - returns the set of IDs for atoms which are hydrogen-bonding hydrogens.

TAILOR_STORE_IT_HERE - returns the current value of a user- (and SPL-) accessible variable.

TBL_ACCESS_INDEX_TO_COLNAME - converts a user-provided MSS column ID to a column name (name is guaranteed to be a unique identifier).

TBL_GRAB_COMPLETE_FPTS - done returning multiple (scalar) values in an MSS column to an array.

TBL_GRAB_GET_FPTS_INV - in a multiple value retrieval, returns the value corresponding to a user-provided row ID.

TBL_GRAB_INIT_FPTS - set up for returning multiple (scalar) values in an MSS column to an array.

UBS_OUTPUT_MESSAGE - equivalent to *fprintf()*

UIMS2_VAR_GET_TOKEN - returns the current value of a global SPL variable.

UIMS2_WRITE_ERROR - writes text to the error output stream.

UTL_FILE_FCLOSE, UTL_FILE_FOPEN - equivalent to *fclose()* and *fopen()*.

UTL_LIST_RETRIEVE - returns the next element on a linked list.

UTL_MEM_ALLOC - equivalent to *malloc()*.

A-38

UTL_SET_AND_INPLACE - makes the first set logically equivalent to the second set, with only those bits that are also 1 in the third set becoming 1 in the first set.

UTL_SET_CARDINALITY - returns the number of bits that are 1 in a particular bitset.

UTL_SET_CLEAR - sets all bits in the set to 0.

UTL_SET_COPY_INPLACE - makes the first set logically identical to the second.

UTL_SET_CREATE - creates and returns an empty set of requested size.

UTL_SET_DELETE - sets the specified bit to 0.

UTL_SET_DIFF_INPLACE - makes the first set logically equivalent to the second set, with all bits that are 1 in the third set becoming 0 in the first set.

UTL_SET_EMPTY - TRUE if all bits in the set are 0.

UTL_SET_INSERT - sets the requested bit to 1.

UTL_SET_MEMBER - returns TRUE if the requested set bit equals 1.

UTL_SET_NEXT - returns the identity of the next non-zero bit in a set.
UTL_SET_OR_INPLACE - makes the first set logically equivalent to the second set, with all bits that are 1 in the third set becoming 1 in the first set.

UTL_STR_CMP_NOCASE - non-case sensitive version of strcmp().

APPENDIX "B"

```c
/* CODE.  This code implements a PHORE_LOC column type and calculates a single
cell value (the Hydrogen Bonding Fingerprint for a molecule) within the SYBYL
Molecular Spreadsheet.  It is to be understood that other supporting code handles
user input, user output, and disk file I/O. */

/* data structure for PHORE_LOC column type */
typedef
    struct PHORE {
        char   *disco_fn;     /* user name for DISCO feature file - default
appears below */
        int    disco_in;      /* internal flag if DISCO feature file loaded */
        char   *region_fn;    /* user name for defining region file */
        RegionPtr rgn;        /* internal reference to region when loaded */
        int    nfuzz;         /* number of extra lattice points (each direction)
for each PHORE feature */
        int    nbits;         /* set length (must agree with rgn contents or EVAL
fails) */
    } PHORE, *PPHORE;

/*+E:QSAR_PROC_EVAL_PHORE_LOC */
/***************************************************************************/
/*     int QSAR_PROC_EVAL_PHORE_LOC(tablename, row, colname)           */
/*                                                                     */
/*     Dick Cramer 31-Jul-95      (PHORE_LOC  == lattice bitset )      */
/*                                                                     */
/*     This module generates bitsets whose cardinality is equal to     */
/*     lattice points x 2 (# of sitepoint classes. For each            */
/*     instance of a pharmacophoric point in the molecule being        */
/*     processed, the geometrically nearest (1+m)^3 bits in the        */
/*     bitset will be set to 1 (where m is user supplied).             */
/*                                                                     */
/*     NOTE: this routine explicitly requires that sets begin after a  */
/*           first element that is the set size!!!                     */
/*                                                                     */
/*     Inputs                                                          */
/*                                                                     */
/*     Outputs                                                         */
/*                                                                     */
/*     User Required Definition Files                                  */
/*                                                                     */
/***************************************************************************/
/*-E*/
int QSAR_PROC_EVAL_PHORE_LOC(tablename, row, colname)
char   *tablename, *colname;
int    row;
```

```
{
  mol_ptr    mol;
  PPHORE     phr;
  int        err, status, nvalid, mol_area;
  char       *dum;
  set_ptr    print, qsar_proc_calc_phore_set();
  FILE *fp;

/* get the molecule */
    if ( !TBL_UTL_GET_MOLECULE(tablename, row, FALSE, &mol) )
    {
       if ( UTL_ERROR_IS_SET() )                              {err=1; goto error;}
       else  return FALSE;
    }

/* get the user-provided input data */
    if ( !TBL_ATTR_FIND_COLUMN_A(tablename, colname, "PROC_SUPPORT", &dum,
                         (int *)&phr) )          {err=3; goto error;}
/* retrieve DISCO stuff if not yet present */
    if ( ! phr->disco_in) {
       if ( !phr->disco_fn) {err=1; goto error;}
/* set appropriate tailor value, then initialize DISCO */
       sprintf( str, "SETVAR TAILOR!DISCO!FILE %s", phr->disco_fn );
       UIMS2_EXEC_COMMAND( str );
       UIMS2_EXEC_COMMAND( "DISCO INIT" );
       phr->disco_in = TRUE;
    }
/* retrieve region if not yet present */
    if (!phr->rgn ) {
        if ( !phr->region_fn) {err=1; goto error;}
        if (!(phr->rgn = QSAR_REGION_RETRIEVE( phr->region_fn ) ))
{err=4;goto error;}
        if (phr->rgn->n_boxes > 1 ) {
                sprintf( str, "WARNING: Region %s has %d boxes. Only first will be used.\n",
                       phr->region_fn, phr->rgn->n_boxes );
                UBS_OUTPUT_MESSAGE( stdout, str );
        }
        phr->nbits = 2 * phr->rgn->n_points;
    }

/* evaluate this result, first the DISCO call */
    if (!( print = qsar_proc_calc_phore_set( mol, phr, &nvalid )) ) {err=12; goto error;}

/* go store both the bitset in the MSS "Cell_Support" and the number of bits
actually set in the "CELL", so there's something for the user to see */
    if ( !TBL_ACCESS_X_PUT_VALUE(tablename, row, colname, "CELL_SUPPORT",
                         (int *)&print) )        {err=11; goto error;}
```

```
    if ( !TBL_ACCESS_X_PUT_VALUE(tablename, row, colname, "CELL",
                    (int *)&nvalid) )         {err=11; goto
error;}
    return TRUE;

error:
    sprintf (str, "QSAR_PROC_EVAL_PHORE_LOC (%d)", err);
    UTL_ERROR_ADD_TRACE (str);
    return FALSE;
} set_ptr qsar_proc_calc_phore_set( mol, phr, nvalid )
/* creates actual bitset */
    mol_ptr     mol;
    PPHORE      phr;
    int         *nvalid;
{
  set_ptr anset = NIL, pset = NIL, SYB_FEAT_FIND_ID_SET();
  feat_ptr featp, SYB_FEAT_FIND_REC();
  atom_ptr   a, SYB_ATOM_FIND_REC();
  int    err, elem, sitebase, ci, xybase, boff, lt_base[3], lt_off[3], loff =
0, hioff = 0 ;
  fpt   tmp;
  BoxPtr       bxptr;
  line_ptr cdp;

if (!( anset = UTL_SET_CREATE( phr->nbits ) )) {err = 1; goto error;}
    *nvalid = 0;
    if (phr->nfuzz) {
        loff -= phr->nfuzz / 2;
        hioff += (phr->nfuzz + 1 ) / 2;
    }
    bxptr = phr->rgn->box_array;
    xybase = bxptr->nstep[0] * bxptr->nstep[1];

/* generate the DISCO sites for this molecule, which .. */
    UIMS2_EXEC_COMMAND( "ECHO %DISCO_SITES()" );

/* .. become "FEATURES" + "dummy atoms" within SYBYL's molecule data
structure */
    pset = SYB_FEAT_FIND_ID_SET(mol, FEAT_V_LINE, 1, mol->nfeats);

if (pset ) { elem = -1;
  while((elem = UTL_SET_NEXT(pset,elem)) != NO_MORE_ELEM) {
      if (!(featp = SYB_FEAT_FIND_REC (mol,elem)))  goto error;
      if ((featp->name[1] == 'S') && (featp->name[2] == '_')) {
/* have an H-bonding feature, it must represent a line   */
        sitebase = featp->name[0] == 'A' ? 0 : phr->rgn->n_points;
/* the dummy atom at the end of the line is our H-bonding locus */
```

```
        cdp = (line_ptr) featp->dataptr;
        if (!(a = SYB_ATOM_FIND_REC (mol, cdp->positn)) )   {err=2; goto error;}
        for (ci = 0; ci < 3; ci++ ) {
                tmp = (a->xyz[ci] - bxptr->lo[ci]) / bxptr->stepsize[ci];
                lt_base[ci] = (int) (tmp < 0.0 ? tmp - bxptr->stepsize[ci] : tmp );
        }
/* cycle through all points touched by this locus that are also within the region */
        for (lt_off[0] = lt_base[0] + loff; lt_off[0] <= lt_base[0] + hioff; lt_off[0]++)
          if (lt_off[0] >= 0 && lt_off[0] < bxptr->nstep[0])
            for (lt_off[1] = lt_base[1] + loff; lt_off[1] <= lt_base[1] + hioff; lt_off[1]++)
              if (lt_off[1] >= 0 && lt_off[1] < bxptr->nstep[1])
                for (lt_off[2] = lt_base[2] + loff; lt_off[2] <= lt_base[2] + hioff; lt_off[2]++)
                  if (lt_off[2] >= 0 && lt_off[2] < bxptr->nstep[2] ) {
                        boff = xybase * lt_off[2] +
                                (bxptr -> nstep[0]) * lt_off[1] +
                                lt_off[0] + sitebase;
                        UTL_SET_INSERT( anset, boff );
                        (*nvalid)++;
                  }
            }
        }
  }

UTL_SET_DESTROY( pset );
    } /* pset exists */ return( anset );

error:
    sprintf (str, "qsar_proc_calc_phore_set(%d)", err);
    UTL_ERROR_ADD_TRACE (str);
    return FALSE;
}

#  This file determines the recognition of site points in Sybyl/DISCO.
#  See the SYBYL DISCO manual for detailed documentation. The defined types are
#     (1) HB : the QUERY is searched in the SEARCH mode, and all occurences
#              are assigned DISCO features according to the remaining
#              specifications -- the three ATOMS refer to the atom number
#              in QUERY such that the feature is DIST from the first atom
#              at bond ANGLE with the first and second atom at each of the
#              TORSIONS formed by the site point and the three ATOMS in order.
#              A sitepoint of NAME is added at these extension points,
#              -- and -- the first atom is assigned a feature complimentary
```

```
#            to the extension point (such as HBD_CO_ and RHBD_CO_).
#     (2) HBex:differs from HB in that the angles and torsions are replaced
#            by two other arguments: whether lone pairs are part of the
#            extension point placement, and which ATYPE (generally LP
#            and/or H) determine the direction of the sitepoints.

#TYPE  NAME      ATOMS SEARCH DIST ANGLE TORSIONS       QUERY
#====  ====      ===== ====== ==== ===== ========       =====
HB    DS_O2C2_   4 2 1 NoDup  2.9   120  "0.0 180.0"    HevC(Any)=O[f]
HB    DS_O3Car_  1 3 4 All    2.9   119  "0.0 180.0"    O[f]HC(:Hev):Hev
HB    DS_O3Car_  1 2 3 All    2.9   119  "0.0 180.0"    O[f]C(:Hev):Hev
HB    DS_O3Car_  1 3 4 NoDup  2.9   119  "0.0 180.0"    O[f]HC(=O)
HB    DS_O3Car_  1 2 3 NoDup  2.9   119  "0.0 180.0"    O[f]C(=O)
HB    DS_O3Car_  2 1 3 All    2.9   120  "0.0 180.0"    C(:O[f]):O[f]
HB    DS_O3C3_   1 3 6 NoDup  2.9   117  "60 180 300"
O[f]HC(Any)(Any)C(Any)(Any)Any
HB    DS_N3C3_   1 4 5 NoDup  2.9   110  "60 180 300"   N[f]H2ZC{Z:C&!C=O&!C:Hev}
HB    DS_O2S_    3 2 1 All    2.9   120  "0.0 180"      AnyS(=O)(=O)NH
#TYPE  NAME     ATOMS   SEARCH DIST LP  ATYPE   Query
#====  ====     =====   ====== ==== === =====   ==========
HBex  DS_O3C3_  2 1 3   NoDup  2.9  YES "LP H"
O[f]HC(Any)(Any)Z{Z:Hev&!C(Any)(Any)Any}
HBex  DS_O3C3_  3 1 2   NoDup  2.9  YES "LP"    O[f](Z)Z{Z:C&!C=Het}
HBex  DS_N3C3_  2 1 4   Nodup  2.9      ""      "H"
N[f]H2YaZ{Z:Hev&!C}{Ya:C&!C=O&!C:Hev}
HBex  DS_N3C3_  2 1 3   NoDup  2.9  YES "LP H"  N[f]H(Ya)Ya{Ya:C&!C=O&!C:Hev}
HBex  DS_N3C3_  3 1 2   NoDup  2.9  YES "LP"
N[f](Ya)(Ya)Ya{Ya:C&!C=O&!C:Hev}
HBex  DS_N2C2_  2 1 3   NoDup  3.0  YES "H LP"  N[f]H=C
HBex  DS_N2C2_  1 2 3   NoDup  3.0  YES "H LP"  Any~N[f]=C
HBex  DS_N2C2_  1 2 3   NoDup  3.0  YES "LP"    Any~N[r]=C[r]
HBex  DS_N2N2_  2 1 3   NoTriv 3.0  YES "LP H"  N[1]H:C:C:N[f]:C:@1
HBex  DS_N2N2_  2 1 3   NoTriv 3.0  YES "LP H"  N[1]H:C:C:N[f]:C:@1
HBex  DS_N2N2_  3 2 1   NoDup  3.0  YES "LP"    C:N[f]:Hev
hb    DS_O3S_   3 2 1   NoDup  2.9      128     "0.0 180.0"    HevS=O[f]
hb    DS_O3S_   4 2 1   All    2.9      128     "0.0 180.0"    HevS(=O[f])=O[f]
hb    DS_O3S_   4 2 1   All    2.9      128     "0.0 180.0"    HevS(~O[f])(~O[f])~O[f]
hb    DS_O3N_   3 2 4   All    2.9      128     "0.0 180.0"    HevN(O[f])O[f]
hb    DS_O2N_   4 2 1   NoDup  2.9      128     "0.0 180.0"    HevN(Hev)~O[f]
hbex  DS_N2N2_  3 2 1   NoDup  3.0  YES "LP"            N:N[f]:N
hb    DS_O3P_   3 1 2   All    2.9      128     "0.0 180.0"    P(~O)(~O)(~O)(~O)
hb    DS_O3P_   3 1 2   All    2.9      128     "0.0 180.0"    P(~O)(~O)(~O)
#     #CLASSNAMES#  Acceptor_site Donor_Atom DL
HB    AS_HO3C2_  1 3 4 All   2.9   119  "0.0 180.0"  O[f]HC(:Hev):Hev
HB    AS_HO3C3_  1 3 6 NoDup 2.9   117  "60 180 300"
O[f]HC(Any)(Any)C(Any)(Any)Any
HB    AS_N3C3_   1 4 7 NoDup 2.9   110  "60 180 300"
N[f]H2C(Any)(Any)C(Any)(Any)Any
HB    AS_N3C3_   1 5 8 NoDup 2.9   110  "60 180 300"
N[f]H3C(Any)(Any)C(Any)(Any)Any
#TYPE  NAME      ATOMS   SEARCH DIST LP  ATYPE   Query
```

```
#====   ====     =====    ======  ====  === =====  ==========
HBex AS_HN2C2_   2 1 3    NoDup   3.0   ""  "H"    NHC(Any)=O[f]
HBex AS_HN2C2_   3 2 1    NoDup   3.0   YES "LP H" C:N[f]H:Hev
HBex AS_HN2C2_   6 5 4    NoTriv  3.0   YES "LP"   N[1]H:C:C:N[f]:C:@1
HBex AS_HO3C3_   2 1 3    NoDup   2.9   YES "LP H"
O[f]HC(Any)(Any)Z{Z:Hev&!C(Any)(Any)Any}
HBex AS_HN2C2_   3 2 4    Nodup   3.0   YES "LP H" HevN[f]H=C
HBex AS_HN2C2_   1 2 3    Nodup   3.0   YES "LP"   HevN[f]=C
HBex AS_HN2C2_   2 1 4    Nodup   3.0   ""  "H"    N[f]H2C(N)=N
HBex AS_N3C3_    2 1 4    Nodup   2.9   YES "LP H"
N[f]H2C(Any)(Any)Z{Z:Hev&!C(Any)(Any)Any}
HBex AS_N3C3_    2 1 5    Nodup   2.9   YES "LP H"
N[f]H3C(Any)(Any)Z{Z:Hev&!C(Any)(Any)Any}
HBex AS_N3C3_    2 1 3    NoDup   2.9   YES "LP H" N[f]H(Ya)Ya{Ya:C&!C=O&!C:Hev}
HBex AS_N3C3_    2 1 4    NoDup   2.9   YES "LP H" N[f]H2(Ya)Ya{Ya:C&!C=O&!C:Hev}
HBex AS_N3C3_    2 1 3    NoDup   2.9   YES "LP H" N[f]H(Ya)(Ya)Ya{Ya:C&!C=O&!C:Hev}
HBex AS_N3C3_    3 1 2    NoDup   2.9   YES "LP"   N[f](Ya)(Ya)Ya{Ya:C&!C=O&!C:Hev}
HBex AS_HN2C2_   2 1 3    NoDup   3.0   YES "H LP" N[f]H=C
HBex AS_HN2C2_   3 1 2    NoDup   3.0   YES "LP"   N[f]=C~Any
HBex AS_HN2C2_   2 1 4    NoDup   3.0   ""  "H"    N[f]H2Hev(:Hev):Hev
HBex AS_HN2C2_   2 1 3    NoDup   3.0   ""  "H"    N[f]HHev(:Hev):Hev
HBex AS_HN2C2_   1 2 3    NoDup   3.0   ""  "H"    HNC=Any
HBex AS_HNS3_    6 5 2    NoDup   3.0   ""  "H"    AnyS(=O)(=O)N[f]H
HBex AS_HN4_     2 1 3    NoDup   -3.6  ""  "C*"   N[f](Z)(Z)(Z)Z{Z:C&!C=O&!C:Hev}
hbex AS_HN2N2_   3 2 1    NoDup   3.0   YES "LP"   N:N[f]:N
hb   AS_O3P_     3 1 2    All     2.9   128 "0.0 180.0" P(~O)(~O)(~O)(~O)
hb   AS_O3P_     3 1 2    All     2.9   128 "0.0 180.0" P(~O)(~O)(~O)
```

APPENDIX "C"

EXPERIMENTAL DATA SETS

| Data Set | No. Of Cpds | Structure, Activity |
|---|---|---|
| 1 Uehling | 9 | camptothecin, DNA fragmentation |
| 2 Strupczewski | 34 | benzisoxazoles, ip Behavioral |
| 3 Siddiqi | 10 | adenosines, Brain A1 binding |
| 4 Garratt1 | 10 | tryptamines, melanophore binding |
| 5 Garratt2 | 14 | tryptamines, melanophore binding |
| 6 Heyl | 11 | deltorphin, opioid receptor (DAMGO) |
| 7 Cristalli | 32 | adenosines, A2a agonists |
| 8 Stevenson | 5 | piperidines, NK1 antagonism |
| 9 Doherty | 6 | triarylbutenolides, endothelin-A antag. |
| 10 Penning | 13 | SC-41930 analogs, LTB4 antagonism |
| 11 Lewis | 7 | oxazolinediones, NK1 binding |
| 12 Krystek | 30 | sulfonamides, endothelin-A antagonism |
| 13 Yokoyama1 | 13 | oxamic acids, T3 binding |
| 14 Yokoyama2 | 12 | oxamic acids, T3 binding |
| 15 Svensson | 13 | benzindoles, 5-HTA agonism |
| 16 Tsutsumi | 13 | peptidyl heterocycles, endopeptidase inhib |
| 17 Chang | 34 | biphenyl sulfonamides, AT1 binding |
| 18 Rosowsky | 10 | trimetrexate analogs, DHFR inhibition |
| 19 Thompson | 8 | peptidomimetic, HIV-1 protease inhibition |
| 20 Depreux | 26 | naphthylethyl amides, melatonin displ. |

Literature References for Data Sets:

1. Uehling, D.E., Nanthakamur, S.S., Croom, D., Emerson, D.L., Leitner, P.P., Luzzio, M.J., *et al.*, Synthesis, Topoisomerase I Inhibitory Activity, and in Vivo Evaluation of 11-Azacamptothecin Analogs. *J. Med. Chem.* 1995, 38, 1106 (Table 2, with $R_2$=Et; $IC_{50}$ data.

2. Strupczewski, J.T., Bordeau, K.J., Chiang, Y., Glamkowski, E.J., Conway, P.G., *et al.* 3-[[(aryloxy)alkyl]piperidinyl]-1,2-Benzisoxazoles as D2/5-HT2 Antagonists with Potential Atypical Antipsychotic Activity: Antipsychotic Profile of Iloperidone (HP873). *J. Med. Chem.* 1995, 38, 1119. (Tables 2 and 3 with n=3, X=O; $ED_{50}$ for inhibition of apomorphine-induced climbing.)

3. Siddiqi, S.M., Jacobson, K.A., Esker, J.L., Olah, M.E., Ji, Xi.-duo., *et al.*, Search for New Purine- and Ribose-Modified Adenosine Analogs as Selective Agonists and Antagonists at Adenosine Receptors. *J. Med. Chem.* 1995, 38, 1174. (Table 1, $R_2$=H; $K_1$(A1), values estimated from % displacement and stereoisomers averaged as needed.)

4. Garratt, P. J., Jones, R., Tocher, D. A., Sugden, D., Mapping the Melatonin Receptor. 3. Design and Synthesis of Melatonin Agonists and Antagonists Derived from 2-Phenyltryptamines. *J. Med. Chem.* 1995, 38, 1132. (Table 1 and Table 2).

5. Garratt, P. J., Jones, R., Tocher, D. A., Sugden, D., Mapping the Melatonin Receptor. 3. Design and Synthesis of Melatonin Agonists and Antagonists Derived from 2-Phenyltryptamines. *J. Med. Chem.* 1995, 38, 1132. (Table 1 and Table 2).

6. Heyl, D.L., Dandabuthla, M., Kurtz, K.R., Mousigian, C. Opioid Receptor Binding Requirements for the &-Selective Peptide Deltorphin I: $Phe^3$ Replacement with Ring-Substituted and Heterocyclic Amino Acids. *J. Med. Chem.* 1995, 38, 1242. (Table 1; binding $K_1$ to DAMGO.)

7. Cristalli, G., Camaioni, E., Vittori, S., Volpini, R., Borea, P.A., *et al.* 2-Aralkynyl and 2-Heteroalkynyl Derivatives of Adenosine-5'-N-ethyluronamide as Selective A2a Adenosine Receptor Agonists. *J. Med. Chem.* 1995, 38, 1462.

8. Stevenson, G.I., MacLeod, A.M., Huscroft, I., Cascieri, M.A., Sadowski, S., Baker, R. 4,4-Disubstituted Piperidines: A New Class of $NK_1$ Antagonist. *J. Med.*

Chem. 1995, 38, 1264. (Table 1.)

9. Doherty, A.M., Patt, W.C., Edmunds, J.J. Berryman, K.A., Reisdorph, B.R., et al. Discovery of a Novel Series of Orally Active Non-Peptide Endothelin-A ($ET_A$) Receptor-Selective Antagonists. *J. Med. Chem.* 1995, 38, 1259. (Table 3; $IC_{50}$ $ET_A$.)

10. Penning, T.D., Djuric, S.W., Miyashiro, J.M., Yu, S., Snyder, J.P., et al. Second-Generation Leukotriene $B_4$ Receptor Antagonists Related to SC-41930; Heterocyclic Replacement of the Methyl Ketone Pharmacophore. *J. Med. Chem.* 1995, 38, 858. (Table 1, all; $LTB_4$ receptor binding.)

11. Lewis, R.T., MacLeod, A.M., Merchant, K.J. Kelleher, F., Sanderson, I., et al. Tryptophan-Derived NK1 Antagonists: Conformationally Constrained Heterocyclic Bioisosteres of the Ester Linkage. *J. Med. Chem.* 1995, 28, 923.

12. Krystek, S.R., Hunt, J.T., Stein, P.D., Stouch, T.R. 3D-QSAR of Sulfonamide Endothelin Inhibitors. *J. Med. Chem.* 1995, 38, 659.

13. Yokoyama, N., Walker, G.N., Main, A.J. Stanton, J.L. Morrissey, M., et al. Synthesis and SAR of Oxamic Acid and Acetic Acid Derivatives Related to L-Thyronine. *J. Med. Chem.* 1995, 38, 695.

14. Yokoyama, N., Walker, G.N., Main, A.J. Stanton, J.L. Morrissey, M., et al. Synthesis and SAR of Oxamic Acid and Acetic Acid Derivatives Related to L-Thyronine. *J. Med. Chem.* 1995, 38, 695.

15. Haadsma-Svensson, S.R., Svensson, K., Duncan, N., Smith, M.W., Lin, Ch.-H. C-9 and N-Substituted Analogs of cis-(3aR)-(-)-2,3,3a,4,5,9b-Hexahydro-3-propyl-1H-benz[e]indole-9-carboxamide: 5HT1A Receptor Agonists with Various Degrees of Metabolic Stability. *J. Med. Chem.* 1995, 38, 725.

16. Tsutsumi, S., Okonogi, T. Shibahara, S., Ohuchi, S., Hatsushiba, E., *et al.*, Synthesis and Structure Activity Relationships of Peptidyl @-Keto Heterocycles as Novel Inhibitors of Prolyl Endopeptidase. *J. Med. Chem.* 1994, 37, 3492. (Table 2, X=$CH_2CH_2$;$IC_{50}$.)

17. Chang, L.L., Ashton, W.T., Flanagan, K.L., Chen, Ts.-Bau., O'Malley, S.S., *et al.*, Triazolinone Biphenylsulfonamides as Angiotensin II Receptor Antagonists with High Affinity for Both the $AT_1$ and $AT_2$ Subtypes. *J. Med. Chem.*, 1994, 37, 4464. (Table 1, $R^3$ =(2-Cl)$C_6H_5$; $AT_1$ [rabbit aorta] $IC_{50}$.)

18. Rosowsky, A., Mota, C.E., Wright, J.E., Queener, S.F., 2,4-Diamino-5-chloroquinazoline Analogs of Trimetrexate and Piritrexim: Synthesis and Antifolate Activity. *J. Med. Chem.* 1994, 37, 4522. (Table 2; rat liver $IC_{50}$.)

19. Thompson, S.K., Murthy, K.H.M., Zhao, B., Winborne, E., Green, D.W., *et al.* Rational Design, Synthesis, and Crystallographic Analysis of a Hydroxyethylene-Based HIV-1 Protease Inhibitor Containing a Heterocyclic P1'-P2' Amide Bond Isostere. *J. Med. Chem.* 1994, 37, 3100. (Table 2, X-Boc; apparent $K_i$.)

20. Depreux, P., Lesieur, D., Mansour, H.A., Morgan, P., *et al.* Synthesis and Structure-Activity Relationships of Novel Naphthalenic and Bioisosteric Related Amidic Derivatives as Melatonin Receptor Ligands. *J. Med. Chem.* 1994, 37, 3231.

APPENDIX "D"

A list of 736 commercially available thiols broken down into 231 clusters based on topomeric CoMFA field descriptors along with the systematic name applicable to each. The 231 clusters are sorted by proposed name, first by the "root" structure, ie., the fragment attached immediately to the -SH, and then by the substitution pattern on that "root" substructure. The names describe topologically equivalent hydrocarbons, ie., structures in which all monovalent atoms are replaced by hydrogens and the other atoms by carbons.

| Cluster ID | Cluster Size | Struct. Root | Structural Substitution[a] |
|---|---|---|---|
| 1 | 26 | aryl | Simple |
| 144 | 1 | aryl | 2,3,5-Me |
| 177 | 1 | aryl | 2,3,5-Me-4-Pr |
| 163[c] | 1 | aryl | 2,3-(4-(2,3-Pr)5het)5hetO |
| 151 | 1 | aryl | 2,3-(4-Bu)5hetO-5-Me |
| 33 | 5 | aryl | 2,3-Benzo |
| 80 | 2 | aryl | 2,5-Me |
| 192 | 1 | aryl | 2,5-Me-3-iPe |
| 7 | 14 | aryl | 2,6-NoH-3(4/5)-Me |
| 27 | 6 | aryl | 2,6-NoH-3-Ar |
| 107 | 2 | aryl | 2-(2-Bz)PheEt-4,5-Benzo |
| 189 | 1 | aryl | 2-(3,5-Me)Ar-4,5-Benzo |
| 141 | 1 | aryl | 2-(4-Et)PhePr |
| 205 | 1 | aryl | 2-(4-Stilbenyl)Stilbenyl |
| 188 | 1 | aryl | 2-5hetCH2-4,5-Benzo |
| 56 | 3 | aryl | 2-Ar |
| 138 | 1 | aryl | 2-Ar-3,5-Me |
| 190 | 1 | aryl | 2-Ar-4,5-(3,4-Et)Benzo |
| 41 | 6 | aryl | 2-Ar-4,5-Benzo |
| 152 | 1 | aryl | 2-Bz |
| 16 | 9 | aryl | 2-Et |
| 85 | 2 | aryl | 2-NoH-3-Et-5-Me |
| 106 | 2 | aryl | 2-PheEt-4,5-Benzo |
| 77 | 2 | aryl | 2-PhePr |
| 142 | 1 | aryl | 2-R8 |
| 121 | 2 | aryl | 2-Stilbenyl |
| 97 | 2 | aryl | 3,4-(3-Me)Benzo |
| 218 | 1 | aryl | 3,4-(a,b)IndenO |
| 164 | 1 | aryl | 3,4-(a,b,(8-Ar)IndenO)-6-Me |
| 98 | 2 | aryl | 3,4-(a,b,(c-Me)IndenO) |
| 99 | 3 | aryl | 3,4-(a,b-Naphtho) |
| 157 | 1 | aryl | 3,4-Ar |
| 58 | 3 | aryl | 3,4-Benzo-5-Me |
| 100 | 2 | aryl | 3,4-Benzo-6-tBu |
| 37 | 5 | aryl | 3,5-Me |
| 180 | 1 | aryl | 3-(2,3-Benzo-4-Et)5het |
| 199 | 1 | aryl | 3-(2,3-Benzo-5-Me)5het |
| 182 | 1 | aryl | 3-(2-Me-3-5het-5-Et)5het |
| 115 | 2 | aryl | 3-(3-5het)5het |
| 193 | 1 | aryl | 3-(3-Ar)5het-4-Me |
| 67 | 3 | aryl | 3-Ar |
| 129 | 2 | aryl | 3-Ar-4-(2-Me)5hetCH2 |
| 46 | 4 | aryl | 3-Ar-5-Me |
| 155 | 1 | aryl | 3-Bz |
| 82 | 2 | aryl | 3-Bz-5,6-Benzo |
| 10 | 16 | aryl | 3-Me |

D-2

| | | | |
|---|---|---|---|
| 70 | 3 | aryl | 3-Naphth |
| 73 | 3 | aryl | 3-Pr-4-sBu-6-Me |
| 95 | 2 | aryl | 3-iPr |
| 88 | 2 | aryl | 4-Ar |
| 81 | 2 | aryl | 4-Bz |
| 48 | 4 | aryl | 4-Et |
| 2 | 23 | aryl | 4-Me |
| 92 | 2 | aryl | 4-R9+ |
| 90 | 4 | aryl | 4-iBu |
| 19 | 8 | aryl | 6-NoH |
| 148[c] | 1 | aryl | (adenosine) |
| 228 | 1 | aryl | (fluorescein) |
| 12 | 10 | 5het | Simple |
| 50 | 4 | 5het | 2,3-(a,b-Naphtho) |
| 139 | 1 | 5het | 2,3-5hetO-4-Me |
| 89 | 2 | 5het | 2,3-Ar |
| 173 | 1 | 5het | 2-(2,5-Et)Ar-3-Et |
| 69 | 3 | 5het | 2-(2-Me)Ar-3-(2-Me)PheEt |
| 198 | 1 | 5het | 2-(2-Me)Ar-3-R10 |
| 174 | 1 | 5het | 2-(2-sBu)-3-Et |
| 171 | 1 | 5het | 2-(3,5-Me)Ar-3-5het |
| 170 | 1 | 5het | 2-(3,5-Me)Bz-3,4-Benzo |
| 123 | 2 | 5het | 2-(3-Et)Ar-3-Bz |
| 22 | 7 | 5het | 2-(4-Et)Ar |
| 202 | 1 | 5het | 2-(4-Et)Ar-4-(4-Me)Ar |
| 122 | 2 | 5het | 2-(4-iPr)Ar-3-Bz |
| 197 | 1 | 5het | 2-5hetCH2-3-(4-tBu)Ar |
| 6 | 14 | 5het | 2-Ar |
| 225 | 1 | 5het | 2-Ar-3-(2-Ar)5hetBu |
| 224 | 1 | 5het | 2-Ar-3-(2-Ar)5hetCH2 |
| 63 | 3 | 5het | 2-Ar-3-(2-Bz)Ar |
| 178 | 2 | 5het | 2-Ar-3-(2-Me)5het |
| 72 | 3 | 5het | 2-Ar-3-(3,4-Et)Bz |
| 40 | 5 | 5het | 2-Ar-3-(3-Ar)5HetEt |
| 183 | 1 | 5het | 2-Ar-3-(3-Ar)PhePr |
| 64 | 3 | 5het | 2-Ar-3-(3-Ar-5-Me)5het |
| 105 | 2 | 5het | 2-Ar-3-(3-Me)Ar |
| 160 | 1 | 5het | 2-Ar-3-(4-Ar)Cyhx |
| 146 | 1 | 5het | 2-Ar-3-(4-Ar)CyhxCH2 |
| 203 | 1 | 5het | 2-Ar-3-(4-PheEt)Ar |
| 126 | 2 | 5het | 2-Ar-3-(tBu)Ar |
| 17 | 9 | 5het | 2-Ar-3-Ar |
| 211[c] | 1 | 5het | 2-Ar-3-Benzylidene |
| 124 | 2 | 5het | 2-Ar-3-IndenCH2 |
| 28[b] | 6 | 5het | 2-Ar-3-Me |
| 30 | 6 | 5het | 2-Ar-3-PhePr |
| 204 | 1 | 5het | 2-Ar-5-(4-(2,4-Me)Bz)Ar |
| 79 | 2 | 5het | 2-Bz |
| 78 | 2 | 5het | 2-Bz-3,4-Benzo |
| 117 | 2 | 5het | 2-Cyhx |
| 186 | 1 | 5het | 2-Cyhx-3,4-iPe |
| 68 | 3 | 5het | 2-Et |
| 112 | 2 | 5het | 2-Et-3-(2-Me)PheEt |

| | | | |
|---|---|---|---|
| 128 | 2 | 5het | 2-Me-3,4-(3-Me)Benzo |
| 93 | 2 | 5het | 2-Me-3,4-Benzo |
| 61 | 3 | 5het | 2-Me-3-(2,3,4-Me)5het |
| 181 | 1 | 5het | 2-Me-3-(2,3-Benzo-4-Et)5het |
| 49 | 4 | 5het | 2-Me-3-(3-Ar)5het |
| 86 | 2 | 5het | 2-Me-3-(3-Ar)5hetPr |
| 91 | 2 | 5het | 2-Me-3-(3-Ar-5-Me)5het |
| 4 | 17 | 5het | 2-Me-3-(3-Bz)Ar |
| 172 | 1 | 5het | 2-Me-3-(4-tBu)PheEt |
| 38 | 5 | 5het | 2-Me-3-5Het |
| 13 | 10 | 5het | 2-Me-3-Me |
| 222 | 1 | 5het | 2-Me-3-Pe |
| 66 | 3 | 5het | 2-Me-3-PheEt |
| 29 | 6 | 5het | 2-Me-3-PhePr |
| 71 | 3 | 5het | 2-Me-3-R8+ |
| 108 | 2 | 5het | 2-Me-5-Bu |
| 127 | 2 | 5het | 2-Pe-3-Ar |
| 54 | 3 | 5het | 2-Pr |
| 221 | 1 | 5het | 2-R12 |
| 187 | 1 | 5het | 2-iBu-3,4-iPe |
| 143 | 1 | 5het | 2-iPe-3,4-Benzo |
| 96 | 2 | 5het | 3,4-(2,4-Me)Benzo |
| 162 | 1 | 5het | 3,4-(3-Ar)Benzo |
| 169 | 1 | 5het | 3,4-(3-Hx)Benzo |
| 94 | 2 | 5het | 3,4-(3-Pr)Benzo |
| 210 | 1 | 5het | 3,4-(a,b-Napththo) |
| 36 | 15 | 5het | 3,4-Benzo |
| 176 | 1 | 5het | 3-(2,4-Me)Bz |
| 196 | 1 | 5het | 3-(3,5-Me)Ar |
| 159 | 1 | 5het | 3-(3-Ar)5het |
| 42 | 4 | 5het | 3-(3-Bz)Ar |
| 200 | 1 | 5het | 3-(3-Me)PheEt |
| 113 | 2 | 5het | 3-(4-Me)Ar |
| 125 | 2 | 5het | 3-(4-tBu)Ar |
| 191 | 1 | 5het | 3-(A1-4-Et)PheEt |
| 145 | 1 | 5het | 3-(B-Ar)PhePr |
| 114 | 2 | 5het | 3-5hetCH2 |
| 18 | 8 | 5het | 3-Ar |
| 59 | 3 | 5het | 3-Ar(2-thia) |
| 65 | 3 | 5het | 3-Bu |
| 24 | 7 | 5het | 3-Me-5-H |
| 44 | 6 | 5het | 3-Me-5-NoH |
| 52 | 5 | 5het | 3-Pe |
| 111 | 2 | 5het | 3-PheEt |
| 153 | 1 | 5het | 3-PhePr |
| 32[b] | 6 | 5het | 3-Pr |
| 223 | 1 | 5het | 3-R13 |
| 185 | 1 | 5het | (chrysenO) |
| 34 | 5 | alkyl | Simple |
| 104 | 2 | alkyl | (3)(B1)(B1) |
| 62 | 3 | alkyl | (3-Me)PhePr |
| 3 | 18 | alkyl | (3:4) |
| 14 | 9 | alkyl | (3:4)(A1) |

D-4

| | | | |
|---|---|---|---|
| 60 | 3 | alkyl | (3:4)(B1) |
| 226 | 1 | alkyl | (4)(A1)(A-tBu)(C1)(C1) |
| 45 | 4 | alkyl | (4)(D1)(D1) |
| 35 | 7 | alkyl | (4-Me)PhePr |
| 168 | 1 | alkyl | (4-iPe)PhePr |
| 47 | 4 | alkyl | (5)(A1) |
| 179 | 1 | alkyl | (5)(B1)(E-(2-Ar-5-Me)5het) |
| 103 | 2 | alkyl | (5)(B3) |
| 76 | 2 | alkyl | (5)(C1)(C1) |
| 83 | 2 | alkyl | (5)(C2) |
| 216 | 1 | alkyl | (5)(C2)(D2)(D2) |
| 43 | 8 | alkyl | (5:6)(D1/B1/F1) |
| 5 | 15 | alkyl | (5:7) |
| 158 | 1 | alkyl | (6)(B8)(C1)(E1)(E1) |
| 140 | 1 | alkyl | (6)(F-Ar) |
| 166 | 1 | alkyl | (7)(A8)(F1) |
| 53 | 3 | alkyl | (7)(D3)(D3) |
| 207 | 1 | alkyl | (8)(C3) |
| 8 | 13 | alkyl | (8:11) |
| 206 | 1 | alkyl | (9)(B4)(G3) |
| 75 | 3 | alkyl | (10)(B1)(E5)(E1) |
| 136 | 1 | alkyl | (10)(C1)(E5)(E2) |
| 20 | 8 | alkyl | (10+)(B1) |
| 39 | 7 | alkyl | (11+)(B1) |
| 154c | 1 | alkyl | (12)(A-PheEt) |
| 230 | 1 | alkyl | (12)(F6)(F1) |
| 131 | 2 | alkyl | (12)(F6)(F6) |
| 15 | 9 | alkyl | (12+) |
| 137 | 1 | alkyl | (13)(E4) |
| 231 | 1 | alkyl | (A-Ar)(A-Ar)Bz |
| 229 | 1 | alkyl | (A-Bz)(A-Bz)PheEt |
| 184 | 1 | alkyl | (A1)PheEt |
| 227c | 1 | alkyl | (cholesterol) |
| 214c | 1 | alkyl | (cryptate) |
| 23 | 7 | alkyl | PheBu |
| 74 | 3 | alkyl | PheEt |
| 25b | 6 | alkyl | PhePr |
| 11 | 10 | benzyl | Simple |
| 102 | 2 | benzyl | 2,4,5-Me |
| 57 | 3 | benzyl | 2,4,6-Me |
| 217 | 2 | benzyl | 2-(3-(2-Et)Ar)Ar |
| 213 | 1 | benzyl | 2-Et-3-(2,3-Et-5-Me)Ar-5-Me |
| 212 | 1 | benzyl | 2-R8-3-Naphthyl-4,5-Benzo |
| 9 | 13 | benzyl | 2/3-Me |
| 84 | 2 | benzyl | 3,4-Benzo |
| 132 | 2 | benzyl | 3,5-Me |
| 130 | 2 | benzyl | 3-(4-Stilbenyl)Stilbenyl |
| 134 | 2 | benzyl | 4-(3-Ar)Ar |
| 21 | 7 | benzyl | 4-Et |
| 26b | 6 | benzyl | 4-Me |
| 156 | 1 | benzyl | 4-PhePr |
| 201 | 1 | benzyl | 4-tBu |
| 135 | 2 | alkenyl | Ar..(2-Et)Ar |

| | | | |
|---|---|---|---|
| 220 | 1 | alkenyl | Ar..(4-Bz)Ar |
| 116 | 2 | alkenyl | Ar..Ar |
| 133 | 2 | alkenyl | Ar..Bz |
| 110 | 2 | alkenyl | Et.CN.CONH2 |
| 87 | 2 | alkenyl | NH2.CN.N=NPh |
| 119 | 2 | alkenyl | P(NMe2)3..Ar |
| 120 | 2 | alkenyl | P(Pr)3..Ar |
| 118 | 2 | alkenyl | P(iPe)3..Ar |
| 51 | 4 | alkenyl | PCyhx3..Ar |
| 195[c] | 1 | alkenyl | PEt3..(2-Bz)Ar |
| 31[b] | 6 | alkenyl | PEt3..Ar |
| 194 | 1 | alkenyl | PEt3..Bz |
| 109 | 2 | alkenyl | PheEt.CN.CONH2 |
| 101 | 2 | cyclohexyl | Simple |
| 149 | 1 | cyclohexyl | 1-Me-2,4-CMe2 |
| 55 | 3 | cyclohexyl | 2,3,4,5-iBu |
| 147 | 1 | cyclohexyl | 2,3,4-iBu-5-iPe |
| 209 | 1 | cyclohexyl | 2-(3,4-PheEt)5het-6-Me |
| 208 | 1 | cyclohexyl | 2-Me-3,5-CMe2 |
| 167 | 1 | cyclohexyl | 2-Me-4-sPe |
| 165 | 1 | cyclohexyl | 2-iPr-3,5-Me |
| 150 | 1 | cyclohexyl | 3-sPe-6-Me |
| 161 | 1 | cyclohexyl | 4-Et-4-iBu |
| 219 | 1 | cyclohexyl | (complex) |
| 175 | 1 | cyclopentyl | 2-Ar-4-spiro |
| 215 | 1 | cyclopentyl | 3-PhePr |

[a]To generate these names, <u>all heteroatoms are first replaced by carbon</u> (to produce the simplest common topology) and a particular structure is chosen from among these topologies as the "most typical" of that cluster, if possible to contain the largest substructure that distinguishes that cluster from all others.

Within the name of a substitution, numbers indicate positions when substitution is on a ring, but chain length when substitution is on a chain (numbers separated by a colon indicate a range of chain lengths). Also, within a chain, letters indicate a position of substitution. (For example, (C2) describes a two atom branching from the third position of a chain, while 3-PhePr describes a phenyl propyl skeleton attached to the 3-position of a ring.)

A dot notation (.) separates the three possible substituents on an alkenyl root, the substituent order being same carbon as the -SH substituent, then the position *trans* to the -SH, and finally *cis* to -SH.

The above notwithstanding, <u>any</u> name enclosed completely in parentheses takes its usual structural meaning.

Here are structural descriptions for each name abbreviation in the above table, mostly in SLN (SYBYL Line Notation), listed alphabetically. (SLN extends SMILES with the following concepts, among others. Hydrogens are explicit. Ring openings and closures begin with a number enclosed by [] and end with the matching number preceded by @. Other SLN symbols used in these SLN definitions are: ~ = any bond; - = single bond (used here to provide a reference for [R]) : = aromatic bond; ! = the SLN following (here in parentheses) is not allowed; [F] = no additional atoms may be attached to the preceding atom; [!R] = preceding bond may not be in a ring; [R] = preceding bond must be in a ring.)

5het = 5Het = C[1]:C:C:C:C:@1. alkenyl = C=C. alkyl = C~[!R]C. aryl = Ar = Phe = Ph = C[1]:C:C:C:C:C@1. benzyl = Bz = HSC-[!R]C~[R]C. Bu = C-[!R]C-[!R]C-[!R]C-[!R]C. cyclohexyl = Cyhx = C[1](-!=)C~C~C~C~C~@1. cyclopentyl = C[1]~(-!=)C~C~C~@1. Et = C-[!R]C. inden = C[1]:C(~C~X~[2]):C(~@2):C:C@1. iBu = C-[!R]C-[!R]C(-[!R]C)-[!R]C. iPe = C-[!R]C-[!R]C-[!R]C(-[!R]C)-[!R]C. Me = C. naphth = C[1]:C(~C~X~[2]):C(~@2):C:C:C@1. NoH = !(CH). O denotes ring fusion, e.g., benzo fuses a 6-membered aromatic ring. Pe = C-[!R]C-[!R]C-[!R]C-[!R]C-[!R]C. Pr = C-[!R]C-[!R]C-[!R]C. R# = alkyl chain of approximate length #. Simple = !(C~[!R]C). sPe = C(-[!R]C)-[!R]C-[!R]C-[!R]C-[!R]C. Stilbenyl = C=[!R]C-[!R]C[1]:C:C:C:C:C@1. tBu = C(-[!R]C)(-[!R]C)-[!R]C.

What is claimed is:

1. A computer implemented method of merging with a base assembly of molecules one or more additional assemblies of molecules, similar molecules in the assemblies having previously been identified and removed using a molecular structural descriptor validated as possessing a neighborhood property, comprising the steps of:
    a) using a molecular structural descriptor, validated as possessing a neighborhood property, which is appropriate to whole molecules, characterizing all the molecules in the base assembly of molecules and in the assembly of molecules to be merged;
    b) calculating the molecular structural distance between every molecule in the base assembly to every molecule in the assembly to be merged;
    c) while there are still molecules in the assembly to be merged which have not been tested, selecting a molecule from the assembly to be merged;
    d) determining whether the molecular structural distance between the selected molecule and every molecule in the base assembly is within the neighborhood distance of the molecular structural descriptor;
    e) selecting for inclusion in the merged assemblies only those molecules identified in step d as having molecular structural distances greater than the neighborhood distance.
    f) repeating step c through step e until all molecules in the assembly to be merged have been tested; and
    g) repeating step a through step f for each additional assembly to be merged; and
    h) outputting the merged assembly of molecules wherein the merged assembly of molecules has optimal diversity between and among its members.

2. The method of claim 1 in which the molecular structural descriptor, validated as possessing a neighborhood property, appropriate to whole molecules is the Tanimoto similarity coefficient.

3. A computer implemented method of merging with a base assembly of molecules one or more additional assemblies of molecules, similar molecules in one or more of the assemblies having not previously been identified and removed using a molecular structural descriptor, validated as possessing a neighborhood property, comprising the steps of:
    a) selecting subsets of each assembly by:
        (1) selecting a molecule within each assembly;
        (2) using a molecular structural descriptor, validated as possessing a neighborhood property, appropriate to whole molecules, calculating the descriptor distance between the selected molecule and all molecules within the assembly;
        (3) determining the shortest distance between the selected molecule and all molecules previously selected for the subset;
        (4) selecting for inclusion in the subset the molecule whose shortest descriptor distance from the previously selected molecules is the largest and is greater than the neighborhood distance of the descriptor;
        (5) repeating steps (1) through (4) until the largest shortest difference between molecules is less than the neighborhood distance of the descriptor; and
        (6) repeating steps (1) through (5) for each assembly;
    b) using a molecular structural descriptor, validated as possessing a neighborhood property, which is appropriate to whole molecules, characterizing all the molecules in the base assembly of molecules and in the assembly of molecules to be merged;
    c) calculating the molecular structural distance between every molecule in the base assembly to every molecule in the assembly to be merged;
    d) while there are still molecules in the assembly to be merged which have not been tested, selecting a molecule from the assembly to be merged;
    e) determining whether the molecular structural distance between the selected molecule and every molecule in the base assembly is within the neighborhood distance of the molecular structural descriptor;
    f) selecting for inclusion in the merged assemblies only those molecules identified in step e as having molecular structural distances greater than the neighborhood distance.
    g) repeating step d through step f until all molecules in the assembly to be merged have been tested; and
    h) repeating step b through step g for each additional assembly to be merged; and
    i) outputting the merged assembly of molecules
    wherein the merged assembly of molecules has diversity between and among its members and does not redundantly include molecules likely to share the same activity.

* * * * *